US010732172B1

United States Patent
Ingber et al.

(10) Patent No.: US 10,732,172 B1
(45) Date of Patent: Aug. 4, 2020

(54) METHODS, SYSTEMS, AND COMPOSITIONS FOR DETERMINING BLOOD CLOT FORMATION, AND USES THEREOF

(71) Applicants: President and Fellows of Harvard College, Cambridge, MA (US); Children's Medical Center Corporation, Boston, MA (US)

(72) Inventors: Donald E. Ingber, Boston, MA (US); Abhishek Jain, Roslindale, MA (US); Andries D. van der Meer, Enschede (NL); Alan David Michelson, Boston, MA (US); Andrew L. Frelinger, III, North Reading, MA (US); Riccardo Barrile, Boston, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 154 days.

(21) Appl. No.: 15/576,235

(22) PCT Filed: May 22, 2016

(86) PCT No.: PCT/US2016/033686
§ 371 (c)(1),
(2) Date: Nov. 21, 2017

(87) PCT Pub. No.: WO2016/191332
PCT Pub. Date: Dec. 1, 2016

Related U.S. Application Data

(60) Provisional application No. 62/310,166, filed on Mar. 18, 2016, provisional application No. 62/165,272, filed on May 22, 2015.

(51) Int. Cl.
*G01N 33/50* (2006.01)
*B01L 3/00* (2006.01)
*G01N 33/86* (2006.01)

(52) U.S. Cl.
CPC ........ *G01N 33/5064* (2013.01); *B01L 3/5027* (2013.01); *G01N 33/86* (2013.01); *G01N 2800/226* (2013.01)

(58) Field of Classification Search
None
See application file for complete search history.

(56) References Cited

U.S. PATENT DOCUMENTS

| | | | | |
|---|---|---|---|---|
| 8,445,280 B2 * | 5/2013 | Neumann | ........... | A61L 27/3808 435/395 |
| 2018/0021780 A1 * | 1/2018 | Italiano | ............. | B01L 3/502753 435/395 |

FOREIGN PATENT DOCUMENTS

| | | |
|---|---|---|
| WO | WO 2012/048269 | 4/2012 |
| WO | WO 2014/107240 | 7/2014 |

OTHER PUBLICATIONS

Definition of "lumen" from the medical-dictionary website downloaded from www.https.medical-dictionary.thefreedctionary.com/lumen on Jul. 30, 2019 (Year: 2019).*
Defintion of "fixed" from thefreedictionary.com webiste downloaded from https:www.thefreedictionary.com/fixed on Jul. 30, 2019 (Year: 2019).*
Morgan et al. Nature Protocols (2013) 8(9): 1820-1836 (Year: 2013).*
Young E.W. et al., "Technique for Real-Time Measurements of Endothelial Permeability in a Microfluidic Membrane Chip Using Laser-Induced Fluorescence Detection," Analytical Chemistry, Feb. 1, 2010, vol. 82, Issue 3, pp. 808-816 (15 pages).
Khan O.F. et al., "Endothelial Cell Behavior Within a Microfluidic Mimic of the Flow Channels of a Modular Tissue Engineered Construct," Biomed Microdevices, Feb. 2011, vol. 13, Issue 1, pp. 69-87 (30 pages).
Tsai M. et al., "In Vitro Modeling of the Microvascular Occlusion and Thrombosis That Occur in Hematologic Diseases Using Microfluidic Technology," The Journal of Clinical Investigation, Jan. 2012, vol. 122, No. 1, pp. 408-418 (11 pages).
Zheng, Y. et al., "In Vitro Microvessels for the Study of Angiogenesis and Thrombosis," Proceedings of the National Academy of Sciences (PNAS), Jun. 12, 2012, vol. 109, No. 24, pp. 9342-9347 (6 pages).
Colace T.V. et al., "Microfluidics and Coagulation Biology," Annual Review of Biomedical Engineering, 2013, vol. 15, pp. 283-303 (23 pages).
Schmidt M.-P. et al., "Impedance Spectroscopy Microfluidic Multichannel Sensor Platform for Liquid Analysis," 18th International Conference on Miniaturized Systems for Chemistry and Life Sciences, San Antonio, Texas, USA, Oct. 26-30, 2014, pp. 2137-2139 (3 pages).
Nording et al., "A Novel In vitro Model for Studying the Interactions Between Human Whole Blood and Endothelium," Journal of Visualized Experiments, Nov. 21, 2014, Issue 93, e52112 (6 pages).
International Search Report and Written Opinion of the International Searching Authority in corresponding International Application No. PCT/US2016/033686, dated Jan. 25, 2017 (18 pages).

* cited by examiner

*Primary Examiner* — Susan M Hanley
(74) *Attorney, Agent, or Firm* — Nixon Peabody LLP

(57) ABSTRACT

A method is directed to determining a thrombosis function and includes flowing a fluid sample over a surface having a fixed endothelial cell monolayer. The method further includes stimulating the fixed endothelial cell monolayer to induce formation of a clot, the clot being formed via interaction between the fixed endothelial cell monolayer and the fluid sample. In response to the clot formation, the method further includes determining a thrombosis function associated with the fluid sample and the fixed endothelial cell monolayer.

21 Claims, 40 Drawing Sheets

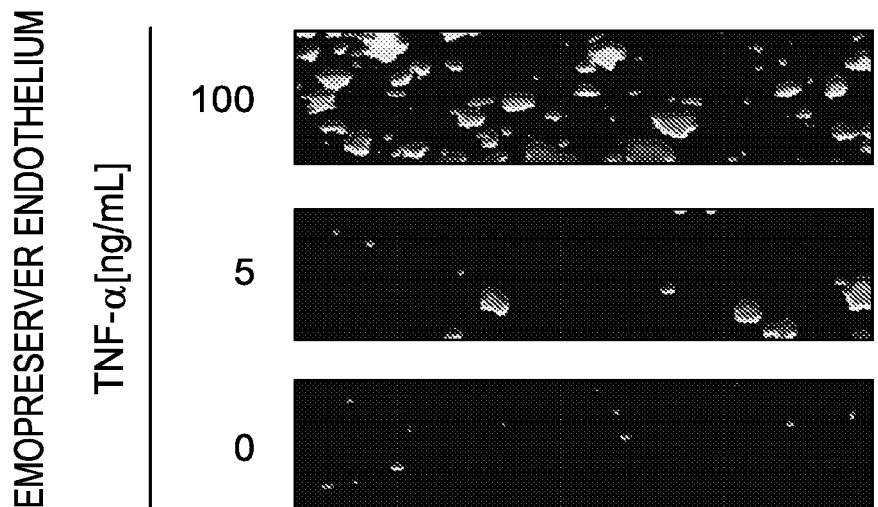
FIG. 9
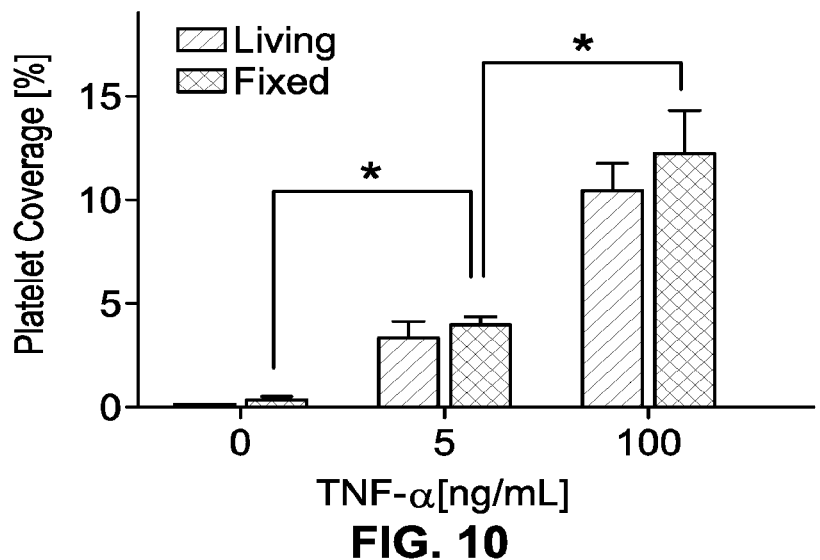
FIG. 10
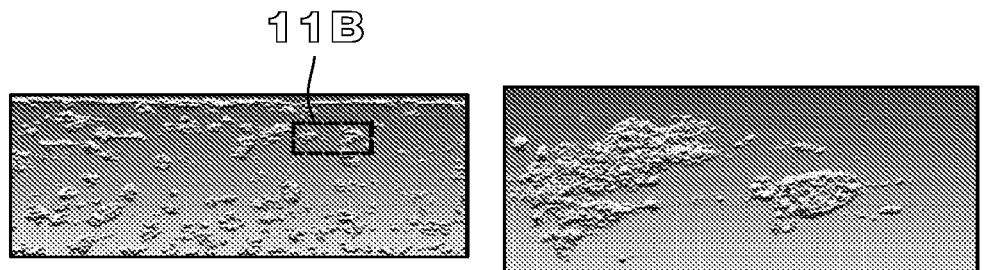
FIG. 11A     FIG. 11B

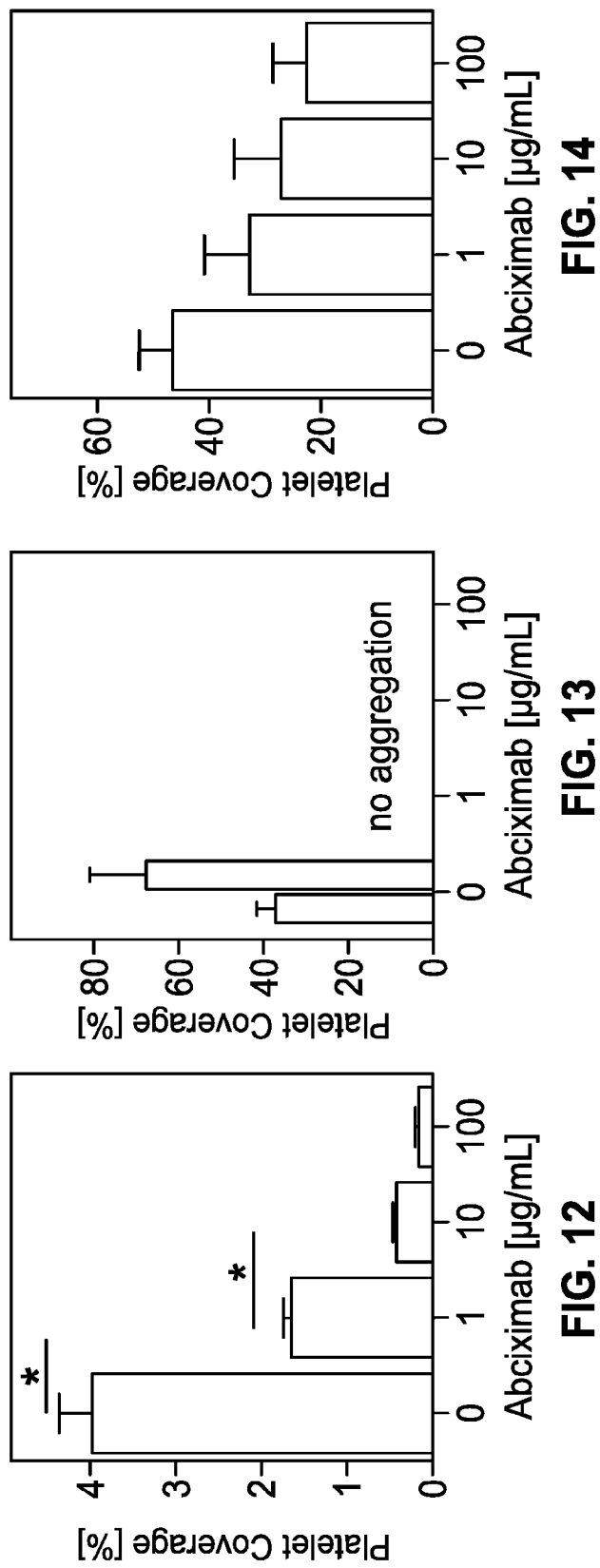

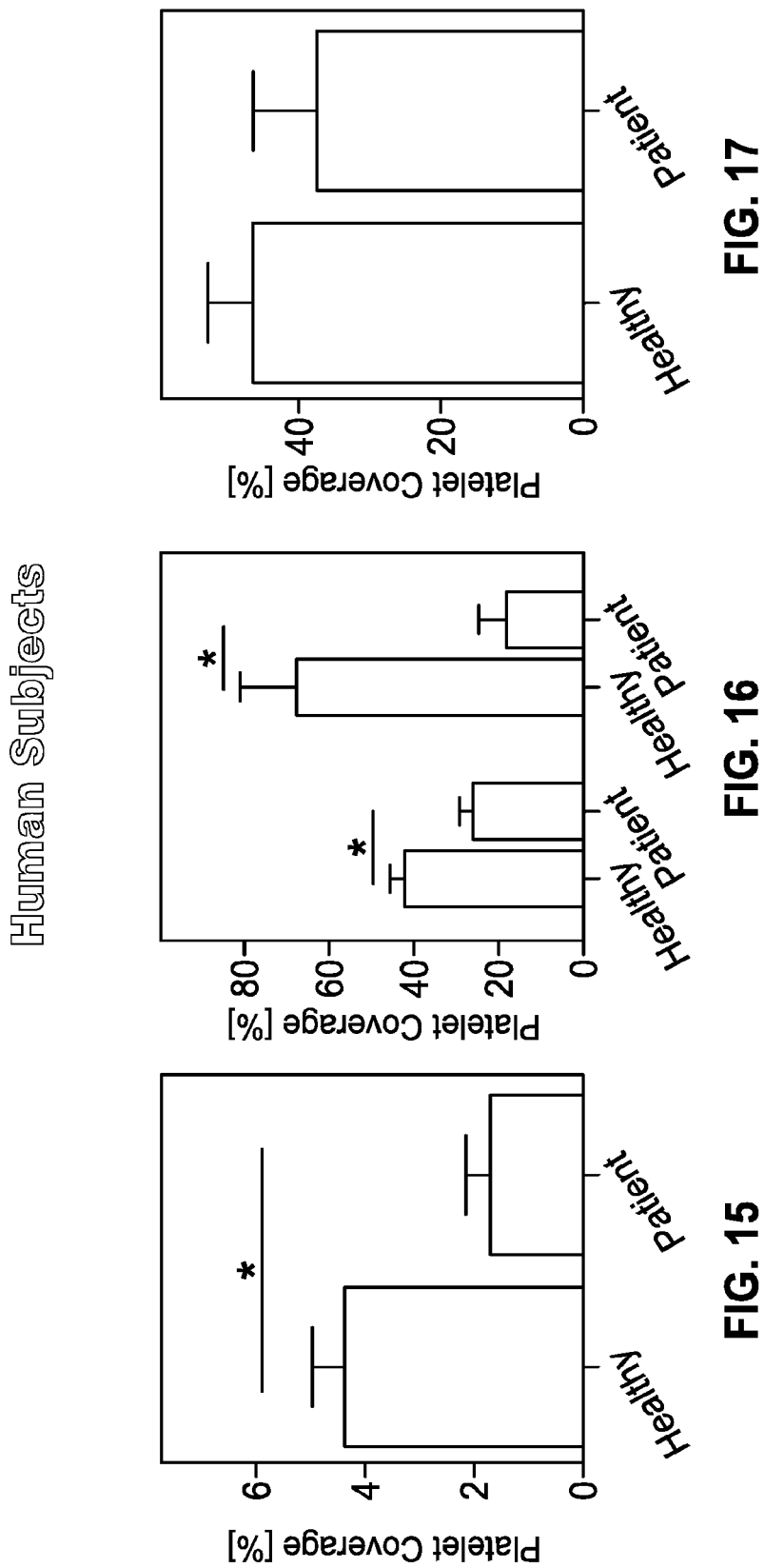

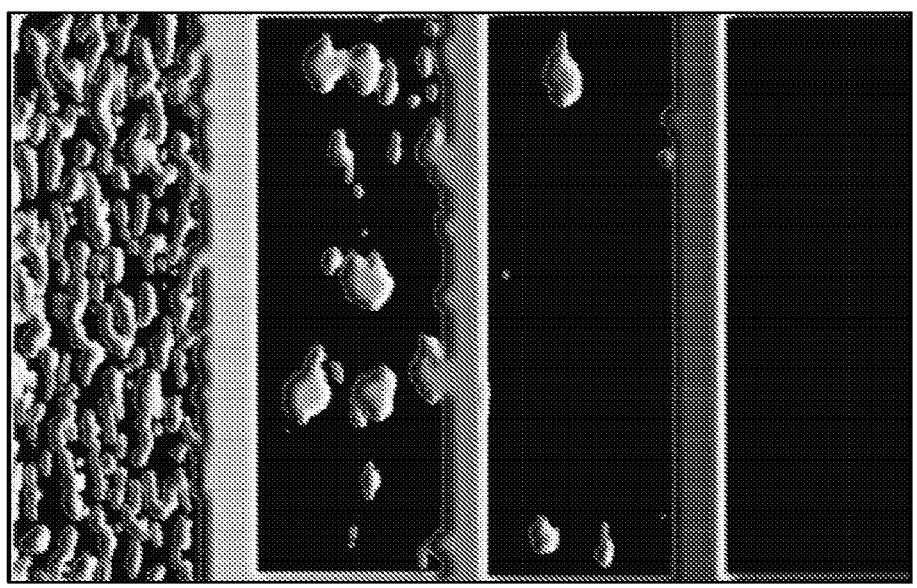
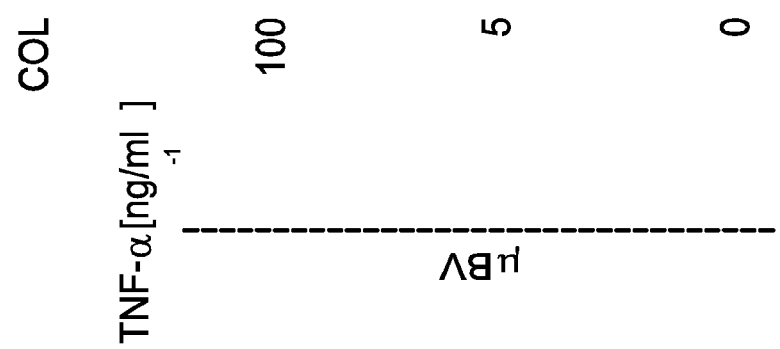
FIG. 21
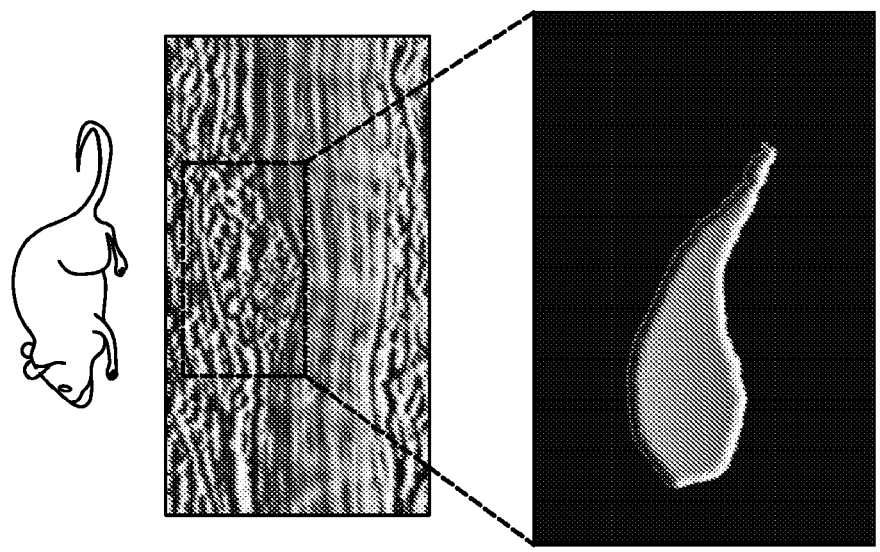
FIG. 20

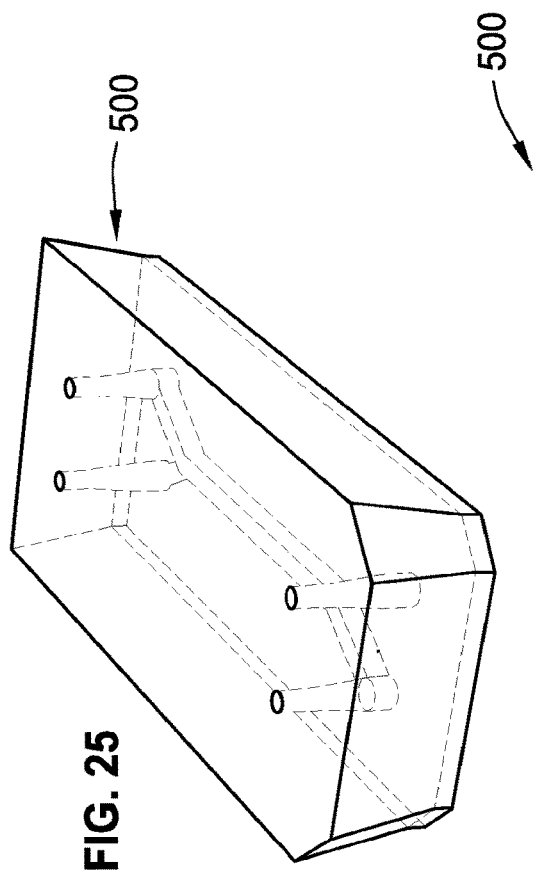
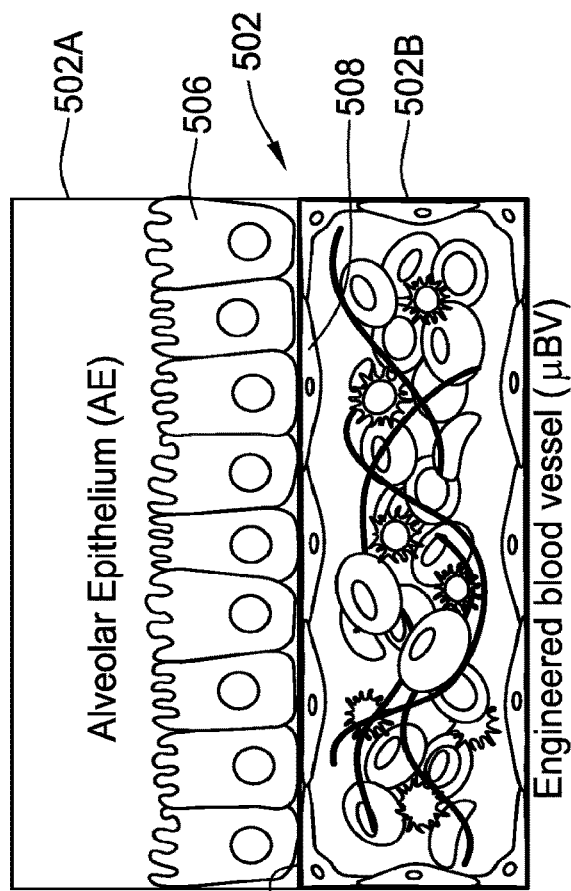
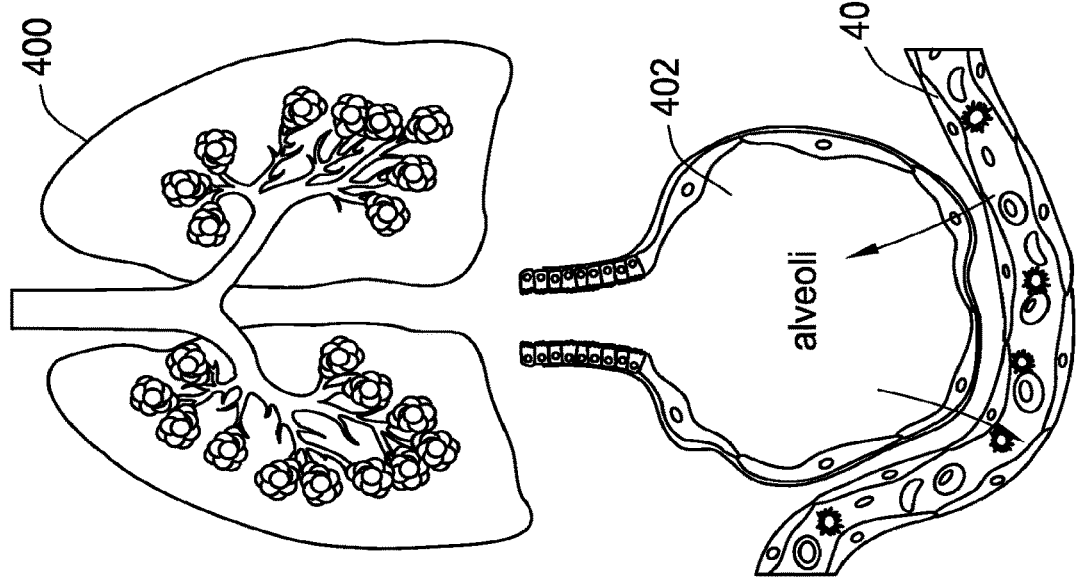
FIG. 25
FIG. 26
FIG. 24

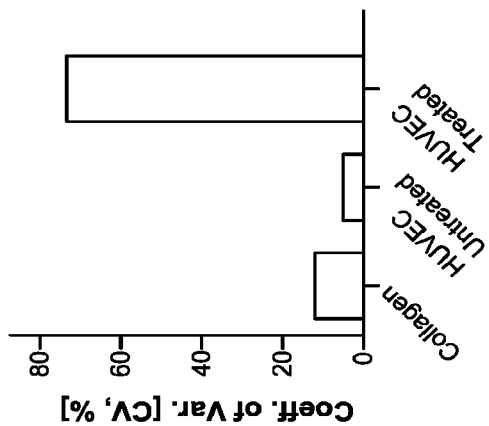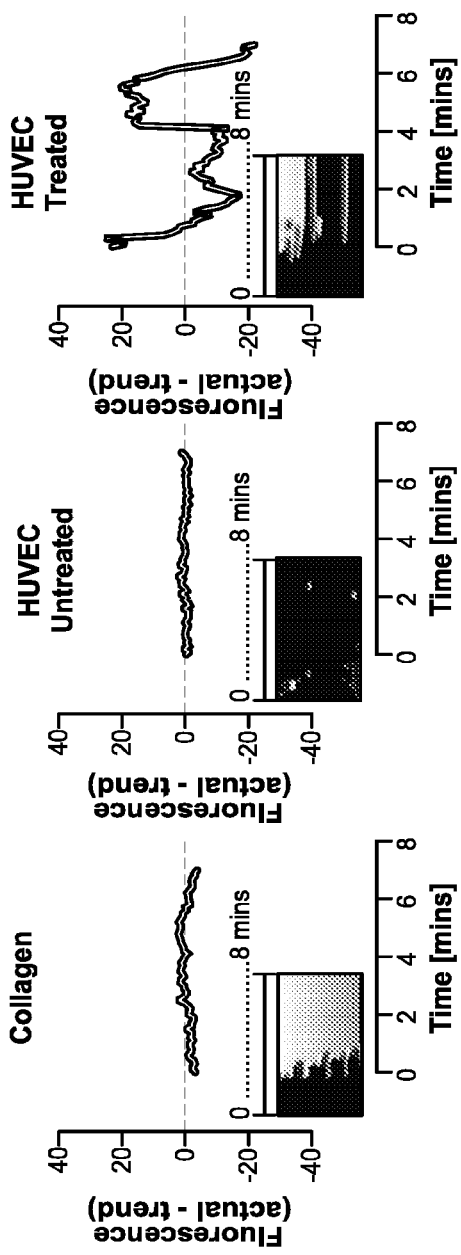
FIG. 46
FIG. 45
FIG. 44
FIG. 43

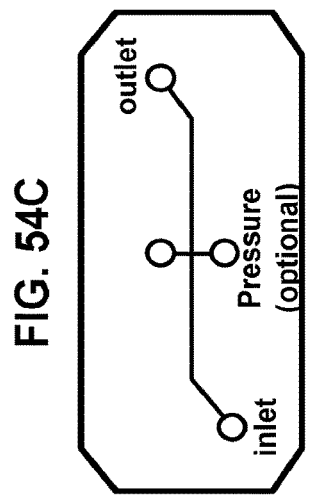
FIG. 54A
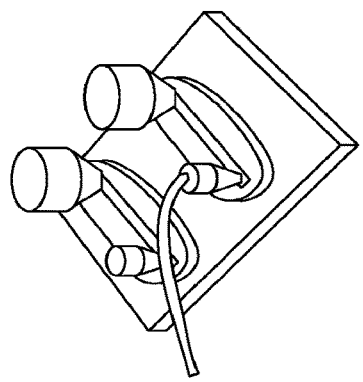
FIG. 54B
FIG. 54C
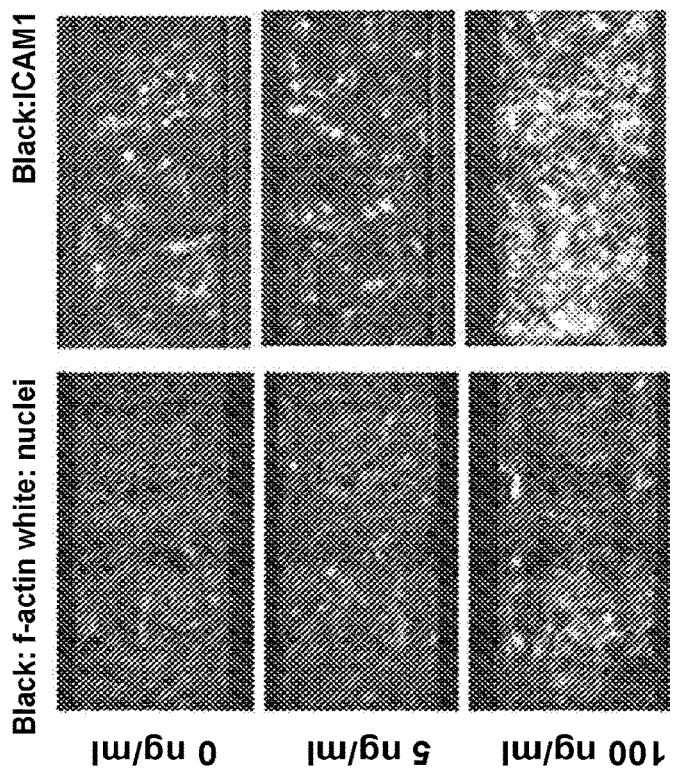
FIG. 54E
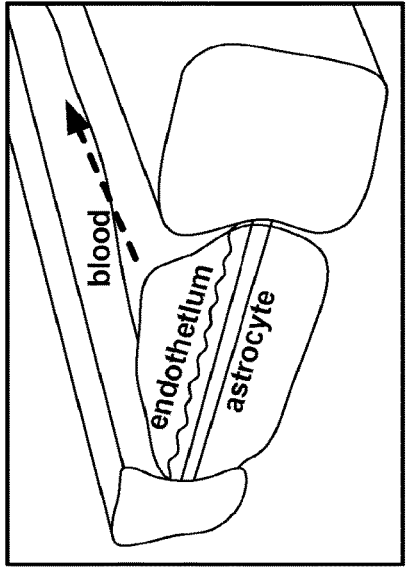
FIG. 54D

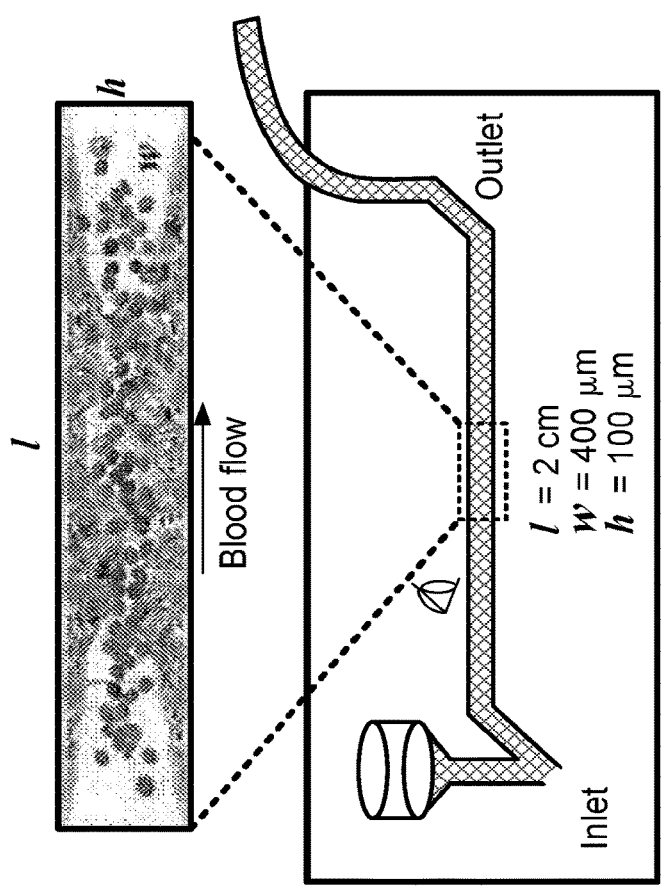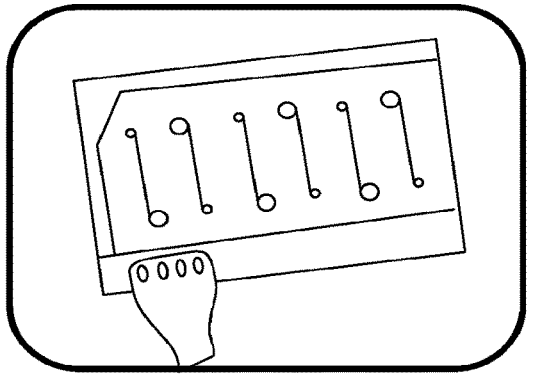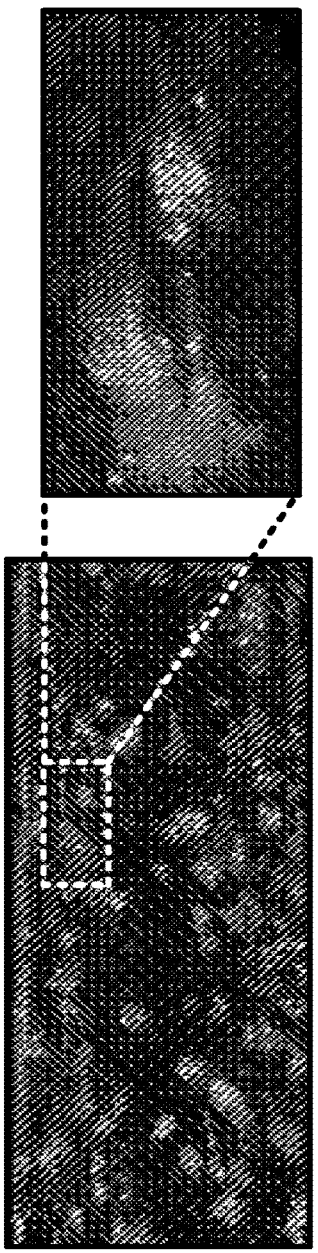
FIG. 65A
FIG. 65B
FIG. 65C

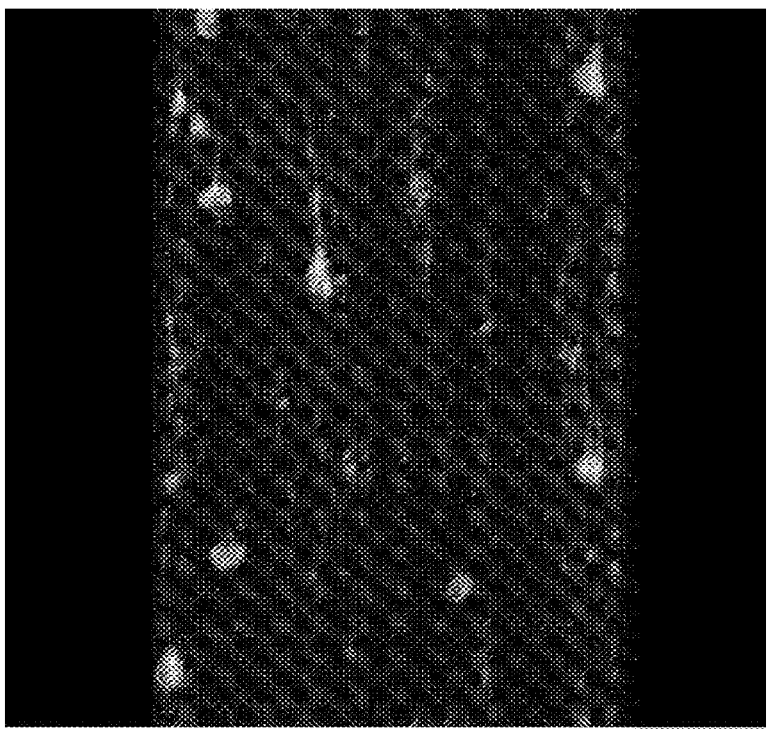
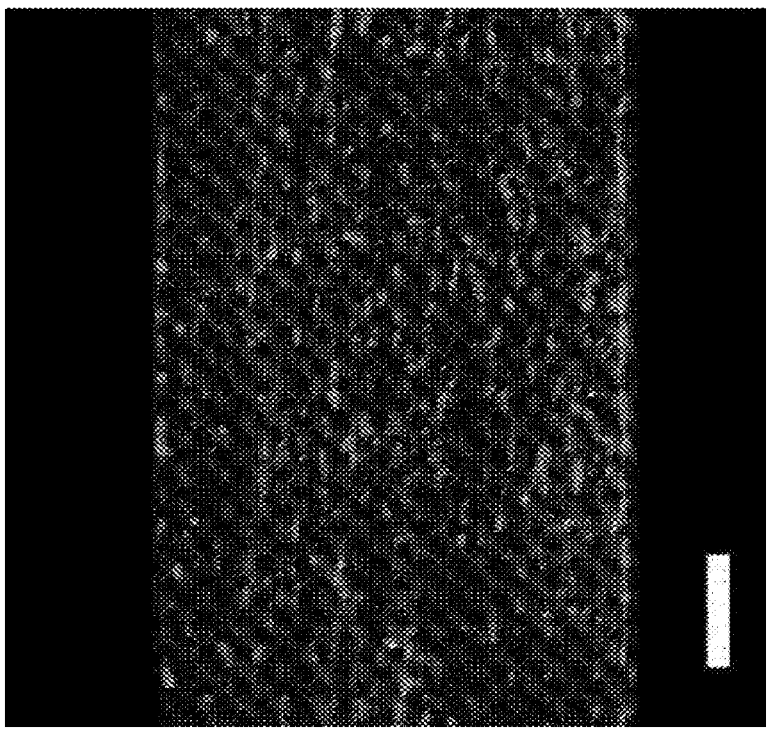
FIG. 76

METHODS, SYSTEMS, AND COMPOSITIONS FOR DETERMINING BLOOD CLOT FORMATION, AND USES THEREOF

CROSS-REFERENCE TO RELATED APPLICATIONS

This application is a national stage of International Application No. PCT/US2016/033686, filed on May 22, 2016, and titled "Methods, Systems, And Compositions For Determining Blood Clot Formation, And Uses Thereof," which claims priority to and benefit of U.S. Provisional Patent Application Ser. No. 62/165,272, filed on May 22, 2015, and titled "Methods, Systems, And Compositions For Determining Platelet Function, And Uses Thereof," and U.S. Provisional Patent Application Ser. No. 62/310,166, filed on Mar. 18, 2016, and titled "Methods, Systems, And Compositions For Determining Blood Clot Formation, And Uses Thereof," each of which is hereby incorporated by reference herein in its entirety.

GOVERNMENT SUPPORT

The invention was made with Government Support under N66001-11-1-4180 awarded by the Space and Naval Warfare Systems Center of the U.S. Department of Defense, and under HR0011-13-C-0025 awarded by the Defense Advanced Research Projects Agency of the U.S. Department of Defense. The government has certain rights in the invention.

FIELD OF THE INVENTION

The present invention relates generally to quantifying a thrombosis-related function in vitro based on physiologically relevant conditions, and, more particularly, to a microfluidic system having fluid flow interaction between a fixed endothelial layer and cells (such as platelets) in a fluid sample.

BACKGROUND OF THE INVENTION

Generally, the vascular endothelium and shear stress are critical determinants of hemostasis and platelet function in vivo, and yet, current diagnostic and monitoring devices do not fully incorporate endothelial function under flow in their assessment. Therefore, current diagnostic and monitoring devices can be unreliable and inaccurate. Furthermore, it is challenging to include the endothelium in assays for clinical laboratories or point-of-care settings because living cell cultures are not sufficiently robust.

More specifically, mutual signaling between endothelium and activated platelets is widely recognized as critical for regulation of hemostasis and thrombotic disorders associated with various diseases, including atherosclerosis, sepsis, and diabetes. Yet, no practical diagnostic assays exist that can measure cross-talk between platelets and inflamed vessel walls in the presence of physiological shear. Over the last decade or so, multiple flow chambers and microfluidic devices that contain microchannels have been lined by living endothelium and exposed to flowing blood to study the basic science of thrombosis. While these devices have been very useful in advancing research, they have not been used in clinical settings due to the difficulty in maintaining living endothelial cells in them. Specifically, because it is extremely difficult to maintain the viability of living cell cultures for extended times in non-controlled settings, it is virtually impossible to rely on these assays. Therefore, the only microfluidic devices that are currently being deployed in clinical diagnostic settings are lined with collagen to mimic thrombus formation and platelet aggregation induced in response to vascular injury, and, thus, they fail to capture the physiological interplay between endothelial cells, platelets and fluid shear stress that is so relevant to hemostasis in inflammatory diseases.

Additionally, pulmonary microvascular thrombosis is a catastrophic condition amounting to a large number of patient deaths worldwide. Despite significant progress in understanding fundamental biology of lung hemostasis and thrombosis, it is still very difficult to predict response and study mechanism of action of potential drug candidates to humans. This is partly so because currently available in vitro assays do not recapitulate physiologically-relevant forces, such as shear stress, and animal models can be very complex allowing limited experimental manipulation, making it impossible to dissect and study intercellular signaling.

More specifically, pulmonary intravascular thrombosis and platelet activation initiating from, for example, acute lung injury ("ALI"), acute chest syndrome ("ACS"), pulmonary hypertension ("PH"), chronic obstructive pulmonary disease ("COPD"), and acute respiratory distress syndrome ("ARDS"), are causes of significantly high patient mortality and morbidity. Therefore, pulmonary intravascular thrombosis and platelet activation are also promising and emerging therapeutic targets to save and prolong patient life. Although epithelial injury, endothelial dysfunction, and in situ thrombotic lesions are observed often in human patients in chronic pulmonary diseases, animal models of pulmonary dysfunction are still unable to completely mimic the altered hemostasis and hemodynamic complexity of the lung. Importantly, animal models can be very complex and it may be impossible to study cell-cell interactions between multiple tissues independently of each other during blood clotting or drug administration. Based on this type of limitations, along with ethical barriers associated with animal models, it is desirable to advance in vitro disease models of pulmonary thrombosis that can mimic human organ-level functionality and complement or reduce reliance on animal studies, to enable more reliable basic research and make drug discovery more efficient.

In vitro, commercially available coagulation and platelet function technologies also have serious limitations due to the fact that they do not incorporate physiological tissue-tissue or cell-cell interactions, and relevant fluid dynamics of blood cells, which are key determinants of thrombosis. In research laboratories, dishes and transwell plates have been used for decades to culture cells and study basic biology, but these are static systems, highly non-physiological and cannot recapitulate tissue or organ-level functionality. For example, this type of systems cannot recapitulate blood flow or breathing of a lung.

To incorporate blood perfusion, parallel plate-flow chambers have been widely applied in the past three decades or so to measure thrombus formation and platelet adhesion kinetics. However, being macroscale devices, these chambers do not mimic small blood vessels, typically do not incorporate endothelium, and require large blood sample volumes for analysis.

More recently, microfluidic devices lined with human endothelial cells have shown that endothelial activation, platelet adhesion and fibrin formation in the presence of physiological shear can be somewhat visualized. However, these devices are also limited in studying organ-level pulmonary thrombosis, in part because they do not include the role of live epithelial cells, dynamic platelet-endothelial interactions (e.g., activation, aggregation, adhesion, translocation, and embolization) in the lumen that occur over large spatiotemporal scales, and often do not incorporate perfusion of whole blood.

Recently, microfluidic technology has been advanced to demonstrate an organ-level in vitro model of a lung and pulmonary edema, where alveolar epithelial and endothelial cells were co-cultured in two overlaying chambers, respectively. Fibrin formation in the alveolar chamber was analyzed in the presence of an inflammatory cytokine IL-2 and in the presence of flow and relevant cyclic stretch. However, this type of lung-on-a-chip model still lacks relevant functionality for mimicking relevant foundational conditions of pulmonary thrombosis. For example, the endothelial chamber only contains one side cultured with the cells and hence, it does not contain an endothelial lumen. Based on this limitation, the device is not appropriate for perfusing whole blood and for studying blood cell-endothelial interactions. In fact, other than a dilute suspension of neutrophils, none of the blood cells or platelets has been perfused or analyzed in this type of device, in its physiological concentration.

Another limitation of the long-on-a-chip model is that it uses non-primary epithelial cell lines, A549 or NCI-H441. Although this type of model mimics certain aspects of human lung function, it is not ideal in the context of mimicking physiologically-relevant hemostasis and thrombosis, as they are derived from tumors and, therefore, can potentially alter endothelial and platelet function.

Therefore, there is a continuing need for solving the above and other problems.

SUMMARY OF THE INVENTION

According to one aspect of the present invention, a microfluidic device is lined with a human endothelium that is chemically fixed, but still retains its ability to modulate hemostasis under continuous flow in vitro. For example, according to one method, microfluidic channels are seeded with collagen and endothelial cells and are left either untreated or treated with tumor necrosis factor-α (TNF-α). The cells are, then, fixed with formaldehyde. Recalcified citrated whole blood (0.5 mL) from healthy volunteers or patients taking antiplatelet medication is perfused and platelet coverage is recorded. The chemopreserved endothelialized device is lined with a bioinspired material that supports formation of platelet-rich thrombi in the presence of physiological shear, similar to a living arterial vessel. Furthermore, the method demonstrates the potential clinical value of the chemopreserved endothelialized device by showing that thrombus formation and platelet function are measurable within minutes using a small volume of whole blood taken from subjects receiving antiplatelet medications. The method further demonstrates potentially greater reliability than standard platelet function tests and collagen-coated perfusion chambers.

According to another aspect of the present invention, a microengineered lung-on-chip device is used for studying human pulmonary blood clotting and platelet-endothelial interaction dynamics. The lung-on-chip is a microfluidic device populated with primary alveolar cells ("AE") localized within a top channel and vascular endothelial cells in a bottom compartment. The top channel and the bottom compartment are separated by a matrix-coated membrane. Whole blood is perfused in the vascular compartment while the epithelium is stimulated with a cytokine or endotoxin, and platelet-endothelial interactions are recorded in real-time. To quantify the dynamics of the platelet-endothelial interactions, a stochastic analytical method is provided that is highly sensitive to changes in endothelial and platelet activation. In vitro, the presence of alveolar epithelium is shown to be beneficial for reconstituting pulmonary thrombosis in response to an inflammatory stimulus of lipopolysaccharide ("LPS"). Additionally, this model is used in drug development by analyzing the effect of a novel protease activator receptor-1 ("PAR1") antithrombotic compound, termed parmodulin 2 ("PM2"), and demonstrate that PM2 has an endothelial cytoprotective effect in response to LPS-mediated inflammation. The lung-on-chip device reconstitutes organ-level functionality that accurately reflects many aspects of human pulmonary thrombosis and appears to offer a valuable platform for drug development.

According to one aspect of the present invention, a method is directed to determining a thrombosis function and includes flowing a fluid sample over a surface having a fixed endothelial cell monolayer. The method further includes stimulating the fixed endothelial cell monolayer to induce formation of a clot, the clot being formed via interaction between the fixed endothelial cell monolayer and the fluid sample. In response to the clot formation, the method further includes determining a thrombosis function associated with the fluid sample and the fixed endothelial cell monolayer.

According to another aspect of the invention, a microfluidic system is directed to determining a thrombosis function. The microfluidic system includes a compartment having a surface with a fixed endothelial cell monolayer, the compartment being configured to receive a fluid sample flowing over the surface such that cells in the fluid sample interact with the fixed endothelial cell monolayer. The microfluidic system further includes a detection module configured to detect interaction between the cells and the fixed endothelial cell monolayer, and to determine a function of the cells in the fluid sample.

According to yet another aspect of the invention, a device is directed to simulating a function of a tissue. The device includes a first structure defining a first microchannel and configured to have a fluid sample flowing within, the fluid sample including platelets. The device further includes a second structure defining a second microchannel, and a membrane located at an interface region between the first microchannel and the second microchannel. The membrane has a first side facing toward the first microchannel and a second side facing toward the second microchannel, the membrane separating the first microchannel from the second microchannel. The first side of the membrane includes a fixed endothelial cell monolayer, the second side of the membrane including at least one layer of tissue-specific cells. The device further includes a detection module configured to detect interaction between the platelets and the fixed endothelial cell monolayer. The detection module is further configured to determine a function of the platelets in the fluid sample.

According to yet another aspect of the invention, a system is directed to quantifying thrombosis in vitro based on physiological conditions. The system includes a solid substrate having a surface with a fixed endothelial cell monolayer, and a detection module configured to receive the solid substrate. The detection module is further configured to detect spatial and temporal interaction between cells in a fluid sample and the surface of the solid substrate when the fluid sample is flowed over the surface along a flow axis. The system further includes one or more controllers configured to store time-lapse data of detectable signals collected from the detection module, wherein the detectable signals represent spatial and temporal interaction between the cells and the surface.

The one or more controllers are further configured to generate a kymograph from at least a portion of the stored time-lapse data, wherein a time axis of the kymograph indicates at least a portion of the time-lapse duration, a space axis of the kymograph indicating the detectable signals along the flow axis. The one or more controllers are further, yet, configured to determine, based on the generated kymograph, a rate of fluctuation in a coefficient of variation (CV) of the detectable signals to generate a temporal cell dynamics index, and to determine either (i) the presence of reactive cells in the fluid sample when the temporal cell dynamics index is higher than a temporal control value, or (ii) the absence of reactive cells in the fluid sample when the temporal cell dynamics index is no more than the temporal control value. The system further includes a display module for displaying content that is based in part on output determined by the one or more controllers, wherein the content includes a signal indicative of either presence or absence of at least one of reactive cells or cell aggregation in the fluid sample.

According to yet another aspect of the invention, a method is directed to quantifying thrombosis in vitro based on physiological conditions. The method includes providing a solid substrate having a surface with a fixed endothelial cell monolayer, and detecting, via a detection module, spatial and temporal interaction between cells in a fluid sample and the surface of the solid substrate when the fluid sample is flowed over the surface along a flow axis. The method further includes storing, via one or more controllers, time-lapse data of detectable signals that are collected from the detection module, the detectable signals representing spatial and temporal interaction between the cells and the surface. The method also includes generating a kymograph, via at least one of the one or more controllers, from at least a portion of the stored time-lapse data, a time axis of the kymograph indicating at least a portion of the time-lapse duration, a space axis of the kymograph indicating the detectable signals along the flow axis.

Based on the generated kymograph, the method determines, via at least one of the more controllers, a rate of fluctuation in a coefficient of variation (CVO) of the detectable signals to generate a temporal cell dynamics index. The method further includes determining, via at least one of the one or more controllers, (i) the presence of reactive cells in the fluid sample when the temporal cell dynamics index is higher than a temporal control value, or (ii) the absence of reactive cells in the fluid sample when the temporal cell dynamics index is no more than the temporal control value. The method further includes displaying, via a display module, content that is based in part on output determined by the one or more controllers, the content including a signal indicative of either presence or absence of at least one reactive cells or cell aggregation in the fluid sample.

According to yet another aspect of the invention, a system is directed to determining dynamics of platelets in a fluid sample. The system includes a solid substrate having a surface with a fixed endothelial cell monolayer, and a detection module configured to receive the solid substrate. The detection module is further configured to detect spatial and temporal interaction between cells in a fluid sample and the surface of the solid substrate when the fluid sample is flowed over the surface along a flow axis. The system further includes one or more controllers configured to store time-lapse data of detectable signals collected from the detection module, wherein the detectable signals represent spatial and temporal interaction between the cells and the surface.

The one or more controllers are further configured to generate a kymograph from at least a portion of the stored time-lapse data, wherein a time axis of the kymograph indicates at least a portion of the time-lapse duration, a space axis of the kymograph indicating the detectable signals along the flow axis. The one or more controllers are also configured to determine, based on the generated kymograph, a rate of fluctuation in a coefficient of variation (CV) of the detectable signals to generate a platelet dynamics index, the platelet dynamics index being one or more of a temporal platelet dynamics index and a spatial platelet dynamics index. The one or more controllers are further configured to determine either (i) the presence of reactive platelets in the fluid sample when the platelet dynamics index is higher than a control value, or (ii) the absence of reactive platelets in the fluid sample when the platelet dynamics index is no more than the control value. The system further includes a display module for displaying content that is based in part on output determined by the one or more controllers, wherein the content includes a signal indicative of either presence or absence of at least one of reactive platelets or platelet aggregation in the fluid sample.

In addition, the inventors have shown that the fixed endothelial cell monolayers that have been stored for a period of time (e.g., at least about 5 days or more) without freezing were still applicable for platelet function analysis. Not only can this concept be applied to platelet function analysis, but it can also be generally extended to analyses of interaction dynamics of other cell types.

Further, instead of merely determining area-averaged platelet adhesion—a static analysis—as regularly used in existing platelet function assessment, the inventors have developed novel analytical methods to quantify temporal and/or spatial changes in the way of how cells interact with each other and/or to a surface. In some embodiments, the inventors have showed that the resulting characteristic temporal and spatial indices were sensitive enough to distinguish activated platelets (e.g., due to inflamed endothelial cells) and non-activated platelets. Thus, the temporal and spatial indices can be used as markers to diagnose diseases or disorders (e.g., platelet-associated disease or disorder), to select appropriate therapy (e.g., anti-platelet and/or anti-inflammation therapy), to monitor treatment efficacy (e.g., to prevent recurrent thrombosis or bleeding), drug screening and/or to determine drug toxicology. Accordingly, embodiments of various aspects described herein relate to methods, systems, and compositions for determining dynamic interaction of cells with each other, and/or with other cell types, and uses thereof.

One aspect described herein relates to a method of determining cell function. The method comprises (a) flowing a fluid sample over a surface comprising a monolayer of cells of a first type thereon; and (b) detecting interaction between cells of a second type in the fluid sample and the monolayer of cells of the first type. The function of the cells of the second type in the fluid sample can then be determined based on the detected cell interaction.

In some embodiments, the fixed monolayer of cells of the first type can comprise endothelial cells, and the cells of the second type in the fluid sample can comprise blood cells, e.g., platelets. Accordingly, another aspect provided herein relates to a method of determining platelet function, which comprises (a) flowing a fluid sample over a surface comprising a fixed endothelial cell monolayer thereon; and (b)

detecting interaction between blood cells (e.g., platelets) in the fluid sample and the fixed endothelial cell monolayer.

In some embodiments, the fixed cell monolayer (e.g., fixed endothelial cell monolayer) can be derived from fixing target cell extract (e.g., endothelial cell extract) and/or target cell-associated proteins (e.g., endothelial cell-associated proteins) that are adhered to the surface. The target cell-associated proteins can comprise proteins secreted by the target cells and/or present on the target cell surface. Where the target cell-associated proteins comprise endothelial cell-associated proteins, examples of endothelial cell-associated proteins can include, but are not limited to, any art-recognized procoagulatory and/or anti-coagulatory proteins. In some embodiments, the endothelial cell-associated proteins can comprise von Willebrand factor and/or tissue factor (TF).

Any cell-comprising fluid sample can be flowed over the fixed cell monolayer and it can vary depending on what target cells to be analyzed. In some embodiments, the fluid sample can comprise a blood sample, a serum sample, a plasma sample, a lipid solution, a nutrient medium, or a combination of two or more thereof. In some embodiments when the fluid sample comprises a blood sample, the method can further comprise removing red blood cells from the blood sample prior to flowing the blood sample over the surface. In some embodiments, the fluid sample flowing over the surface in the methods described herein can comprise calcium ions and/or magnesium ions.

The surface over which the fluid sample flows can be a surface of any fluid-flowing conduit disposed in a solid substrate that is compatible to the fluid sample and the cells. In some embodiments, the solid substrate can comprise a cell culture chamber. For example, in one embodiment, the surface can be a wall surface of a microchannel. In one embodiment, the surface can be a surface of a membrane.

In some embodiments where the surface is a surface of a membrane, the membrane can be configured to separate a first chamber (e.g., a first microchannel) and a second chamber (e.g., a second microchannel) in a microfluidic device.

In some embodiments, the microfluidic device can be configured to comprise an organ-on-chip device. An exemplary organ-on-chip can comprise a first chamber (e.g., a first microchannel), a second chamber (e.g., a second microchannel), and a membrane separating the first chamber and the second chamber. In these embodiments, a first surface of the membrane facing the first chamber can comprise the fixed cell monolayer (e.g., fixed endothelial cell monolayer) thereon, and a second surface of the membrane facing the second chamber can comprise tissue-specific cells adhered thereon. In some embodiments, the membrane can be replaced or embedded with extracellular matrix proteins (e.g., but not limited to collagen, laminin, etc.). In some embodiments, the membrane can also comprise smooth muscle cells and/or fibroblasts.

In some embodiments, the fixed cell monolayer (e.g., fixed endothelial cell monolayer) can be derived from fixing a layer of cells of the first type (e.g., an endothelial cell monolayer) that has been grown on the surface for a period of time. For example, the layer of cells of the first type (e.g., an endothelial cell monolayer) can grow on the surface until it reaches confluence and is then subjected to a fixation treatment as described herein.

Various methods for fixing cells that are adhered to a surface are known in the art and can be used herein to generate a fixed cell monolayer. In some embodiments, the cell monolayer (e.g., endothelial cell monolayer) can be physically fixed by drying and/or dehydration. In some embodiments, the cell monolayer (e.g., endothelial cell monolayer) can be physically fixed by exposing to air, and/or washing with alcohol, acetone or a solvent that removes water and/or lipids. In some embodiments, the cell monolayer (e.g., endothelial cell monolayer) can be fixed with a chemical fixative. Non-limiting examples of chemical fixatives include formaldehyde, paraformaldehyde, formalin, glutaraldehyde, mercuric chloride-based fixatives (e.g., Helly and Zenker's solution), precipitating fixatives (e.g., ethanol, methanol, and acetone), dimethyl suberimidate (DMS), Bouin's fixative, and a combination of two or more thereof. In one embodiment, the chemical fixative for fixing the cell monolayer (e.g., endothelial cell monolayer) can comprise paraformaldehyde. In some embodiments, the cell monolayer (e.g., endothelial cell monolayer) can be fixed with a decellularization solvent that stabilizes surface membrane protein configuration and cytoskeleton of a cell. For example, the decellularization solvent can comprise an aqueous solution comprising a detergent and/or a high pH solution.

The fixed cell monolayer (e.g., fixed endothelial cell monolayer) can be derived from a cell line or cells collected from a subject. In some embodiments, cells collected from a subject can be reprogrammed to form pluripotent stem cells, which are then differentiated into target cells to generate a fixed cell monolayer.

The fixed cell monolayer (e.g., fixed endothelial cell monolayer) can be derived from cells of any condition. In some embodiments, the fixed cell monolayer (e.g., fixed endothelial cell monolayer) can be derived from healthy cells. In some embodiments, the fixed cell monolayer (e.g., fixed endothelial cell monolayer) can be derived from diseased cells. In some embodiments, the diseased cells can be derived from a subject (e.g., a healthy subject or a subject diagnosed with a disease or disorder of interest). In some embodiments, the diseased cells can be generated by contacting healthy cells (e.g., healthy endothelial cells) with a condition-inducing agent (e.g., inflammation-inducing agent) prior to the fixation treatment. The condition-inducing agent (e.g., inflammation-inducing agent) can comprise a physical stimulus, a chemical agent, a biological agent, a molecular agent, or a combination of two or more thereof.

By detecting interaction between cells (e.g., blood cells such as platelets) in the fluid sample and the fixed cell monolayer (e.g., fixed endothelial cell monolayer), temporal and/or spatial dynamics of the cells in the fluid sample interacting with each other and/or to the fixed cell monolayer can be measured. In some embodiments, the measured temporal and/or spatial dynamics of cell interaction measured can comprise cell adhesion, cell detachment, cell translocation, and cell embolization/aggregation. In some embodiments, the measured temporal and/or spatial dynamics of cell interaction can comprise binding dynamics of the cells (e.g., blood cells such as platelets) to the fixed cell monolayer (e.g., fixed endothelial cell monolayer), binding dynamics of the cells (e.g., blood cells such as platelets) to each other, or a combination thereof.

Depending on cell detection methods, the cells in the fluid sample can be label-free or labeled, e.g., with a detectable label. An exemplary detectable label can comprise a fluorescent label.

Any art-recognized cell detection methods can be used to detect interaction between the cells in the fluid sample and the fixed cell monolayer. In some embodiments, an imaging-based method can be used. An exemplary imaging-based method can comprise time-lapse microscopy.

The inventors have showed that the fixed endothelial cell monolayer can be stored for a period of time without undermining its applicability to platelet dynamics analysis. Accordingly, in some embodiments, the surface comprising the fixed cell monolayer (e.g., fixed endothelial cell monolayer) can have been stored for a period of time prior to flowing the fluid sample over the surface. In some embodiments, the fixed cell monolayer (e.g., fixed endothelial cell monolayer) can be stored at a non-freezing temperature. For example, in some embodiments, the fixed cell monolayer (e.g., fixed endothelial cell monolayer) can be stored at room temperature. In some embodiments, the fixed cell monolayer (e.g., fixed endothelial cell monolayer) can be stored at a temperature of about 4° C. or lower. In some embodiments, the fixed cell monolayer (e.g., fixed endothelial cell monolayer) can be stored at a temperature of about 4° C.–10° C.

The period of time to store the fixed cell monolayer (e.g., fixed endothelial cell monolayer) can vary with the selected storage temperature. In some embodiments, the period of time can be at least about 1 day or longer. In some embodiments, the period of time can be at least about 5 days or longer.

The fluid sample can be flowed over the surface comprising the fixed cell monolayer (e.g., fixed endothelial cell monolayer) at a pre-determined shear rate or flow rate. For example, the fluid sample can be flowed over the surface at a flow rate that generates a physiological or pathological wall shear rate. For example, the physiological or pathological wall shear rate can range from about 50 $sec^{-1}$ to about 10,000 $sec^{-1}$.

The fixed cell monolayer (e.g., fixed endothelial cell monolayer) and the fluid sample can be derived from the same subject or from different sources.

In some embodiments, the fixed cell monolayer can comprise a fixed endothelial cell monolayer, and the fluid sample cells can comprise blood cells such as platelets. Accordingly, in these embodiments, the system can be used to determine spatial dynamics of blood cells such as platelets in a fluid sample.

The methods and/or systems described herein can provide tools to diagnose a disease or disorder induced by cell dysfunction or abnormal cell-cell interaction in a subject. Accordingly, another aspect described herein relates to a method of determining if a subject is at risk, or has, a disease or disorder induced by cell dysfunction or abnormal cell-cell interaction. The method comprises: (a) flowing a fluid sample of the subject over a surface comprising a fixed cell monolayer thereon; (b) detecting interaction of cells in the fluid sample between each other and/or with the fixed cell monolayer; and (d) identifying the subject to be at risk, or have the disease or disorder induced by cell dysfunction when the cell-cell interaction is higher than a control; or identifying the subject to be less likely to have a disease or disorder induced by cell dysfunction when the cell-cell interaction is no more than the control.

In some embodiments, the living or fixed cell monolayer used in the methods described herein can be subject-specific.

In some embodiments, the method of determining if a subject is at risk, or has a disease or disorder induced by cell dysfunction and/or abnormal cell-cell interaction can be used for diagnosis and/or prognosis of a disease or disorder induced by blood cell dysfunction (e.g., platelet dysfunction), and/or guiding and/or monitoring of an anti-platelet and/or anti-inflammation therapy. Accordingly, in some embodiments, the fixed endothelial cell monolayer can comprise a fixed endothelial cell monolayer. The fixed endothelial cell monolayer can be subject-specific. In some embodiments, the fluid sample can comprise blood cells such as platelets. Thus, a method of determining if a subject is at risk, or has a disease or disorder induced by blood cell dysfunction (e.g., platelet dysfunction) is also described herein. Non-limiting examples of the disease or disorder induced by blood cell dysfunction (e.g., platelet dysfunction) include, but are not limited to thrombosis, an inflammatory vascular disease (e.g., sepsis, or rheumatoid arthritis), a cardiovascular disorder (e.g., acute coronary syndromes, stroke, or diabetes mellitus), vasculopathies (e.g., malaria, disseminated intravascular coagulation), or a combination of two or more thereof.

Compositions for determining cell-cell interaction are also described herein. In one aspect, the composition comprises (a) a solid substrate having a surface comprising a fixed monolayer of cells of a first type thereon; and (b) a fluid sample in contact with the surface, wherein the fluid sample comprises cells of a second type.

In some embodiments, the fixed monolayer of cells of the first type can comprise a fixed endothelial cell monolayer. In some embodiments, the cells of the second type in the fluid sample can comprise blood cells such as platelets.

In some embodiments, the fluid sample can comprise a blood sample.

The fixed cell monolayer can comprise fixed cells (e.g., fixed endothelial cells), fixed cell extract(s) (e.g., fixed endothelial cell extract(s)), and/or fixed cell-associated proteins (e.g., fixed endothelial cell-associated proteins) that are adhered to the surface.

In some embodiments, the fixed cell monolayer (e.g., fixed endothelial cell monolayer) can be derived from fixing a cell layer (e.g., an endothelial cell monolayer) that has been grown on the surface for a period of time, e.g., until the cell layer reaches confluence.

The surface with which the fluid sample is in contact can be a surface of any fluid-flowing conduit disposed in a solid substrate. The solid substrate can be any solid substrate that is compatible to the fluid sample and the fixed cell monolayer. Non-limiting examples of the solid substrate include a cell culture device, a microscopic slide, a cell culture dish, a microfluidic device, a microwell, and any combinations thereof.

In one embodiment, the surface can be a wall surface of a microchannel. In one embodiment, the surface can be a surface of a membrane. In some embodiments where the surface is a surface of a membrane, the membrane can be configured to separate a first chamber (e.g., a first microchannel) and a second chamber (e.g., a second microchannel) in a microfluidic device.

In some embodiments, the microfluidic device can be configured to comprise an organ-on-chip device. An exemplary organ-on-chip can comprise a first chamber (e.g., a first microchannel), a second chamber (e.g., a second microchannel), and a membrane separating the first chamber and the second chamber. In these embodiments, a first surface of the membrane facing the first chamber can comprise the fixed cell monolayer (e.g., fixed endothelial cell monolayer) thereon, and a second surface of the membrane facing the second chamber can comprise tissue-specific cells adhered thereon. In some embodiments, the membrane can be replaced or embedded with extracellular matrix proteins (e.g., but not limited to collagen, laminin, etc.). In some embodiments, the membrane can also comprise smooth muscle cells and/or fibroblasts.

For example, in some embodiments, the methods, systems, and/or compositions described herein can be configured to permit a blood cell-comprising fluid sample (e.g., platelet-comprising fluid sample) flowing over a more reliable and physiologically relevant endothelialized surface inflamed by a cytokine, thus mimicking the in vivo endothelium-blood cell (e.g., platelet) crosstalk environment, e.g., in a normal or diseased state. The blood cell (e.g., platelet) dynamics (e.g., adhesion, translocation and/or detachment) can be recorded and quantified, which is not possible with the existing gold standard tests. As the blood cell (e.g., platelet) function/interaction can be reproduced even when the live endothelial cells are fixed, the compositions with a fixed endothelial cell monolayer described herein can be stored under standard laboratory conditions for a period of time (e.g., days or weeks) and still remain functional. Thus, the compositions described herein can be operated near patients' bedside, e.g., in clinics or hospitals, to determine blood cell (e.g., platelet) dysfunction, e.g., for diagnosis of a disease or disorder induced by blood cell (e.g., platelet) dysfunction.

In some embodiments, the compositions described herein can further comprise tissue-specific cells. For example, in some embodiments, a microfluidic device can comprise a first chamber (e.g., a first microchannel), a second chamber (e.g., a second microchannel), and a membrane separating the first chamber and the second chamber, wherein a first surface of the membrane facing the first chamber can comprise a fixed endothelial cell monolayer thereon, and a second surface of the membrane facing the second chamber can comprise tissue-specific cells adhered thereon. A fluid comprising blood cells (e.g., blood or blood substitute) can be introduced into the first chamber such that blood cells can interact with the fixed endothelial cell monolayer. In some embodiments, the fixed endothelial monolayer can be an inflamed or diseased endothelial cell monolayer. By incorporating luminal blood cell fluid transport (e.g., a fluid comprising blood cells such as platelets) over a fixed endothelial cell monolayer and live culture of tissue specific cells, a physiologically relevant in vitro model of blood cell-induced inflammation can be created to probe its pathophysiology and/or to permit drug screening.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 9 is a plurality of representative maximum intensity projection micrographs with fluorescently labeled platelets adhering to a chemopreserved endothelium.

FIG. 10 is a graph that shows platelet coverage when blood is perfused inside a microchannel that is lined with a living or fixed endothelium.

FIG. 11A is a fluorescent micrograph showing fibrin that is formed along with platelet aggregates on a fixed endothelium (scale bar ~200 µm).

FIG. 11B is a fluorescent micrograph showing fibrin that is formed along with platelet aggregates on a fixed endothelium (scale bar ~20 µm).

FIG. 12 is a graph illustrating platelet coverage on a fixed endothelium that is pretreated with TNF-α when blood samples are perfused through a microfluidic device.

FIG. 13 is a graph illustrating light transmission aggregometry of blood samples containing different doses of abciximab using either ADP or collagen as an agonist.

FIG. 14 is a graph illustrating platelet coverage when blood samples containing different doses of the drug abciximab are perfused through collage-coated microfluidic devices.

FIG. 15 is a graph illustrating platelet coverage on a fixed endothelium that has been pretreated with TNF-α when blood samples from healthy donors are perfused through microfluidic devices.

FIG. 16 is a graph illustrating light transmission aggregometry of healthy versus antiplatelet treated blood samples using ADP or collagen as an agonist.

FIG. 17 is a graph illustrating platelet coverage when healthy versus subject blood samples are perfused through collagen-coated microfluidic devices.

FIG. 20 shows fluorescence micrographs depicting a section of an imaged microchannel with platelet accumulation after 4 minutes of laser-induced injury on a mouse cremaster arteriole (scale bar ~µm 25).

FIG. 21 shows fluorescent micrographs of a large section of a vascular chamber with intravascular thrombus formation in collagen (top image), and TNF-α stimulated endothelium in a dose dependent manner (bottom three images).

FIG. 24 is a conceptual schematic of a human lung showing alveoli interacting with neighboring blood vessels during hemostasis or pulmonary dysfunction.

FIG. 25 is a perspective view illustration of a microfluidic device with two compartments separated by a thin porous membrane.

FIG. 26 is a side view illustration of the microfluidic device of FIG. 25.

FIG. 43 shows a representative kymograph of a small section of a channel with an attachment and detachment pattern of platelets on a collagen surface.

FIG. 44 shows a representative kymograph of a small section of a channel with an attachment and detachment pattern of platelets on a vessel that is untreated.

FIG. 45 shows a representative kymograph of a small section of a channel with an attachment and detachment pattern of platelets on a vessel that is TNF-α treated.

FIG. 46 shows a chart shows a coefficient of variance (CV) of a fluorescence signal observed over time at a representative single pixel location of an image time-series of platelet accumulation, as plotted in the kymographs shown in FIGS. 43-45.

FIGS. 54A-54E are images and schematic diagrams of a biomimetic platelet function analyzer (μPFA) according to one or more embodiments described herein. (FIG. 54A) Schematic of the multilayered microfluidic device comprising a first channel and a second channel, wherein the first channel and the second channel are separated by a permeable membrane. The side of the membrane facing the first channel can comprise an endothelium adhered thereto. The other side of the membrane facing the second channel can comprise astrocytes or other cell types of interest. Shear stresses and/or fluid flow (e.g., whole blood or blood flow) can be induced in the first channel. The multilayered microfluidic device can optionally comprise a vacuum channel on one or both sides of the first and the second channel. (FIG. 54B) Picture of one embodiment of a device showing blood passing through it when pulled by a syringe pump. (FIG. 54C) Schematic drawing (top view) of the vascular chamber showing inlet, outlet and optional pressure ports. (FIG. 54D) A fluorescent micrograph of endothelial cells (green/top channel, CD31 staining) and astrocytes (red/bottom channel/GFAP staining) co-cultured in one embodiment of the device described herein. Such device can then be perfused with blood. (FIG. 54E) (left panels) A sectional view of the vascular chamber coated with HUVECs and inflamed with tumor necrosis factor (TNF-α). (right panels) The endothelial ICAM-1 expression is increased with increase in TNF concentration.

FIGS. 65A-65C depict an embodiment of a platelet dynamics assessment device as described herein. FIG. 65A depicts a schematic of the microfluidic device for quantifying platelet dynamics on a living endothelium under flow when cultured within a hollow microchannel (400 μm wide, 100 μm high, 2 cm long). Human whole blood is stored in a reservoir at the inlet (left) and pulled by a syringe pump attached to the outlet (right) at a flow rate of 30 μl/min (shear rate: 750 sec$^{-1}$). Fluorescently tagged platelets that interact with the endothelium are visualized over time within a central region of the long section of the channel using automated microscopy. FIG. 65B depicts a photograph of the microfluidic platelet assessment chip containing 6-channels (bar, 15 mm). FIG. 65C depicts a representative fluorescence micrograph of platelet-rich thrombi that form on the TNF-α treated endothelial surface in this device when whole blood is perfused. The thrombi contain both platelets (red) and fibrin (green) (bar, left: 100 μm, right: 25 μm). A 3-dimensional confocal reconstruction of platelet-rich thrombi formed on the endothelium-lined microfluidic channel, stimulated by cytokine TNF-α can be generated.

FIG. 66A depicts the image acquisition and analysis protocol according to one embodiment described herein. Fluorescent micrographs were acquired every 30 sec for a total of 15 min; 10 (1×10) image tiles were captured at each time step and stitched together to form a panoramic view, resulting in an image time series (K). FIG. 66B depicts fluorescence micrographs of the microchannel when coated with collagen (COL; top) or lined with endothelium (HUVEC; bottom) are shown on the left. Representative image tiles of platelets interacting with the collagen-coated surface (top) or the surface of endothelium stimulated with different doses of TNF-□ (bottom) 10 min after initiating blood flow are shown at the right (bar, 200 μm).

FIG. 67A depicts representative coefficient of variance (CV) maps, produced using the "fire" color map, showing platelet adhesion patterns on a collagen surface (COL) versus endothelial (HUVEC) lined surface stimulated with different doses of TNFα. Color bar indicates the intensity of aggregation/thrombi (white is greatest; blood flow was from left to right; bar, 200 μm). FIG. 67B depicts a graph showing platelet aggregation indices (AI) derived from maps shown in FIG. 67A. The time series stack (K) is projected across time computing the temporal coefficient of variance (CV) at each spatial pixel (M), and the AI is the inter-quartile range (IQR) of M. Note that the unstimulated endothelium does not induce platelet adhesion or thrombus formation, whereas the amount and variability of the aggregation pattern increases in TNFα dose-dependent manner on stimulated endothelial cells; this results in a rise of AI with increasing TNFα dose (0 ng TNFα/ml; 5 ng TNFα/ml; 100 ng TNFα/ml; n=3,**p<0.01).

FIG. 68A depict representative size-adjusted kymographs showing embolization pattern of platelets on a collagen surface (COL) or endothelium (HUVEC) stimulated with different TNFα doses. FIG. 68B depicts a graph showing platelet Embolization Indices (EI) derived from kymographs shown in FIG. 68A. The time series stack (K) was averaged across the width of the channel and a kymograph (a temporal map of platelet dynamics) was generated (N); the EI is the CV of N. Note that, platelets remained adherent to the collagen surface over time and did not translocate, resulting in a low EI. The unstimulated endothelium did not induce translocation and/or embolization of platelet-rich thrombi whereas these dynamical processes increased in a TNFα dose-dependent manner (0 ng TNFα/ml; 5 ng TNFα/ml; 100 ng TNFα/ml; n=3,**p<0.01).

FIG. 69A is a schematic diagram depicting platelet thrombus formation over a natural versus chemopreserved endothelium. In a microchannel covered on all sides with an untreated living endothelium, whole blood flows without clotting (left). In contrast, platelet-rich thrombus forms if the endothelium is prestimulated by a proinflammatory cytokine, such as TNF-α, due to expression of procoagulatory proteins at its surface (right). The responses of blood under flow shown in the figures at the left can be reconstituted using similar microchannels that are lined by a chemically preserved endothelium. FIG. 69B depicts a schematic of one embodiment of the microdevice described herein. The inlet is a blood reservoir (dia. 3.5 mm) and it is pulled via a syringe pump at the outlet (dia. 1.5 mm) connected to tubing (not shown). The dotted region (~2.5 mm×500 µm) is visualized over time using automated fluorescence microscopy. FIG. 69C depicts endothelial engineering on the microchip. Confocal immunofluorescence microscopic images show a section of the microchannel containing adherent HUVECs when viewed from above (left) and in side view (right). The dotted region represents the analyzed area of platelet accumulation (green, VE cadherin; blue, nuclear DAPI; bar, 200 µm). FIG. 69D depicts quantitative analysis of platelet adhesion and aggregation on living vs. chemopreserved endothelial substrate. (Left) The platelet coverage on both living (white bar) and fixed (shaded bar) endothelium increases in a TNF-α dose-dependent manner (n=4). No significant difference in platelet coverage was observed using living versus chemopreserved endothelium. (Right) Representative maximum intensity projection micrographs showing fluorescently labeled platelet-rich thrombi adhering to the chemopreserved endothelium in a TNF-α dose-dependent manner. The statistical analysis was performed using 2-way ANOVA (Sidak's multiple comparison test). (bar, 200 µm). FIG. 69E depicts Tissue Factor (TF, blue) and von Willebrand Factor (vWF, purple) expression on untreated (white bar) vs. stimulated (shaded bar) chemopreserved endothelial substrate. Error bars, standard error of mean (s.e.m.). *P<0.05 in all graphs.

FIG. 70A shows that the platelet coverage over the TNF-α stimulated chemopreserved endothelium decreases with increase in abciximab drug concentration (n=4). The statistical analysis was performed using 1-way ANOVA (Sidak's multiple comparison test). FIG. 70B shows that when blood is perfused at a shear of 750 sec$^{-1}$ on a collagen microfluidic device, there is an insignificant decrease in platelet adhesion and aggregation with increase in abciximab dosage (n=3) whereas, (as shown in FIG. 70C) platelets aggregate in the presence of ADP (white bar) and collagen (shaded bar) as agonists, only when control blood is used. In the presence of drug, no aggregation is observed on the light transmission aggregometry (n=5). (For FIGS. 70B and 70C, N.S=non-significant; statistical analysis based on 1-way ANOVA (Sidak's multiple comparison test)). FIG. 70D shows that an untreated chemopreserved endothelium (white bar) is quiescent for both healthy donors and patients who are on chronic use of aspirin alone or both aspirin and clopidogrel, but in comparison to healthy donors, patients result in significantly lower platelet coverage on the TNF-α stimulated chemopreserved endothelium (shaded bar)(n=11). The statistical analysis was performed using one-way ANOVA (Sidak's multiple comparison test). FIG. 70E shows that blood from subjects who are on antiplatelet therapy, showed insignificant difference in aggregation compared to healthy controls using a collagen coated microfluidic device (n=11, p=0.4493—non-significant based on unpaired t-test results (two-tailed)). FIG. 70F shows that blood from subjects who are on antiplatelet therapy, exhibited significantly less aggregation compared to healthy controls using a light transmission aggregometry with ADP (white bar) and collagen (shaded bar) as agonists. (n=11, *: P<0.05 based on 2-way ANOVA analysis (Sidak's multiple comparison test)). *P<0.05 in all graphs. N.S.=non-significant.

FIG. 71A depicts confocal immunofluorescence microscopic images showing the entire length of the microchannel containing adherent human umbilical cord endothelial cells (HUVECs) shown when viewed from above (Top) and in cross-sectional views (Bottom) (green, VE cadherin; blue, nuclear DAPI; bar, 300 µm). To generate a 3-dimensional confocal reconstruction of endothelium-lined microfluidic channel, sequential images obtained along the microchannel containing adherent human umbilical cord endothelial cells (HUVECs) were acquired using Leica SP5X MP inverted confocal microscope. The virtual volume was processed using Huygens deconvolution software and rendered with Imaris (Green, VE cadherin; blue, nuclear DAPI). FIG. 71B depicts a graph (left) and immunofluorescence microscopic views of the cultured endothelium stained for intercellular adhesion molecule-1 (ICAM-1) at left or F-actin at right, showing dose-dependent activation of ICAM-1 (left images) when stimulated with tumor necrosis factor alpha (TNF-α)(green, ICAM-1 or F-actin; blue, DAPI; bar, 300 µm).

FIG. 73A depicts area averaged platelet adhesion rate on a surface calculated using automated Otsu image thresholding algorithm. The percentage area covered was calculated as the ratio of number of pixels with the value of unity to the size of the binary image and plotted against time. The dotted line is the linear regression curve fit and the adhesion rate is the slope of the regression line. FIG. 73B depicts area-averaged platelet adhesion rate. n=3,**p<0.01

FIG. 76 is a set of fluorescent images showing platelet-rich thrombus formation in the microfluidic device after blood perfusion. Fluorescent micrograph shows fibrin (green) is formed along with platelet aggregates (red) in collagen and TNF-α (5 ng/ml) stimulated chemopreserved endothelium after recalcified citrated whole blood is perfused through the device. The platelet aggregates are small and more uniformly distributed over the collagen compared to the inflamed endothelial surface. (bar, 100 μm)

Figure 1:
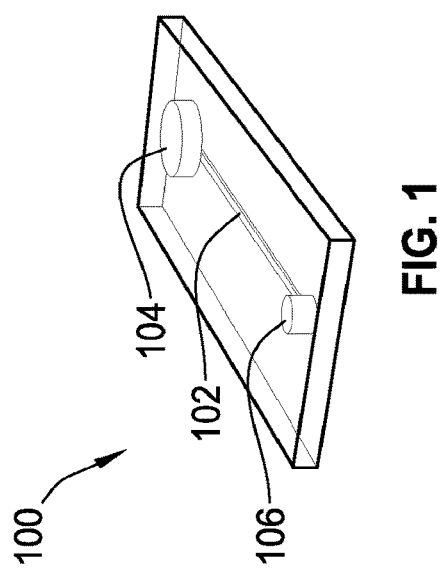
FIG. 1 is a perspective illustration of a microfluidic device.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

As used herein, the term "monolayer" refers to a single layer of cells on a growth surface, on which no more than 10% (e.g., 10%, 9%, 8%, 7%, 6%, 5%, 4%, 3%, 2%, 1%, or 0%) of the cells are growing on top of one another, and at least about 90% or more (e.g., at least about 95%, at least 98%, at least 99%, and up to 100%) of the cells are growing on the same growth surface. In some embodiments, all of the cells are growing side-by side, and can be touching each other on the same growth surface. The condition of the cell monolayer can be assessed by any methods known in the art, e.g., microscopy, and/or immunostaining for cell-cell adhesion markers. In some embodiments where the fixed cell monolayer comprises a fixed endothelial cell monolayer, the condition of the endothelial cell monolayer can be assessed by staining for any art-recognized cell-cell adhesion markers in endothelial cells, e.g., but not limited to VE-cadherin.

In some embodiments, the monolayer can be substantially confluent. As used herein, the term "confluent" generally indicates that the cells have formed a coherent monocellular layer on a growth surface, so that virtually all the available growth surface is used. As used herein, the term "substantially confluent" indicates that most of the cells growing on the same surface are in contact with each other around the cell periphery, and interstices can remain, such that over about 70% or more, including, e.g., over about 80%, over about 90%, over about 95% or more, and up to 100%, of the available growth surface is used. The term "available growth surface" as used herein refers to sufficient surface area to accommodate a cell. Thus, small interstices between adjacent cells that cannot accommodate an additional cell do not constitute "available growth surface." Accordingly, in some embodiments, the fixed cell monolayer (e.g., fixed endothelial cell monolayer) can be derived from fixing a layer of cells of the first type (e.g., an endothelial cell monolayer) that has been grown on the surface for a period of time. In some embodiments, the period of time can vary with degree of confluence, cell proliferation rate, number of initially seeded cells, number of cell culture passages, or a combination thereof. For example, the layer of cells of the first type (e.g., an endothelial cell monolayer) can grow on the surface until it is substantially confluent and is then subjected to a fixation treatment as described herein. In some embodiments where the layer of cells of the first type comprises endothelial cells, the endothelial cell culture can be cultured for at least about 24 hours or longer to reach an intact and confluent monolayer.

In some embodiments, the monolayer can be exposed to or stimulated by an agent, e.g., a condition-inducing agent, prior to fixation. In these embodiments, the cells in the monolayer can overgrow and form plexiform lesions, prior to fixation.

The fixed cell monolayer (e.g., fixed endothelial cell monolayer) can be derived from a cell line (e.g., primary cell lines), stem cells, or cells collected from a subject. In some embodiments, target cells to be cultured on the surface can be collected from a subject. For example, to form a fixed endothelial cell monolayer, endothelial cells can be collected from a subject. In some embodiments, endothelial cells can be derived from stem cells or induced pluripotent stem cells. For example, skin fibroblasts can be collected from a subject and reprogrammed to form pluripotent stem cells, which are then differentiated into subject-specific target cells (e.g., endothelial cells) to form a fixed cell monolayer (e.g., a fixed endothelial cell monolayer). Methods to derive different types of differentiated cells from induced pluripotent stem cells are known in the art. For example, vascular endothelium can be derived from induced pluripotent stem cells using the methods as described, e.g., in Adams et al., Stem Cell Reports (2013) 1:105-113.

The fixed cell monolayer (e.g., fixed endothelial cell monolayer) can be derived from cells of any condition or state (e.g., but not limited to wild-type, healthy state, mutant, disease-specific, and stimulated state). In some embodiments, the fixed cell monolayer (e.g., fixed endothelial cell monolayer) can be derived from healthy cells or wild-type cells. As used herein, the term "healthy" refers to a state without any symptoms of any diseases or disorders, or not identified with any diseases or disorders, or not on any physical, chemical and/or biological treatment, or a state that is identified as healthy by skilled practitioners based on microscopic examinations. As used herein, the term "wild-type" refers to a natural state without any genetic manipulation.

In some embodiments, the fixed cell monolayer (e.g., fixed endothelial cell monolayer) can be derived from disease-specific cells. As used herein, the term "disease-specific" refers to a state of cells that recapitulates at least one characteristic associated with a disease, disorder or an injury, or different stages thereof. In some embodiments, the term "disease-specific" can refer to a specific stage or grade of a disease, disorder or an injury. Examples of diseases, disorders, or injuries can be related to any organ or tissue, e.g., but not limited to, blood vessel, lung, brain, nerve network, blood-brain-barrier, vascular, kidney, liver, heart, spleen, pancreas, ovary, testis, prostate, skin, eye, ear, skeletal muscle, colon, intestine, and esophagus. In some embodiments where the fixed cell monolayer comprises a fixed endothelial cell monolayer, the endothelial cells can recapitulate at least one characteristic associated with a vascular and/or inflammatory disease or disorder.

The disease-specific cells can be either obtained from a biopsy of a patient carrying the disease, disorder or an injury, or inducing a healthy cell with a condition-inducing agent that is known to induce the cell to acquire at least one characteristic associated with the disease, disorder, or injury, prior to a fixation treatment. For example, a condition-inducing agent can comprise an environmental or physical agent such as radiation; a chemical or biological agent, e.g., but not limited to, cytokines described herein and/or pathogens; a molecular agent (e.g., but not limited to a pathogen-derived toxin such as lipopolysaccharides (LPS), and/or a candidate drug/compound that is known to cause endothelial activation or thrombotic toxicity), or a combination of two or more thereof.

In some embodiments, the fixed cell monolayer (e.g., fixed endothelial cell monolayer) can be derived from stimulated cells. As used herein, the term "stimulated" refers to a state of cells that are responsive to a condition-inducing agent exposed to them. As used herein, the term "condition-inducing agent" refers to any agent that can cause a cell to display a phenotype that is deviated from a basal state (without exposure to the condition-inducing agent). The condition-inducing agent can provoke a beneficial or adverse effect such as cytotoxic effect on the cells. Examples of a condition-inducing agent can include, but are not limited to, environmental or physical agents such as radiation (e.g., gamma radiation) and mechanical stress (e.g., fluid shear stress); proteins, peptides, nucleic acids, antigens, cytokines, growth factors, toxins, cells (including prokaryotic and eukaryotic cells such as virus, bacteria, fungus, parasites, and mammalian cells), particulates (e.g., smoke particles or asbestos), particles (e.g., nanoparticles or microparticles, magnetic particles), small molecules, biologics, and any combinations thereof.

In some embodiments where the fixed cell monolayer comprises a fixed endothelial cell monolayer, the condition-inducing agent added to the endothelial cell monolayer prior to fixation can comprise an inflammation-inducing agent that induces endothelium inflammation and/or activation. The inflammation-inducing agent can comprise one or a combination of two or more of the following: physical conditions (e.g., lack of oxygen, and disturbed flow patterns), chemical (e.g., glucose levels, environmental pollutants), biochemical (e.g., inflammatory molecules such as interleukins, interferons, TNF-superfamily molecules), biological, human cell derived (complex mixtures), or biological, non-human cell derived (e.g., bacteria, or factors secreted by bacteria). In some embodiments, the inflammation-inducing agent can comprise at least one or more (e.g., at least two or more) proinflammatory cytokines such as IL-6, IL-2, IL-10, sCD40L, interleukins and interferons, which can be applied to produce endothelial activation and inflammation that are involved in platelet function, activation and aggregation. Other factors such as lipopolysaccharide (LPS), toxins (Shiga toxin etc.), bacteria, viruses, nanoparticles, antibodies and drug candidates can also be used as inflammation-inducing agents to stimulate the endothelium. In some embodiments, the inflammation-inducing agent can comprise glucose. For example, the surface comprising the fixed endothelial cell monolayer can be configured to provide highly fluctuating levels of glucose to stimulate a "diabetic" surface. In some embodiments, complex mixtures of soluble factors from tumor cells, and/or activated white blood cells can be used as the inflammation-inducing agents to activate the endothelium. In some embodiments, the inflammation-inducing agents can comprise temporary co-culture with tumor cells and/or white blood cells to induce endothelial activation.

As used herein, the term "fixed," "fixation," or "fixing" means that cell-associated components or materials, including, e.g., but not limited to whole cells, cell fragments, intracellular proteins, extracellular proteins (e.g., secreted proteins, cell surface receptors), nucleic acid molecules, and/or cytoskeleton, are treated with a fixative agent or composition, resulting in at least a partial stabilization or preservation of their molecular position, histological structure, and/or molecular function. Upon fixation, whole cells are not alive anymore but proteins and/or nucleic acid of the cells and cell-associated proteins and/or nucleic acid present in the cell monolayer remain stable and functional (e.g., ability to induce a response in other live cells). Thus, cell fixation can provide spatial heterogeneity and expressions of proteins and/or nucleic acid molecules that would be expected in live culture and/or in vivo. In some embodiments, a fixation agent or composition can result in at least about 50% or more (including, e.g., at least about 60%, at least about 70%, at least about 80%, at least about 90%, at least about 95%, at least about 98%, or more or up to 100%) stabilization or preservation of the cell-associated components' or materials' molecular position, histological structure, and/or molecular function.

Various methods for fixing cells that are adhered to a surface are known in the art and can be used herein to generate a fixed cell monolayer. In some embodiments, cell fixation methods can be selected to keep whole cell intact. For example, in some embodiments, the cell monolayer (e.g., endothelial cell monolayer) can be physically fixed by drying and/or dehydration. For example, in some embodiments, the cell monolayer (e.g., endothelial cell monolayer) can be physically fixed by exposing the cell monolayer to air, and/or washing the cell monolayer with a drying solvent, e.g., alcohol (e.g., ethanol) and acetone, or a solvent that removes water and/or lipids. In some embodiments, the cell monolayer (e.g., endothelial cell monolayer) can be fixed with a chemical fixative. Non-limiting examples of chemical fixatives include formaldehyde, paraformaldehyde, formalin, glutaraldehyde, mercuric chloride-based fixatives (e.g., Helly and Zenker's solution), precipitating fixatives (e.g., ethanol, methanol, and acetone), dimethyl suberimidate (DMS), Bouin's fixative, and a combination of two or more thereof. In one embodiment, the chemical fixative for fixing the cell monolayer (e.g., endothelial cell monolayer) can comprise paraformaldehyde. Accordingly, in some embodiments, the fixed cell monolayer (e.g., endothelial cell monolayer) can be derived by fixing whole cells adhered on a surface.

In some embodiments, the cell layer (e.g., endothelial cell monolayer) can be fixed with a fixative agent or composition comprising paraformaldehyde.

Additionally or alternatively, cell fixation methods can be selected to remove a portion of cell components and fix the remaining cell components. For example, in some embodiments, the cell monolayer (e.g., endothelial cell monolayer)

can be fixed with a decellularization solvent. The decellularization solvent is a solvent that partially or completely removes or extracts cell membranes and/or soluble components but stabilizes molecular configuration, molecular function, and molecular position of surface membrane proteins (e.g., membrane protein receptors), insoluble components, and/or cytoskeleton of a cell. Methods for fixing cells by membrane removal or extraction are known in the art, e.g., as described in Ben-Ze'ev et al., Cell (1979) 17: 859-865; Pourati et al., Am J Physiol. (1998) 274: C1283-1289; Sims et al., J Cell Sci. (1992) 103: 1215-1222; and Fey et al., J Cell Biol. (1984) 98: 1973-1984. F or example, in some embodiments, the decellularization solvent can comprise an aqueous solution comprising a detergent (e.g., polysorbate surfactants such as Tween 20, and/or a nonionic surfactant such as Triton X-100; glycosides such as saponins) and/or a high pH solution (e.g., an alkaline solution such as ammonium hydroxide). Accordingly, in some embodiments, the fixed cell monolayer can be derived from fixing cell extract and/or cell-associated proteins that are adhered to the surface.

In some embodiments, an additive can be added to a fixative agent or composition to render cells permeable to ligands which bind to intracellular moieties. Binding of ligands (e.g., but not limited to, antibodies and detectable labels) to intracellular moieties can be desired for purposes of visualizing, detecting, or isolating the cells after they have been preserved. Additives that increase the permeability of cell membrane and/or nuclear envelopes are known in the art. For example, the organic solvent acetone, methanol, and/or ethanol can increase the permeability of cell membrane when preservation of protein and/or nucleic acid moieties is/are desired.

In some embodiments, an additive can be added to a fixative agent or composition to keep cells isosmotic which helps preservation. For example, sugars such as sucrose and/or buffered solutions can be added to keep cells isosmotic.

A skilled artisan can optimize the concentrations of a fixative agent or composition added to the cell monolayer (e.g., an endothelial cell monolayer). Typical concentrations of the fixative agent or composition can range from about 1% (v/v) to about 10% (v/v), and they can vary with the strength of the selected fixative agent or composition. For example, when paraformaldehyde is used to fix the cell monolayer (e.g., endothelial cell monolayer), the concentration of the paraformaldehyde can range from about 1% (v/v) to about 8% (v/v). In one embodiment, the cell monolayer (e.g., endothelial cell monolayer) can be fixed with paraformaldehyde at a concentration of about 4%.

The temperature at which the cells are fixed can range from about 0° to about room temperature. In some embodiments, the fixation temperature can vary from about 0° C. to about 10° C. In some embodiments, the fixation temperature can vary from about 0° C. to about 4° C. In one embodiment, the fixation temperature can be about 4° C.

The fixation time duration (i.e., time elapsing before the cell layer (e.g., endothelial cell monolayer) is fixed once a fixative agent or composition is added) can vary with a number of factors, including, e.g., but not limited to types, temperature and/or concentration of the selected fixative agent or composition. For example, the higher the concentration of a fixative agent or composition is used, the shorter the fixation time duration can be. For example, when paraformaldehyde at a concentration of about 4% is used to fix the cell monolayer (e.g., an endothelial cell monolayer), the fixation time duration can range from about 15 minutes to about 30 minutes. In one embodiment, the fixation time duration can be about 20 minutes.

The inventors have showed that once the cell monolayer (e.g., endothelial cell monolayer) is fixed, the fixed cell monolayer (e.g., endothelial cell monolayer) can be stored for a period of time without significantly reducing its applicability, e.g., to determine platelet dynamics analysis, as compared to a freshly fixed cell monolayer or a fixed cell monolayer that has been stored for a shorter period of time. Accordingly, in some embodiments, the surface comprising the fixed cell monolayer (e.g., fixed endothelial cell monolayer) can have been stored for a period of time prior use. In some embodiments, the fixed cell monolayer (e.g., fixed endothelial cell monolayer) can be stored at a non-freezing temperature. For example, in some embodiments, the fixed cell monolayer (e.g., fixed endothelial cell monolayer) can be stored at room temperature. In some embodiments, the fixed cell monolayer (e.g., fixed endothelial cell monolayer) can be stored at a temperature of about 4° C. or lower. In some embodiments, the fixed cell monolayer (e.g., fixed endothelial cell monolayer) can be stored at a temperature of about 4° C.-10° C.

The period of time to store the fixed cell monolayer (e.g., fixed endothelial cell monolayer) without significantly reducing its applicability (i.e., shelf-life of the surface comprising a fixed cell monolayer (e.g., a fixed endothelial cell monolayer)) can vary with the selected storage temperature. In some embodiments, the period of time (shelf-life) can be at least about 1 day or longer, including, e.g., at least about 2 days, at least about 3 days, at least about 4 days, at least about 5 days or longer. In some embodiments, the period of time (shelf-life) can be at least about 5 days or longer. In some embodiments, the period of time (shelf-life) can be at least about 1 week or longer. In some embodiments, the period of time (shelf-life) can be at least about 2 weeks or longer, including, e.g., at least about 3 weeks, at least about 4 weeks or longer.

In some embodiments where the fixed cell monolayer comprises a fixed endothelial cell monolayer, the fluid sample can comprise a blood sample, a serum sample, a plasma sample, a lipid solution, a nutrient medium, or a combination of two or more thereof. In some embodiments, the fluid sample can comprise at least one type of blood cells, e.g., red blood cells, white blood cells, and platelets. In one embodiment, the fluid sample can comprise platelets, and no red blood cells. In this embodiment, the method described herein can further comprise removing red blood cells from the fluid sample (e.g., a blood sample) prior to flowing the blood sample over the surface.

Without wishing to be bound by theory, platelet function may depend upon the presence of $Ca^{2+}$ and $Mg^{2+}$. Thus, for a fluid sample comprising a citrated blood sample (where citration of a blood sample generally quenches the free $Ca^{2+}$ and $Mg^{2+}$ ions to prevent blood coagulation), addition of $Ca^{2+}$ (e.g., calcium chloride) and $Mg^{2+}$ (magnesium chloride) to the fluid sample can help restore the native physiological state of the platelet, e.g., to allow platelet aggregation or coagulation. Thus, in some embodiments, the citrated blood sample can be added with $Ca^{2+}$ (e.g., calcium chloride) and $Mg^{2+}$ (magnesium chloride) such that the final concentrations reach about 4-12 mM and 3-10 mM, respectively. However, when a blood sample is collected in the presence of thrombin blockers to prevent blood coagulation (e.g., but not limited to heparin, hirudin, EDTA, PPACK and/or any other anticoagulant), the addition of $Ca^{2+}$ (e.g., calcium chloride) and $Mg^{2+}$ (magnesium chloride) may not be required.

In some embodiments, the surface can be a surface of a fluid-flowing conduit or passageway disposed in a solid substrate. In some embodiments, the solid substrate can comprise a cell or tissue culture device, including, e.g., but not limited to a transwell, a microwell, a microfluidic device, a bioreactor, a culture plate, or any combinations thereof.

In some embodiments, the surface can be a solid surface. For example, in one embodiment, the solid surface can be a wall surface of a fluid channel, e.g., a microfluidic channel.

In some embodiments, the surface can be a porous or gas-permeable surface. For example, in one embodiment, the surface can be a surface of a gas-permeable membrane. In some embodiments, the membrane can be configured to separate a first chamber (e.g., a channel or a compartment) and a second chamber (e.g., a channel or a compartment) in a cell or tissue culture device.

In some embodiments, the surface can be disposed in a microfluidic device. In one embodiment, the microfluidic device can be an organ-on-a-chip device. Examples of various organ-on-a-chip devices, e.g., as described in International Patent Application Nos: WO 2010/009307, WO 2012/118799, WO 2013/086486, WO 2013/086502, and in U.S. Pat. No. 8,647,861, the contents of each of which are incorporated herein by reference in their entireties, can be utilized to perform the methods described herein. In one embodiment, the organ-on-a-chip device can comprise a first channel and a second channel separated by a membrane. The membrane can be porous (e.g., permeable or selectively permeable), non-porous (e.g., non-permeable), rigid, flexible, elastic, or any combination thereof. In some embodiments, the membrane can be porous, e.g., allowing exchange/transport of fluids (e.g., gas and/or liquids), passage of molecules such as nutrients, cytokines and/or chemokines, cell transmigration, or any combinations thereof. In some embodiments, the membrane can be non-porous. In some embodiments, a first surface of the membrane facing the first channel comprises a fixed cell monolayer (e.g., a fixed endothelial cell monolayer) adhered thereon. In some embodiments, a second surface of the membrane facing the second channel can comprise tissue-specific cells adhered thereon. In some embodiments, the membrane can be replaced or embedded with extracellular matrix proteins (e.g., but not limited to collagen, laminin, etc.). In some embodiments, the membrane can also comprise smooth muscle cells and/or fibroblasts.

By detecting interaction between cells (e.g., blood cells such as platelets) in the fluid sample and the fixed cell monolayer (e.g., fixed endothelial cell monolayer), temporal and/or spatial dynamics of the cells in the fluid sample interacting with each other and/or to the fixed cell monolayer can be measured. In some embodiments, the measured temporal and/or spatial dynamics of cell interaction measured can comprise cell adhesion, cell detachment, cell translocation, and cell embolization/aggregation. As used herein, the term "cell adhesion" refers to spatial and/or temporal adhesion of cells (e.g., platelets) to each other and/or to a fixed cell monolayer (e.g., fixed endothelial cell monolayer) when the fluid sample flows over the fixed cell monolayer (e.g., fixed endothelial cell monolayer). As used herein, the term "cell detachment" refers to spatial and/or temporal detachment of cells from cell-cell binding (e.g., between platelets) and/or from the fixed cell monolayer (e.g., fixed endothelial cell monolayer) when the fluid sample flows over the fixed cell monolayer (e.g., fixed endothelial cell monolayer). As used herein, the term "cell translocation" refers to temporal movement of cells (e.g., platelets) from one position to another when the fluid sample flows over the fixed cell monolayer (e.g., fixed endothelial cell monolayer). As used herein, the term "cell embolization/aggregation" refers to spatial and/or temporal binding of cells (e.g., platelets) to form an aggregate, clump, or embolic material when the fluid sample flows over the fixed cell monolayer (e.g., fixed endothelial cell monolayer).

In some embodiments, the measured temporal and/or spatial dynamics of cell interaction can comprise binding dynamics of the cells (e.g., blood cells such as platelets) to the fixed cell monolayer (e.g., fixed endothelial cell monolayer), binding dynamics of the cells (e.g., blood cells such as platelets) to each other, or a combination thereof.

Depending on cell detection methods, the cells (e.g., blood cells such as platelets) in the fluid sample can be label-free or labeled. In some embodiments, the cells (e.g., blood cells such as platelets) can be label-free. In these embodiments, phase-contrast or brightfield microscopy can be used to detect the cells when they are flowing across the surface comprising a fixed cell monolayer. In some embodiments where the methods described herein are used for platelet function analysis, the label-free platelets can be detected by phase-contrast or brightfield microscopy. In some embodiments where red blood cells may obscure the view, the fluid sample can be pre-treated to remove red blood cells, or formation of platelet aggregates can be analyzed by an indirect method, e.g., assessment of red blood cell streamlines around a growing platelet aggregate. Methods for analyzing formation of an aggregate in a label-free manner are known in the art, including, for example, but not limited to microscopy and local impedance spectroscopy (a physical, electrophysiological measurement).

In some embodiments, the cells (e.g., blood cells such as platelets) can be labeled. As used herein, the term "labeled" refers to a cell being manipulated to express or carry a detectable label, e.g., to facilitate detection of the presence or absence of the cell. As used herein, the term "detectable label" refers to a composition capable of producing a detectable signal indicative of the presence of a target. Detectable labels suitable for the detection methods that provide spatial and/or temperate information about cell dynamics (e.g., cell adhesion, cell detachment, cell translocation, and/or cell embolization/aggregation) described herein can include any composition detectable by spectroscopic, photochemical, biochemical, immunochemical, electrical, magnetic, optical, chemical means, or a combination of two or more thereof. In some embodiments, the detectable label can encompass any imaging agent (e.g., but not limited to, a fluorophore, a nanoparticle, and/or a quantum dot).

An exemplary detectable label can comprise a fluorescent label or fluorophore. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

In some embodiments, the detectable label can be conjugated to a cell-targeting moiety. For example, platelets can be labeled with a detectable label that is conjugated to a platelet-targeting moiety. Examples of platelet-targeting moieties include, but are not limited to, platelet endothelial cell adhesion molecule (e.g., CD31), antibodies to platelet surface protein (e.g., CD41, CD61, and/or CD42b).

Any art-recognized cell detection methods can be used to detect interaction between cells in the fluid sample and the fixed cell monolayer. In some embodiments, an imaging-based method can be used. An exemplary imaging-based method can comprise time-lapse microscopy, wide-field holography, stereomicroscopes, cameras, compact mobile devices, or any combinations thereof.

The fluid sample can be flowed over the surface comprising a fixed cell monolayer (e.g., fixed endothelial cell monolayer) at a pre-determined shear rate or flow rate. For example, the fluid sample can be flowed over the surface at a flow rate that generates a physiological or pathological wall shear rate. In some embodiments, the fluid sample can be flowed over the surface at a flow rate that generates a physiological or pathological arterial shear rate. For example, the physiological or pathological wall shear rate can range from about 50 $sec^{-1}$ to about 10,000 $sec^{-1}$. In some embodiments, the physiological or pathological shear rate can range from about 100 $sec^{-1}$ to about 1,000 $sec^{-1}$. In some embodiments, the physiological or pathological shear rate can range from about 200 $sec^{-1}$ to about 900 $sec^{-1}$. In one embodiment, the physiological or pathological shear rate can be about 750 $sec^{-1}$. Various methods to flow a fluid sample over a surface in a chamber are known in the art. For example, the fluid transport over the surface comprising a fixed cell monolayer (e.g., fixed endothelial cell monolayer) can be achieved by syringe pump, capillary driven flow, gravitational flow and/or pressure-driven flow.

The fixed cell monolayer (e.g., fixed endothelial cell monolayer) and the fluid sample can be derived from the same subject or from different sources.

As used herein, the term "reactive fluid sample cells" refers to cells from a fluid sample having a higher frequency (e.g., by at least about 30% or more) of binding with each other (e.g., aggregation), and/or with a fixed cell monolayer (e.g., adhesion, detachment, and translocation), as compared to control cells (e.g., healthy cells, or nonstimulated cells).

As used herein, the terms "treat" or "treatment" or "treating" refers to both therapeutic treatment and prophylactic or preventative measures, wherein the object is to prevent or slow the development of the disease, such as slow down the development of a blood cell-induced disease or disorder, or reducing at least one effect or symptom of the blood cell-induced disease or disorder. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "platelet dysfunction" refers to abnormal platelet behavior, as compared to healthy platelets. In one embodiment, platelet dysfunction can be caused by increased adhesion to an endothelium (e.g., by at least about 30% or more), as compared to healthy platelets. In one embodiment, platelet dysfunction can be caused by abnormal detachment from other platelets and/or from an endothelium (e.g., by at least about 30% or more), as compared to healthy platelets. In one embodiment, platelet dysfunction can be caused by abnormal translocation (e.g., by at least about 30% or more), as compared to healthy platelets. As used herein, the term "abnormal translocation" refers to a platelet that gets activated in one location and deposits at another location to form a clot or cause inflammation response. For example, thromboembolism can be considered as abnormal translocation. In one embodiment, platelet dysfunction can be caused by increased aggregation between platelets (e.g., by at least about 30% or more), as compared to healthy platelets.

Generally, in reference to one aspect, a simple microfluidic device is lined by a chemically preserved human endothelium that retains its ability to support thrombus formation and platelet adhesion as blood flows through its channels at an arterial shear rate. This biomimetic device demonstrates the potential practical value for laboratory and point-of-care settings by showing that it can be more rapid and reliable than standard aggregometry or similar collagen-coated microfluidic devices.

Generally, in reference to another aspect, a lung-on-a-chip microfluidic device reconstitutes critical functional aspects of intravascular pulmonary thrombus formation and platelet-endothelial dynamics in the vicinity of an endotoxin or cytokine stimulated primary human alveolar epithelium. The lung-on-a-chip microfluidic device is perfused with human whole blood in a bioengineered vascular lumen. Additionally, based on inherent dynamic complexity and spatiotemporal heterogeneity in the way platelets interact with the vessel wall and initiate thrombus formation, a method is directed to a large-scale real-time fluorescence image acquisition and a statistical algorithm for quantifying platelet-endothelial dynamics during endothelial dysfunction.

Combining the supporting quantitative analysis and the in vitro organ-level functional microfluidic device, the pulmonary thrombosis-on-chip model has been extended to evaluate the cytoprotective affect of a potential protease activator receptor ("PAR-1") inhibitor, termed parmodulin 2 ("PM2"). Thus, the results lead to the proposition that this inhibitor is a potential anti-thrombotic and anti-inflammatory therapeutic drug for human patients to treat disorders that lead to acute lung thrombosis.

I. FIXED CELLS—MATERIALS AND METHODS

A. Microfluidic Device Design and Treatment

By way of example, a microfluidic device is fabricated using photolithography followed by soft lithography with polydimethysiloxane ("PDMS"). According to this example, six microfluidic devices are placed on a single PDMS mold of the size of a standard glass slide, e.g., 75×25 millimeters ("mm"). The microfluidic devices are first exposed to oxygen plasma for 30 seconds using, for example, a PE-100 benchtop plasma system from Plasma Etch. Then, the microfluidic devices are treated with 1% (3-aminopropyl)-trimethoxysilane ("APTMS"), from Sigma, in 100% anhydrous ethanol for ten minutes. After subsequent rinsing with 70% and 100% ethanol, the microfluidic devices are dried and type I collagen from rat tail, e.g., 100 micrograms/milliliter ("µg/ml") from Corning, is introduced in microchannels of the microfluidic devices.

The microfluidic devices are left overnight at 37° C. in a 5% carbon dioxide ("$CO_2$") incubator, after which they are rinsed with Endothelial Growth Medium-2 ("EGM-2") from Lonza. Human Umbilical Vein Endothelial Cells ("HUVEC") from a mixed donor, by Lonza, are kept in culture and suspended at 12.5 million cells/milliliter ("mL") in EGM-2, after confluence. The suspension is introduced into the collagen-coated microchannels, after which the microfluidic devices are incubated upside down for 20 minutes. A fresh HUVEC suspension is then introduced in the microchannels, after which the microfluidic devices are incubated for eight hours to promote cell attachment across the channel. The microchannels are, then, rinsed with EGM-2, sometimes containing a freshly prepared solution of tumor necrosis factor ("TNF-α"), which is a recombinant from E. coli from Sigma. Antibodies against intercellular adhesion molecule-1 ("ICAM-1") and vascular adhesion molecule-1 ("VCAM-1"), tissue factor (from Santa Cruz), VWF (from Abcam) and VE-Cadherin (from Santa Cruz) were perfused into the microfluidic devices after fixing the endothelium with 2% paraformaldehyde for ten minutes, incubating the endothelium for three hours, and counterstaining with a secondary fluorescent IgG antibody for three hours.

B. Blood Samples and Human Subjects

Human blood (e.g., received from Research Blood Components, Cambridge, Mass.) is acquired in 3.2% sodium citrate tubes and is used within 5 hours of blood draw, to prevent pre-analytical effects on platelet function. Institutional review board ("IRB") approval is obtained for use of discarded blood samples. Subjects are selected from among patients who re taking antiplatelet medication. A total of 11 samples are used for analysis, from which 8 patients re on aspirin alone and 3 re on aspirin and clopidogrel (Plavix).

C. Blood Perfusion 500 microliters ("μL") of whole blood are pipetted into a fluid reservoir fitted to one end of a microchannel. Platelets are labeled with human CD41-PE antibody (e.g., 10 μL/mL from Invitrogen) that is directly added to the blood samples and incubated at room temperature for 10 minutes. Fluorescently labeled fibrinogen (e.g., 10 μg/mL from Life Sciences) is added, if required. Blood is pulled through the device (e.g., 30 μL/min) via tubing at an outlet using a syringe pump (e.g., PHD Ultra™ CP, Harvard Apparatus), resulting in an arterial shear rate of 750 s$^{-1}$. After two minutes, blood is supplemented with 100 millimolars ("mM") calcium ("CaCl$_2$") and 75 mM magnesium ("MgCl$_2$") to support coagulation-activated blood clotting (e.g., 100 μL/mL).

D. Image Acquisition and Analysis

Platelets are visualized using time-lapse fluorescence imaging (e.g., 20×, NA 0.4). A time series of a 10-frame panorama (e.g., 6 mm long×0.665 mm wide region of a microchannel), at a lapse of every 30 seconds is recorded. The resulting image stack is maximum intensity projected along time, thresholded, segmented, and cropped to a central 200 microns ("μm") of the channel width for analysis. Finally, platelet coverage is computed from the binary image as the ratio of bright pixels to the total number of pixels in the image.

E. Light Transmission Aggregometry ("LTA")

The LTA is performed in accordance with manufacturer instructions. For example, the LTA uses adenosine diphosphate ("ADP") 10 μM and collagen 2 μg/mL from Chrono-Log.

F. Statistical Analysis

All data is presented as mean±standard error (SEM). Two-tailed P values are obtained from a statistical t-test or one way ANOVA using GraphPad Prism V6.

II. FIXED CELLS—RESULTS AND DISCUSSION

A. Formation and Evaluation of a Chemically Preserved Endothelium

In reference to FIG. 1 and the above example, a microfluidic device 100 is engineered that contains a rectangular microchannel 102. By way of example, the microchannel 102 is 400 μm wide, 100 μm high, and 2 centimeters ("cm") long. The microfluidic device 100 has a blood inlet reservoir 104, followed by the straight microchannel 102 that ends at an outlet 106. A syringe pump is attached to the outlet 106 to pull the blood from the microchannel 102.

Figure 2:
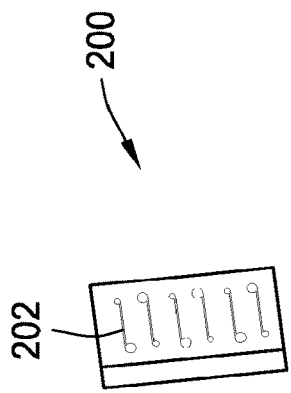
FIG. 2 is top view illustration of a single microfluidic chip with a plurality of microfluidic devices.

In reference to FIG. 2, a microfluidic device 200 is made of PDMS and has six similar and independent microchannels 202 that are provided on a single chip. The microchannels 202 are similar to or identical with the microchannel 102 illustrated in FIG. 1. According to one example, the chip 200 is 15 cm long and is fabricated on a glass slide.

Figure 3:
FIG. 3 is a fluorescence micrograph of a microchannel covered with human umbilical vein endothelial cells ("HUVECs").
Figure 4A:
FIG. 4A is a confocal immunofluorescence microscopic image showing a top view of a microchannel section with HUVECs.
Figure 4B:
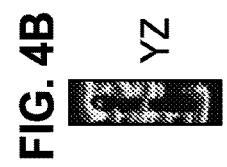
FIG. 4B shows a front view of the microchannel section of FIG. 4A.
Figure 4C:
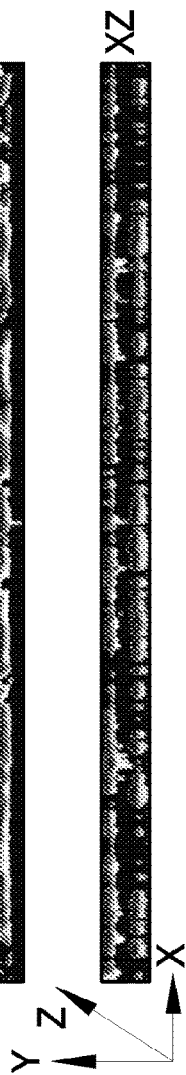
FIG. 4C shows a side view of the microchannel section of FIG. 4A.
Figure 5:
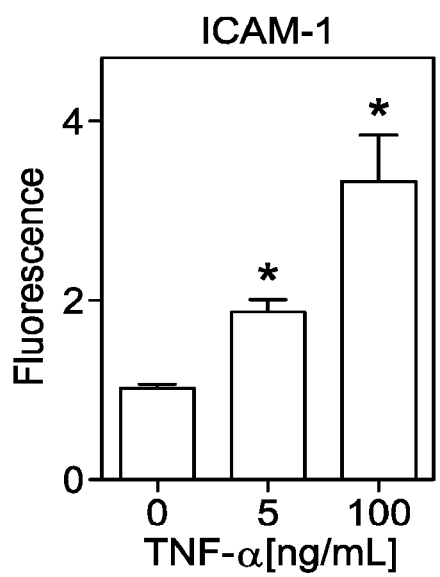
FIG. 5 is a graph that shows fluorescence measured after immunostaining a fixed endothelium with ICAM-1.
Figure 6:
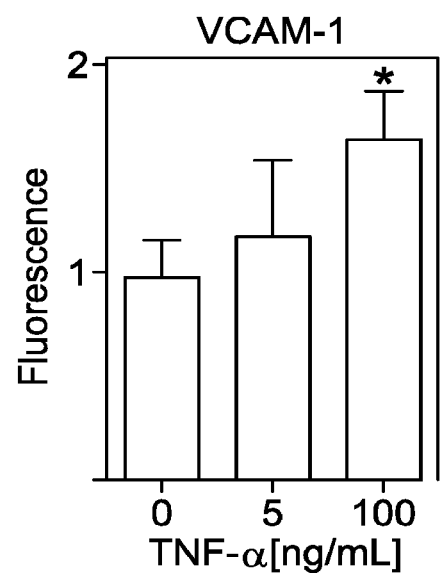
FIG. 6 is a graph that shows fluorescence measured after immunostaining a fixed endothelium with VCAM-1.
Figure 7:
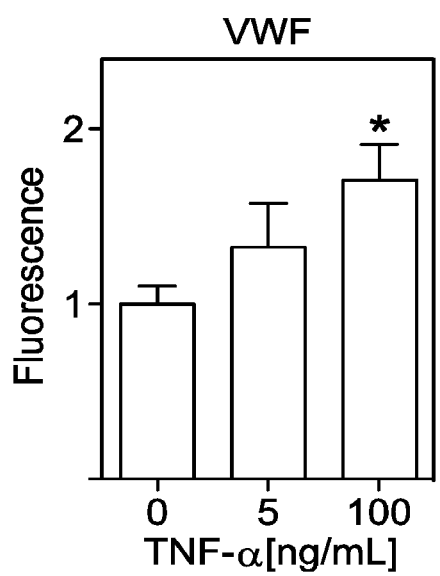
FIG. 7 is a graph that shows fluorescence measured after immunostaining a fixed endothelium with VWF.

In reference to FIGS. 3 and 4A-4C, the inner surface of the rectangular microchannel 102 is coated with collagen and, then, is cultured with HUVECs to create a tube lined by a continuous, confluent endothelial cell monolayer. Specifically, FIG. 3 illustrates a fluorescence micrograph that shows the entire microchannel covered with HUVECs stained with VE-cadherin junction marker (scale bar—1 mm). FIGS. 4A-4C illustrate confocal immunofluorescence microscopic images showing a section of the microchannel 102 with HUVECs when viewed from above in the xy plane (FIG. 4A), and reconstruction of cross-sectional views from the front yz plane (FIG. 4B) and the side xz plane (FIG. 4C). This demonstrates full coverage of all microfluidic microchannel walls. In this example, the microfluidic device 100 includes VE-Cadherin, nuclear DAPI, with a scale bar of 200 μm.

Multiple endothelial adhesion molecules are involved in the recruitment of blood cells and platelets in thrombosis in vivo. In previous studies, treatment of a living endothelium cultured in microfluidic channels with TNF-α results in an increase in expression of surface adhesion molecules, such as ICAM-1 and VCAM-1 within four hours after addition. To explore whether a fixed endothelium retains expression of these and other surface molecules that could potentially exacerbate thrombosis, the endothelium is first activated in the device by adding increasing doses of TNF-α, e.g., 0, 5, and 100 nanograms/millliter ("ng/ml"), for approximately 18 hours. The endothelium cells are fixed with 4% paraformaldehyde in phosphate-buffered saline ("PBS") for 15 minutes at room temperature, are rinsed three times with PBS, and, then, stored in PBS at 4° C. in a humid environment.

Figure 8:
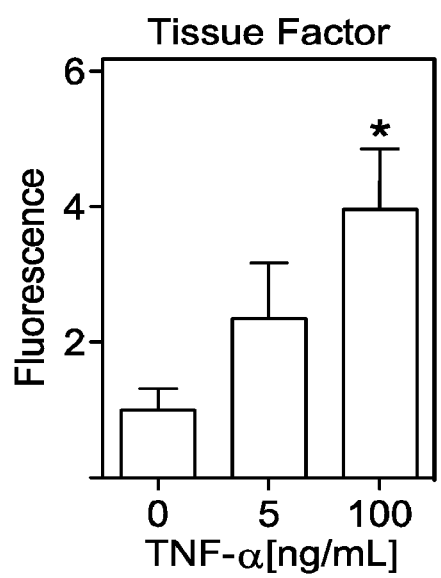
FIG. 8 is a graph that shows fluorescence measured after immunostaining a fixed endothelium with a tissue factor.

In reference to FIGS. 5-8, graphs show fluorescence (normalized by the untreated endothelium) measured after immunostaining the fixed endothelium, which continues to exhibit a dose-dependent increase in ICAM-1 (FIG. 5), VCAM-1 (FIG. 6), VWF (see. 7), or tissue factor (FIG. 8). In the graphs, *$P<0.05$ versus untreated and n=3. These results indicate that the fixed endothelium retains expression of multiple molecules that mediate adhesion of blood cells and platelets after activation with TNF-α, and induce clotting.

B. Fibrin and Platelet Function Analysis Using a Fixed Endothelium

To explore whether the fixed endothelium in the microfluidic devices retains the ability to promote hemostasis, recalcified citrated whole blood (coagulation activated) is immediately perfused through a microfluidic channel lined by the fixed endothelium and preserved for 24-36 hours. Platelet adhesion is analyzed for 15 minutes of flow.

Referring generally to FIGS. 9-11B, platelet coverage and fibrin formation is illustrated on a fixed endothelium in the microfluidic device 100. When blood from a healthy donor is flowed over an endothelium that is fixed without prior treatment with TNF-α, there is virtually no platelet adhesion on the surface, as would be expected for a healthy endothelium. In contrast, when microfluidic devices are used with endothelium that is treated with increasing doses of TNF-α prior to fixation, a dose-dependent increase in platelet surface adhesion to the endothelial layer is observed.

Referring more specifically to FIG. 9, representative maximum intensity projection micrographs show fluorescently labeled platelets adhering to a chemopreserved endothelium in a TNF-α does-dependent manner (scale bar—100 μm). Referring to FIG. 10, a graph shows platelet coverage when blood is perfused inside the microchannel 102 that is lined with a living or fixed endothelium, which has been stimulated by TNF-α before fixation. Of note, no significant difference is observed in platelet adhesion when comparing living versus chemopreserved endothelium, with or without treatment with TNF-α. For example, P>0.05 at each TNF-α concentration (n=4, *P<0.05). Referring to FIGS. 11A and 11B, fluorescent micrographs show fibrin that is formed along with platelet aggregates on a fixed endothelium, which has been pretreated with TNF-α (5 ng/ml) and perfused with recalcified citrated whole blood (FIG. 11A—scale bar—200 μm; FIG. 11B—scale bar—20 μm).

These results confirm that the fixed surface of the endothelium retains its pro-thrombotic function after fixation. Furthermore, when perfusing whole blood containing fluorescently labeled fibrinogen, the thrombi also contains a significant amount of fibrin if the endothelium was pretreated with TNF-α before fixation. This further confirms that the preserved endothelial surface also retains its ability to activate the coagulation cascade. The morphology of these thrombi also appear similar to that of thrombi formed on living endothelium in vivo, and significantly different from bare collagen-coated flow. Together, these results demonstrate that the fixed endothelium is capable of reproducing physiologically-relevant thrombus formation in our microfluidic device.

C. Potential Clinical Utility of the Device Lined with Fixed Endothelium

In accordance with another exemplary embodiment, a microfluidic device containing a fixed endothelium is used to detect antiplatelet drug effects in healthy donors and patients taking antiplatelet medication. For example, the cultured endothelium is pretreated with a physiologically relevant dose of TNF-α (e.g., 5 ng/mL). The microfluidic device contains the fixed activated endothelium with whole blood from a healthy donor containing 0 to 100 μg/mL (e.g., a clinical range—1-10 μg/mL) of the antiplatelet GP IIb/IIIa antagonist, abciximab (ReoPro®).

Referring to FIG. 12, a graph illustrates platelet coverage on a fixed endothelium that is pretreated with TNF-α when blood samples, which contain different doses of the drug abciximab, are perfused through a microfluidic device (such as the microfluidic device 100 illustrated in FIG. 1). Thus, when the microfluidic device is perfused, a dose-dependent inhibition of platelet adhesion is observed, with optimal effects observed at 10 μg/mL or higher. This is consistent with previous studies using flow cytometric analysis.

Referring to FIG. 13, a graph illustrates light transmission aggregometry of blood samples containing different doses of abciximab using either ADP or collagen as an agonist (n=4). Thus, in contrast to the results shown in FIG. 12, all concentrations of the drug abciximab produce virtually complete inhibition of platelet aggregation (e.g., no dose dependence) as detected using LTA, regardless of whether ADP or collagen was used as an agonist.

Referring to FIG. 14, a graph illustrates platelet coverage when blood samples containing different doses of the drug abciximab are perfused through collage-coated microfluidic devices (n=4). While there appears to be a small suppressive effect on platelet adhesion when the same blood samples are flowed through an acellular collagen-coated flow chamber, the sensitivity is extremely low and the differences between abciximab doses are not statistically significant.

Thus, the microfluidic device containing the fixed endothelium provides an optimally sensitive measure of platelet function, with a higher dynamic response across a range of abciximab concentrations than existing platelet function assays. These results suggest that a fixed endothelialized microfluidic device is likely useful in monitoring antiplatelet regimens in patients and has functional advantages over acellular conventional assays. These results also indicate that the fixed surface of the endothelium retains its ability to modulate platelet interactions via a GPIIb/IIIa pathway, the target of abciximab, which is involved in multiple thrombotic and vascular processes.

Referring to FIG. 15, a graph illustrates platelet coverage on a fixed endothelium that has been pretreated with TNF-α when blood samples from healthy donors, versus subjects treated with antiplatelet drugs, are perfused through microfluidic devices (n=11). Thus, whole blood is perfused from subjects who are regular users of antiplatelet drugs, with the subjects showing a significant reduction in platelet aggregation when tested using the microfluidic devices, in comparison to healthy donors.

Referring to FIG. 16, a graph illustrates light transmission aggregometry of healthy versus antiplatelet treated blood samples using ADP or collagen as an agonist (n=11). Thus, while similar results are obtained using conventional LTA, a microfluidic assay in accordance with the present disclosure requires a significantly reduced time period to complete (e.g., only 15 minutes) relative to the much longer time period for an aggregometry test (which must account for sample preparation time).

Referring to FIG. 17, a graph illustrates platelet coverage when healthy versus subject blood samples are perfused through collagen-coated microfluidic devices (n=11; *P<0.05). Thus, platelet inhibition in these subjects is not reliably detected on a collagen-coated flow chamber as there is no significant difference in platelet coverage between normal controls and subjects. Accordingly, the embodiments described above demonstrate that a microfluidic device containing fixed endothelium is potentially applicable in point-of-care settings.

One benefit of a microfluidic device, which contains human endothelial cells that are chemically preserved by fixation, is that it can be stored, shipped, and used when required, either in a laboratory setting or in point-of-care settings. Another benefit of such a microfluidic device is that it is a functional assay used to evaluate platelet aggregation and inhibition with drugs in blood samples of patients. Yet another benefit of such a microfluidic device is that it provides an assay with increased sensitivity than existing assays, and is helpful in rapid analysis of platelet function and hemostasis while incorporating contributions from the endothelium and dynamic blood flow.

Although the fixed endothelium may lose some of its live in vivo functions (e.g., release of bioactive messengers like nitric oxide), and the exact mechanism by which the surface promotes platelet aggregation and thrombosis is most likely multi-factorial, the above-discussed results suggest that for a period of 15 minutes of blood flow, the fixed endothelium retains its ability to prevent blood clotting under unstimulated conditions. The results further suggest that the fixed endothelium promotes platelet aggregation and thrombosis when pretreated with TNF-α prior to fixation. Notably, the qualitative and quantitative pro-thrombotic and pro-coagulant responses of the fixed endothelium closely mimic those of the living endothelium, suggesting that the fixed endothelium also permits the study of thrombus formation on a surface that mimics an inflamed endothelium, such as might be found in an atherosclerotic plaque.

III. ALGORITHM—RESULTS

A. Morphological and Quantitative Analysis of Thrombus Formation

Figure 18:
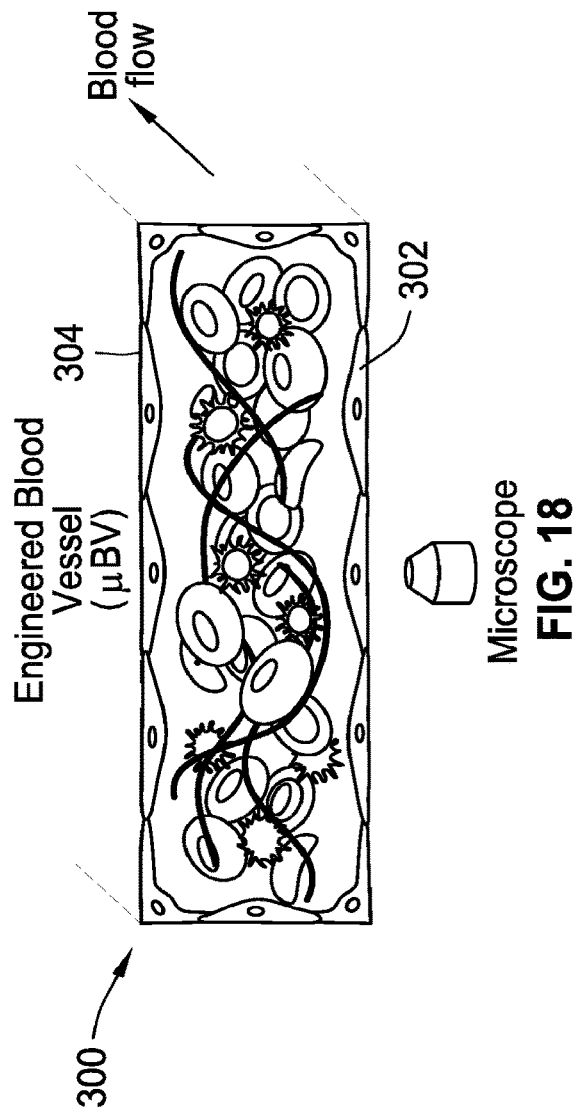
FIG. 18 is an illustration of a microfluidic blood vessel with cultured endothelial cells.

Referring to FIG. 18, a microfluidic device 300 in the form of a bioengineered microfluidic blood vessel contains cultured endothelial cells 302 on all walls of a microchannel 304 (also referred to as a vascular chamber). According to one embodiment, the microfluidic device 300 is similar to or identical with any of the microfluidic devices 100, 200 described above. The vessel 300 and endothelial cells 302 are intended to mimic morphology of a blood clot seen in vivo. Thus, whole blood (containing fluorescently labelled platelets) is perfused through the microfluidic device 300.

The morphology of thrombus and platelet-endothelial dynamics, which occurs in the microfluidic device 300, is characterized via an imaging and quantitative analysis technique. Specifically, the technique characterizes the morphology as it may occur in vivo and as a result of endothelial cells activation, blood cells, and shear stress. For example, imaging of recalcified citrated whole blood, which contains labelled platelets perfused inside a small section of a vascular chamber 304 (no epithelial cell culture), platelet adhesion on a bare collagen surface occurs rapidly, firmly, and increasing steadily over a timespan in the range of about 10 minutes (e.g., 2.5-12.5 minutes).

Figure 19:
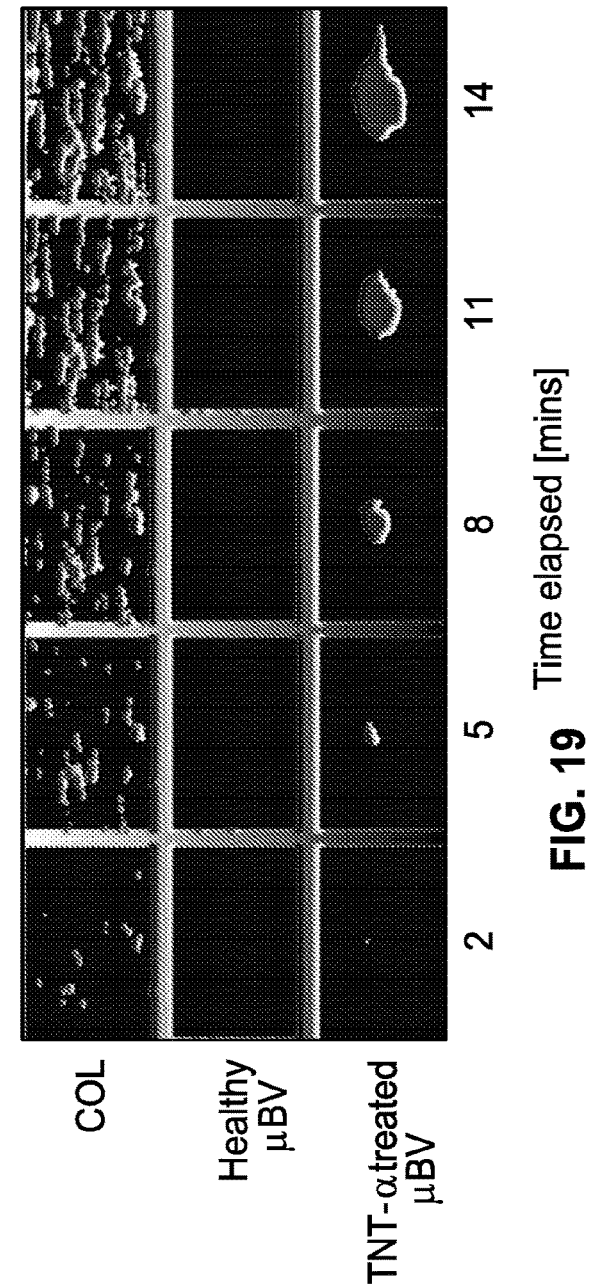
FIG. 19 shows fluorescence micrographs depicting a section of an imaged microchannel showing platelet accumulation (left to right) on collagen, a healthy blood vessel, and a TNF-α stimulated vessel.

Referring to FIG. 19, fluorescence micrographs depict a section of the imaged microchannel 304 showing platelet accumulation (left to right) on collagen, a healthy blood vessel, and a TNF-α stimulated vessel. This imaging is consistent with past observations and is reminiscent of formation of a hemostatic plug under vascular injury. In contrast, when the lumen chamber 304 is covered with a continuous living endothelial monolayer over collagen, very little platelet interactions and aggregate formation occur over the course of an experiment, much as what is observed in blood flowing in a healthy human blood vessel. However, when endothelial cells are stimulated with an inflammatory cytokine tumor necrosis factor (e.g., TNF-α; 100 ng ml$^{-1}$) prior to blood flow, platelet adhesion again occurs. Nevertheless, the morphology of the thrombus is clearly distinct from aggregates formed on the collagen surface.

Referring to FIG. 20, fluorescence micrographs depict a section of the imaged microchannel 304 showing platelet accumulation after 4 minutes of laser-induced injury on a mouse cremaster arteriole (scale bar—µm 25). The typical size of aggregates on activated endothelium is visibly larger and, interestingly, the size, shape, and organization of the thrombi formed on the activated endothelium in this in vitro model correlates well with what is observed in a mouse model of laser-induced thrombosis in vivo. This confirms the patency of the in vitro setup in reproducing physiologically-relevant thrombus formation, which is missing in simple collagen-coated devices.

Referring to FIG. 21, fluorescent micrographs of a large section of the vascular chamber 304 shows intravascular thrombus formation in collagen (top image), and TNF-α stimulated endothelium in a dose dependent manner (bottom three images). The scale bar is 100 µm. The micrographs are helpful in identifying quantitative parameters for a comparative and cumulative analysis of a large number of platelet-endothelial interactions that occur over a long region in the microfluidic device 300.

Specifically, the analysis includes a method to quantitate platelet function in flow chambers and microfluidic devices that has been primarily limited to analyzing platelet adhesion on bare collagen surfaces. To analyze platelet-endothelial dynamics that will act as a robust readout of physiologically-relevant clotting, an automated imaging program creates an image time-series, K(x, y, t), containing a 10-frame panorama in space. Images are acquired at a frame rate of 2 panoramic images per minute, for a total time of 15 minutes. A non-dimensional stochastic index is derived to quantitate platelet endothelial dynamics ("P-E"), which is the interpercentile range of a coefficient of variance of the image time-series:

$$P\text{-}E=\text{range}(CV(K(x,y,t)) \tag{1}$$

A feature of this analytical readout is that instead of an "ensemble averaging," the method incorporates the cell-surface interactions at the pixel level and quantitates statistical "dispersion" of interactions.

Figure 22:
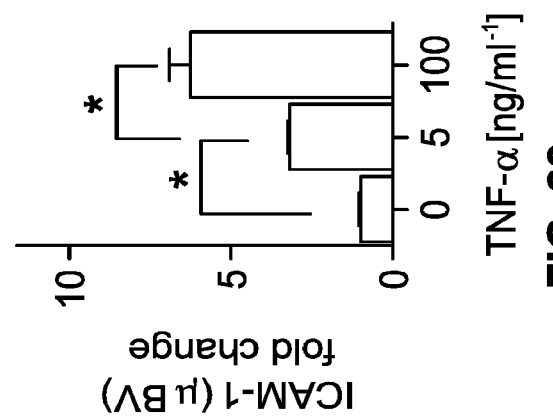
FIG. 22 is a graph illustrating ICAM-1 expression on the endothelial cells after stimulation with TNF-α.

Referring to FIG. 22, a graph illustrates ICAM-1 expression on the endothelial cells after stimulation with TNF-α. Specifically, the graph illustrates testing of the sensitivity of parameter (P-E) in response to changes in endothelial activation, and the stimulation of the endothelial vessel with various doses of TNF-α, which result in a dose-dependent surface expression of adhesion molecule ICAM-1 (n=3).

Figure 23:
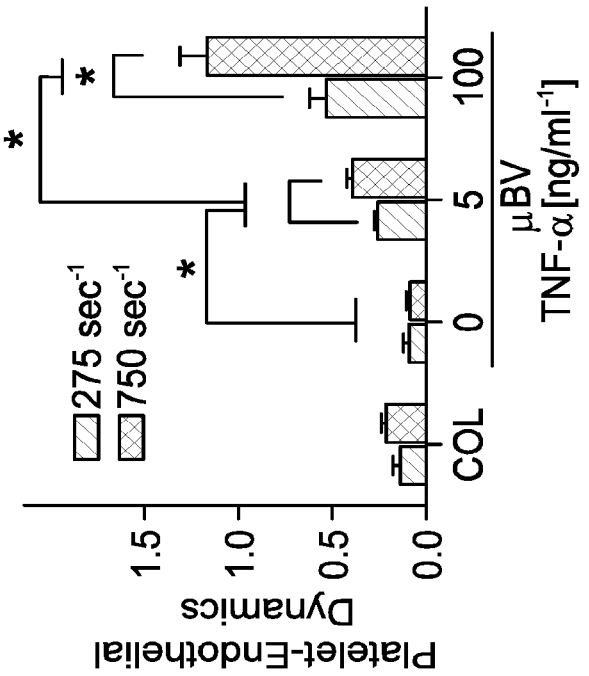
FIG. 23 is a graph illustrating a sensitivity analysis of a platelet endothelial dynamics algorithm.

Referring to FIG. 23, a graph illustrates a sensitivity analysis of the platelet endothelial dynamics algorithm, showing that in conditions of hemostasis (e.g., vascular injury/collagen or healthy endothelium), the dynamics are near absent. However, the dynamics increase in a TNF-α dose dependent manner. The platelet endothelial dynamics are also sensitive to applied shear rate (e.g., n=3, *P<0.05). Thus, a dose-dependent effect in P-E, shows that the method is sensitive to vasculopathy induced thrombosis (e.g., n=4).

Figure 40:
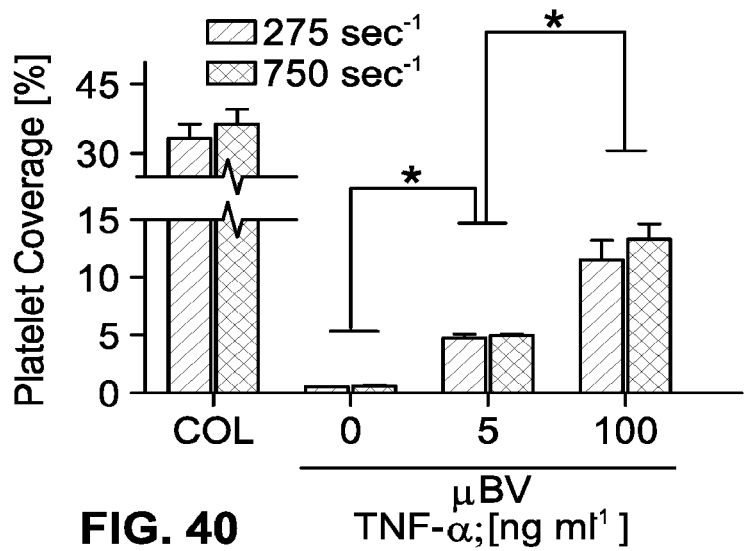
FIG. 40 is a chart illustrating platelet coverage on a microchip covered with collagen.

In fact, unlike platelet adhesion (such as illustrated in FIG. 40), the P-E on a bare collagen surface is extremely low. This shows that the present method distinguishes between the conditions of hemostasis (e.g., in a healthy vessel or vascular injury) and thrombosis due to inflammation. Furthermore, shear stress is a major determinant, for example, of endothelial function, blood rheology, platelet activation, or immune function, which, together, can alter thrombosis.

Figure 41:
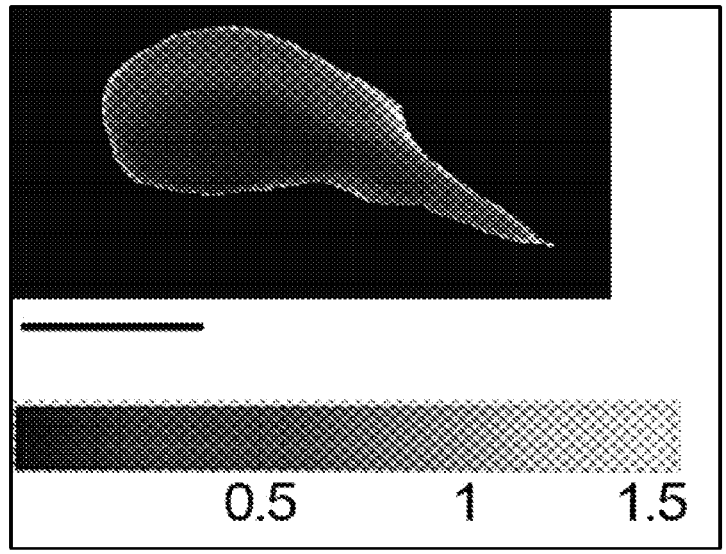
FIG. 41 shows a coefficient of variation (CV) colormap of a single thrombus formed in a laser injured mouse in vivo.

The P-E parameter is also sensitive to applied shear stress, and is indicative of a higher tendency to form platelet-rich thrombi and platelet-endothelial interactions, as shear is increased (see FIG. 22). In contrast, area-averaged platelet adhesion is not sensitive to shear (see FIG. 40). Notably, a CV colormap of a single thrombus formed in a laser injured mouse in vivo, shows high reactivity at the boundary compared to the central core, which is also observed in individual thrombi that are formed in a microfluidic device, in vitro (see FIG. 41).

Interestingly, these regional heterogeneities in the thrombus that are revealed in accordance with the method described above, have also been confirmed by computational studies and also in vivo, showing that a thrombus consists of a stable core region surrounded by reactive unstable shell. Furthermore, the method described above shows that the platelet-endothelial dynamics (P-E) parameter is a robust parameter that is applicable to quantitate platelet function and thrombosis, both in vitro and in vivo, where the endothelial function is also included.

B. Engineering of the Pulmonary Thrombosis-On-Chip

Referring generally to FIGS. 24-26, to model physiologically-relevant pulmonary hemostasis and thrombosis, a lung-on-a-chip device not only allows co-culture of lung epithelial and endothelial cells in the presence of physiological relevant shear, but also includes primary human cells and a more functional arterial blood vascular lumen in which human whole blood can be perfused. Referring specifically to FIG. 24, a conceptual schematic of a human lung 400 shows that the alveoli 402 interacts with neighboring blood vessels 404 during hemostasis or pulmonary dysfunction. Referring specifically to FIGS. 25 and 26, a microfluidic device 500 contains two PDMS compartments 502 (which include a top compartment 502A and a bottom compartment 502B) separated by a thin porous membrane 504 that reproduces the microarchitecture of the alveolar-capillary interface. The microfluidic device 500, according to this example, is in the form of a lung-on-a-chip device. The top compartment 502A is cultured with human primary alveolar epithelial cells 506 and the entire bottom chamber 502B is lined with human endothelial cells 508 forming a lumen. Whole blood is perfused through the bottom chamber 502B and thrombus formation is visualized using fluorescence microscopy from the bottom. Optionally, or alternatively, the compartments 502A, 502B are in the form of channels.

Figure 27:
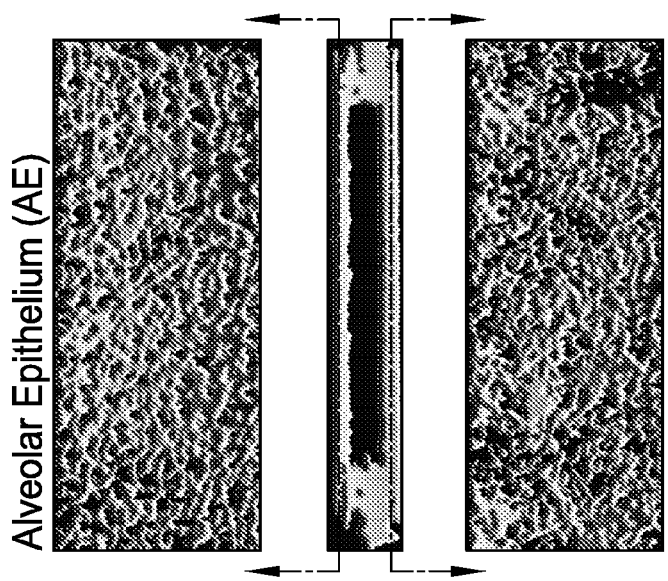
FIG. 27 shows visual stacks of confocal micrographs with junctional structures, after twelve days of co-culture.

Referring to FIG. 27, visual stacks of confocal micrographs show junctional structures, after twelve days of co-culture, of a single layer of the primary alveolar epithelium 506 at the top chamber 502A (stained with e-cadherin) and endothelial monolayers 508 covering either side of the lower chamber 502B (stained with ve-cadherin), through which blood perfusion takes place. The scale bar for the top and bottom images of FIG. 27 is 50 μm, and the scale bar for the middle image is 250 μm.

Thus, in the alveolar chamber 502A, human primary alveolar epithelial cells ("AE") are cultured and in the blood vessel chamber 502B, the entire chamber 502B is cultured with human endothelial cells (μBV) for a total of 12 days, thus creating an organ-level functional device 500 where the epithelial, endothelial, and blood cell interactions are visualized and analyzed in real-time, in the presence of whole blood flow and conditions that mimic thrombus formation in vivo. Notably, this lung-on-a-chip device 500 contains co-culture of healthy human primary alveolar cells and healthy endothelial cells that show barrier integrity and intact junctions even after 12 days of living culture, across the entire length and breadth of the device 500. Accordingly, in the state of hemostasis (e.g., healthy cell culture and perfusion of healthy blood), perfuse recalcified citrated whole blood (coagulation activated) is perfused for up to 20 minutes without any observed platelet adhesion or clotting inside the lumen of the lung-on-chip device 500. This confirms the formation of a healthy organ-level functional microfluidic device 500 that is capable of resembling the state of hemostasis.

Figure 28:
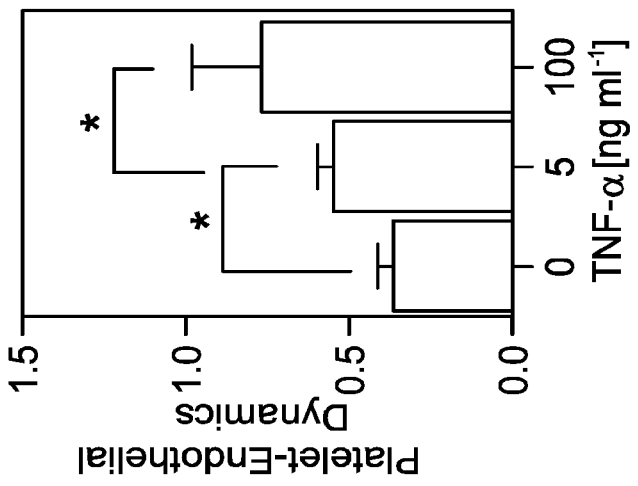
FIG. 28 is a chart showing vascular ICAM-1 measured after TNF-α stimulation relative to untreated cells in the presence of alveolar epithelial cells (AE).

Referring to FIG. 28, a chart shows vascular ICAM-1 measured after TNF-α stimulation relative to untreated cells in the presence of AE (e.g., n=3). Specifically, upon stimulation of the lung-on-chip microfluidic device 500 with TNF-α on the alveolar compartment 502A containing AE, the vascular ICAM-1 expression increases in a dose-dependent manner, reproducing endothelial stimulation as has been previously observed.

Figure 29:
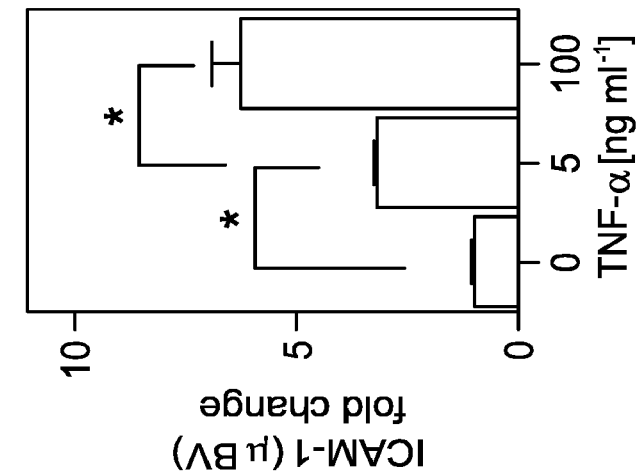
FIG. 29 is a chart showing platelet-endothelial dynamics in a microfluidic device that follows a similar trend as ICAM-1 of FIG. 28.

Referring to FIG. 29, and correspondingly with respect to the chart of FIG. 28, the platelet-endothelial dynamics in the microfluidic device 500 follows a similar trend as ICAM-1. Specifically, a chart shows platelet-endothelial dynamics in an untreated vs TNF-α stimulated lung-on-a-chip device 500 (n=3. *P<0.05).

Figure 30:
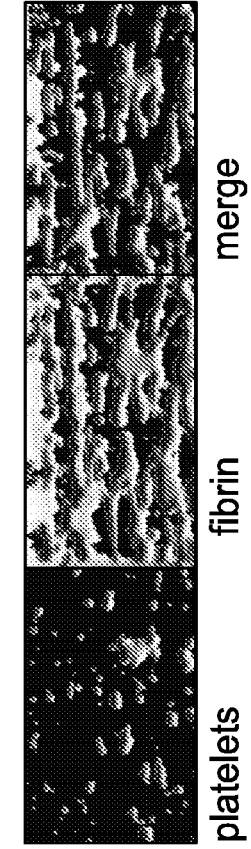
FIG. 30 shows fluorescent micrographs with platelets (left), fibrin (middle), and merged (right) on an endothelial surface when stimulated by TNF-α.

Referring to FIG. 30, at the end of the assay, due to vascular activation, significant amount of clots are observed. The clots are constituted by platelets and fibrin localized within the vascular compartment 502B of the lung-on-a-chip device 500. Specifically, fluorescent micrographs showing platelets (left), fibrin (middle), and merged (right) on an endothelial surface, when stimulated by TNF-α (scale bar—100 μm). This confirms that the lung-on-a-chip device 500 is sensitive to the pro-inflammatory effect of the TNFα. The epithelial stimulation, which can result in signalling from the epithelial side to the endothelium, promotes activation of the endothelial cells and blood cells, such as, platelets, finally causing intravascular thrombus formation.

C. Lipopolysaccharide ("LPS") Induced Inflammation and Thrombosis

Referring generally to FIGS. 31-35, an evaluation is directed to more complex epithelial-endothelial-blood cell interactions and to better define the link between local inflammation and thrombosis. The evaluation includes stimulating a microfluidic device on the alveolar epithelial cells (AE) side with a lipopolysaccharide (LPS) endotoxin, and comparing P-E when the stimulation occurs in the presence or absence of the alveolar epithelial cells (AE). The microfluidic device is any of the microfluidic devices described above (e.g., microfluidic device 300, lung-on-a-chip device 500, etc.).

Figure 31:
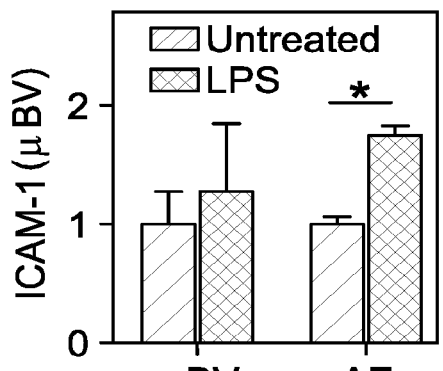
FIG. 31 is a chart showing vascular ICAM-1 that is measured after LPS stimulation relative to untreated cells in the presence or absence of alveolar epithelial cells (AE).

Referring specifically to FIG. 31, a chart shows vascular ICAM-1 that is measured after LPS stimulation relative to untreated cells in the presence or absence of the alveolar epithelial cells (AE) (n=3). When the blood vessel alone is stimulated with LPS for 2 hours, it results in no significant increase in ICAM-1, and the endothelium is inflamed only when the LPS stimulation occurs over the AE.

Figure 32:
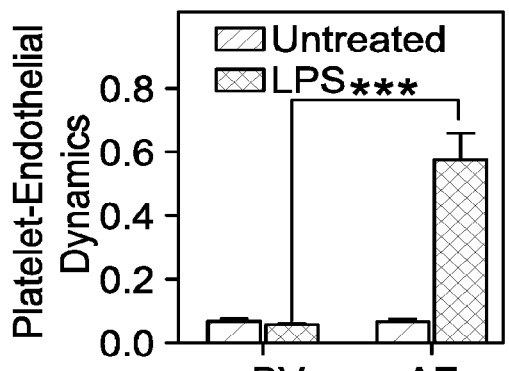
FIG. 32 is a chart showing platelet-endothelial dynamics measured in a microfluidic device, in the presence or absence of the alveolar epithelial cells (AE).

Referring specifically to FIG. 32, platelet-endothelial dynamics measured in the microfluidic device, in the presence or absence of the alveolar epithelial cells (AE), are either left untreated or are stimulated with various doses of LPS (n=3, *P<0.001). Thus, the P-E is near absent when the lung-on-a-chip device is left untreated or is treated with LPS in the absence of AE. Furthermore, the P-E significantly increases when the stimulation occurs over the AE.

Figure 33:
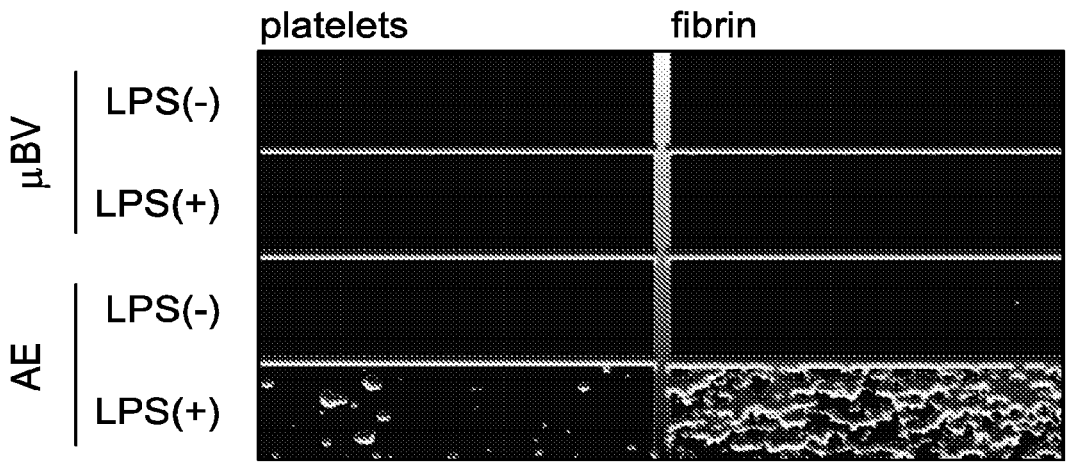
FIG. 33 shows fluorescence micrographs with platelet aggregates and fibrin at the end of blood perfusion through a microfluidic device.

Referring specifically to FIG. 33, representative fluorescence micrographs show platelet aggregates and fibrin at the end of blood perfusion through the microfluidic device. The microfluidic device contains and compares untreated and LPS stimulation, in the presence or absence of AE (scale bar—100 μm). Thus, at the end of blood perfusion in the LPS-stimulated microfluidic device containing AE, large platelet aggregates are formed along with significant fibrin in the lumen. This demonstrates in vitro that in situ thrombosis in the vascular lumen is caused by an LPS-directed epithelial injury.

Figure 34:
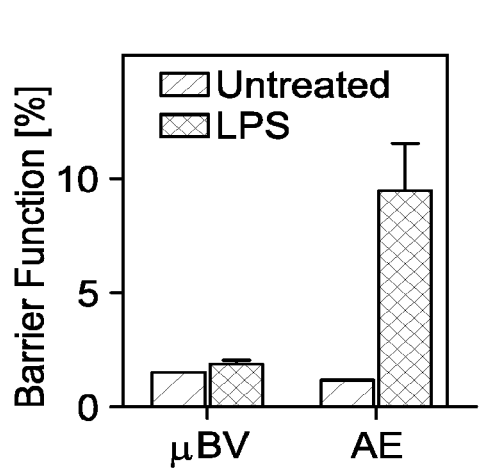
FIG. 34 is a chart showing barrier permeability measured after LPS stimulation, relative to untreated cells in the presence or absence of the alveolar epithelial cells (AE).

Referring specifically to FIG. 34, a chart shows barrier permeability measured after LPS stimulation, relative to untreated cells in the presence or absence of the alveolar epithelial cells (AE) (n=1 or 2). Thus, the trend that occurs due to the epithelium is further confirmed when the barrier permeability is measured.

Figure 35:
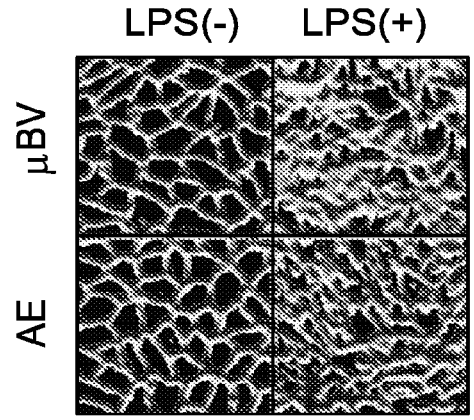
FIG. 35 shows representative confocal micrographs with gap junctions under no treatment or LPS treatment, in the presence of a blood vessel alone or with epithelium (AE).

Referring specifically to FIG. 35, representative confocal micrographs show gap junctions under no treatment or LPS treatment, in the presence of a blood vessel alone or with epithelium (AE). The visualized gap junctions are not affected when the blood vessel is stimulated with LPS, but significantly increase in the presence of AE.

Figure 36:
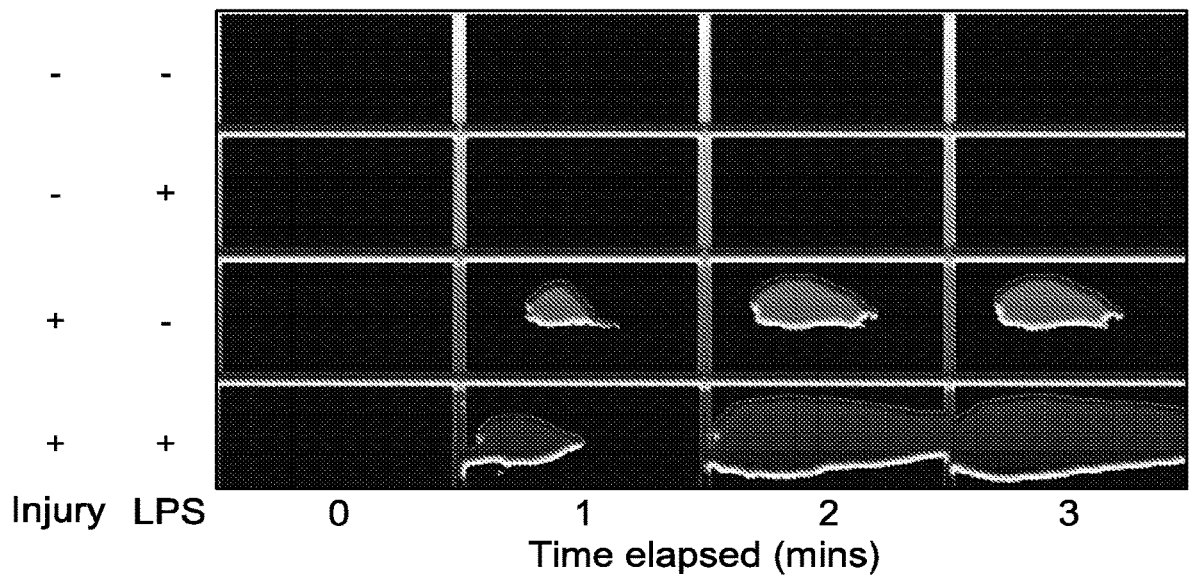
FIG. 36 shows fluorescent micrographs illustrating evolution of blood clots (left to right) in a cremaster artery of the mouse.
Figure 37:
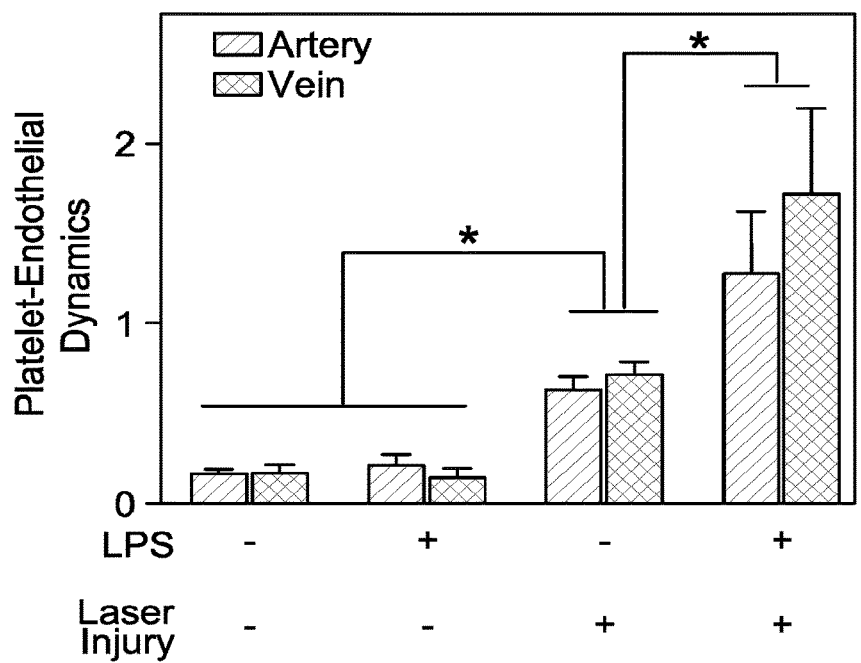
FIG. 37 is a chart showing platelet-endothelial dynamics computed on fluorescent time-series of platelets.

Referring generally to FIGS. 36 and 37, the technique described above in reference to FIGS. 31-35 has been further applied to a laser injury induced thrombus formation in vivo in a cremaster arteriole and a cremaster vein of a mouse, along with a systemic delivery of LPS. When a mouse is injured with laser, significant clotting is observed in both the artery and vein, along with increase in P-E. The increase in P-E is further exacerbated when LPS is administered additionally. However, administration of LPS alone does not induce any platelet-endothelial interactions.

Referring specifically to FIG. 36, fluorescent micrographs show evolution of blood clots (left to right) in a cremaster artery of the mouse. The cremaster artery is left untreated, laser injured or after systemic injection of LPS (scale bar: 25 μm).

Referring specifically to FIG. 37, a chart shows platelet-endothelial dynamics computed on fluorescent time-series of platelets. The platelets adhere to a cremaster artery or a vein of a mouse (n=3, *P<0.05).

Figure 42:
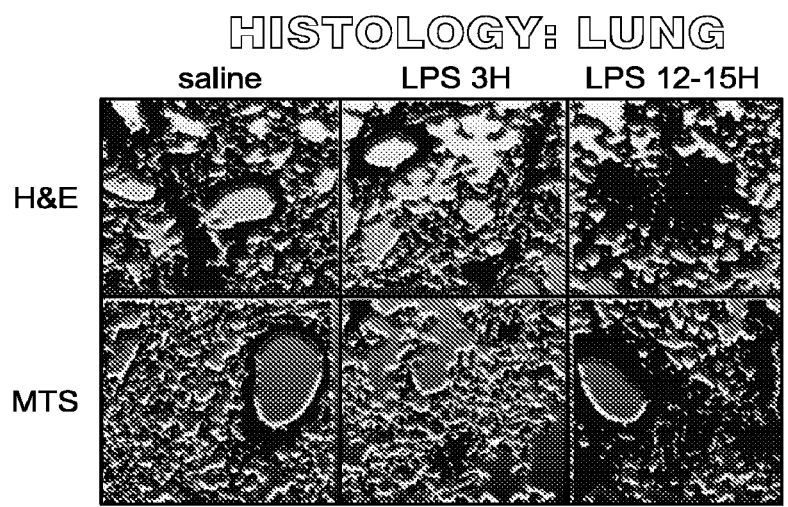
FIG. 42 shows histological sections representing sections of a mouse lung with clots.

Referring to FIG. 42, histological sections show sections of a mouse lung with clots. The sections of the mouse lung are left untreated or treated with LPS. Thus, in contrast to the results described in reference to FIGS. 36 and 27, the histological analysis of the mouse lung shows that the LPS injection results in lung injury and pulmonary thrombosis. This shows that either an exogenous stimulation (e.g., a laser injury) or possibly an epithelium (e.g., in a lung), are likely essential to platelet adhesion and thrombosis (as also recreated in vitro) in the microfluidic device. Therefore, an LPS-stimulated lung-on-a-chip device is potentially a robust model for testing potential antithrombotic and anti-inflammatory drug candidates, in an organ-level functional environment of pulmonary epithelial-endothelial-blood cell signalling.

D. Analysis of Cytoprotective Effect of PAR-1 Inhibitor

Figure 38:
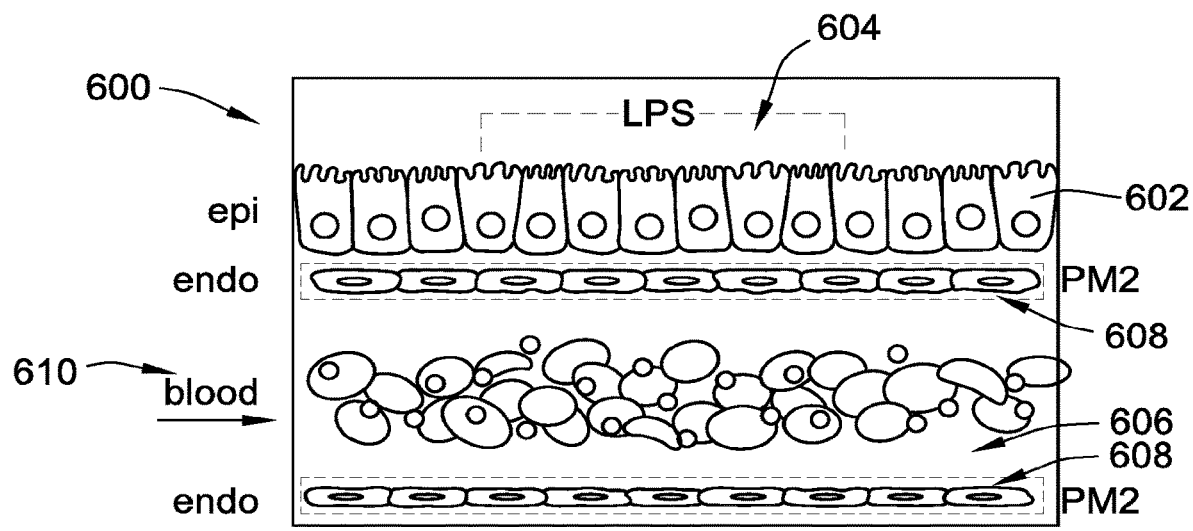
FIG. 38 is an illustration showing a microfluidic device that contains alveolar epithelial cells (AE) treated with LPS and a vessel treated with parmodulin (PM2).

Referring to FIG. 38, an illustration shows a microfluidic device 600 that contains alveolar epithelial cells (AE) 602 treated with LPS 604 and a vessel 606 treated with parmodulin (PM2) 608 to inhibit thrombosis due to lung injury. Thus, the microfluidic device 600 is stimulated on the AE side 602 with LPS and is perfused with blood 610 in the vessel 606. The microfluidic device is similar to or identical with one or more of the microfluidic devices described above. In response to the stimulation, no significant clotting occurs and P-E occurs PM2 is added to the endothelial cell culture medium.

Figure 39:
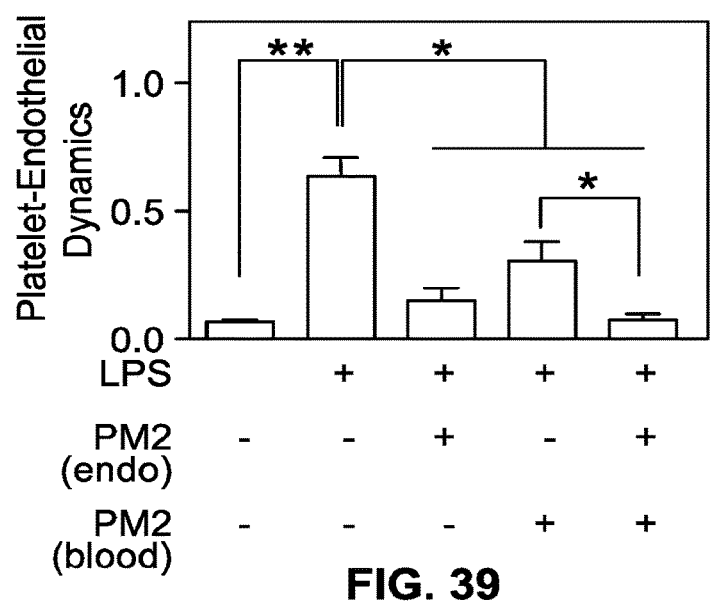
FIG. 39 is a chart showing platelet-endothelial dynamics that are measured in a microfluidic device containing AE cells.

Referring to FIG. 39, a chart shows platelet-endothelial dynamics that are measured in the microfluidic device 600 containing AE cells (n=3. *P<0.05,**P<0.01). Additionally, adding PM2 to blood 610 alone also results in the reduction of P-E as it prevents PAR-1 activation of platelets. Furthermore, adding PM2 to both endothelium and platelets completely inhibits the P-E and thrombotic activity in this LPS-stimulated alveolar microfluidic device 600.

As such, the approach described in reference to FIGS. 38 and 39 show a cytoprotective and anti-thrombotic effect of PM2 in a physiologically-relevant model of acute lung dysfunction. Thus, the approach provides a beneficial drug candidate for intervention in diseases that cause pulmonary thrombosis. Notably, the approach demonstrates the strength of the in vitro microfluidic device 600, allowing visualization and quantitative analysis of organ-level interactions in real-time, including the epithelium (e.g., stimulated with LPS), endothelium (e.g., protected by PM2), and whole blood cells (e.g., coagulation and platelet function). A similar experiment in vivo is extremely difficult to perform, if not impossible.

IV. Algorithm—Discussion

Generally, a salient feature of pulmonary organ-on-chip microfluidic technology is that it permits perfusion of human whole blood in its native state (e.g., recalcified after anti-coagulation in sodium citrate) at any desirable shear rate. Thus, the microfluidic technology provides a significantly more physiologically-relevant in vitro platform to study and analyze intravascular clotting of a lung organ.

Additionally, by harnessing the full potential of modern automated fluorescence microscopy and mathematical algorithms that are designed to quantitate thrombus formation occurring in real-time inside a microfluidic device, platelet-surface interactions are assessed over large spatiotemporal scales. The approaches described above and below show that the integrated interplay between platelets, thrombi, a vessel wall, blood-borne factors, and flow dynamics are analyzed in the integrated system-level assay. Significantly, pulmonary clot formation is caused by endothelial activation that occurs in a microfluidic device in vitro and correlates to a mouse laser injury model in vivo, both in terms of morphology and regional heterogeneity. Thus, the described microfluidic device and analytical methods potentially act as a valuable tool for analyzing organ-level tissue-tissue interactions under pathophysiological conditions that are relevant for thrombosis and platelet research.

Furthermore, by incorporating primary alveolar epithelial cells that are co-cultured along with endothelial cells for up to 2 weeks, and maintaining physiological junction integrity, a limitation of previous lung-on-a-chip devices (which contain tumor derived cell lines) has been overcome. The present physiologically-relevant microfluidic device allows the finding that the epithelial cells can make a direct contribution to thrombosis, when stimulated by LPS. This finding is very difficult to show in vivo in real-time, as individual tissue and cellular compartments inside an organ cannot be individually regulated, and blood flow inside lung vessels cannot be observed over a large section.

Nevertheless, using the laser injury mouse model, it is demonstrated that LPS does not cause thrombosis in a cremaster artery or vein, but causes clotting in the lung. This is somewhat similar to in vitro observations, where LPS stimulation of endothelium alone does not cause thrombus formation, but, instead, LPS stimulation of epithelium results in vascular dysfunction and rapid clotting.

The described microfluidic devices and methods help unravel the cytoprotective and anti-thrombotic effect of a novel PAR-1 antagonist (PM2) in the setting of an acute lung injury and whole blood perfusion. The findings encourage the pharmaceutical industry to further test antithrombotic drugs using the described humanized platform, having the potential to cause vasculopathy and bleeding as a major toxicity (which is also very difficult to study in vivo). Overall, the described pulmonary thrombosis-on-a-chip microfluidic device may be further beneficial in finding potential applications in a variety of settings relevant for thrombosis research, e.g., toxicology, drug screening, and diagnostics. One likely future benefit may permit a personalized assessment of drug response to therapy, to help individualize drug delivery, by using patient derived cells and blood.

V. Algorithm—Materials and Methods

A. Device Fabrication

According to one example, one or more of the microfluidic devices described above are fabricated with Prototherm 12120 using stereolithography (such as provided by Protolabs, Maple Plain, Minn.). Top and bottom components of the microfluidic devices are cast from PDMS at a 10:1 w/w base to curing agent ratio. The components are degassed and, then, cured overnight for 4 hours at 60° C. The top component contains a fluidic channel (1×1 mm cross section) and ports for the top and bottom channels. PDMS membranes, which provide a semi-permeable barrier between the epithelium and microvascular endothelium layers, are fabricated by casting against a DRIE-patterned silicon wafer (50×50 mm). The wafer has posts that are 50 µm high and have a 7 µm diameter. The posts are spaced apart at a distance of 40 µm.

To produce through-holes in the membrane using the microfabricated post array, after pouring 100 µL of PDMS onto the wafer, a polycarbonate backing is compressed against the post array and is baked at 60° C. for 4 hrs. The membrane is bonded to the top component using oxygen plasma treatment (e.g., 40 Watts, 800 millibars, 40 seconds; Plasma Nano, Diener Electronic, Ebhausen, Germany), followed by bonding the assembly of the top component and membrane to the bottom component containing an endothelial channel (1 mm wide×0.2 mm high). The microfluidic devices are sterilized using oxygen plasma treatment (100 Watts, 15 standard cubic centimeters, 30-60 seconds; PlasmaEtcher PE-100, Plasma Etch, Reno, Nev.).

B. Cell Culture and Stimulation

After plasma treatment of the microfluidic devices, the two chambers are pre-treated with 10% (3-aminopropyl)-trimethoxysilane (APTMES, e.g., from Sigma) in 100% anhydrous alcohol (e.g., from Sigma) for 10-20 minutes. The chambers are flushed sequentially with 70% ethanol in water and 100% ethanol, and then dried at 60-80° C. for two hours. Then, a mixture of rat tail collagen I (100 µg ml$^{-1}$ in PBS, from BD Biosciences) and fibronectin (e.g., 30 µg/ml in PBSm, from BD Biosciences) is introduced in both chambers of the microfluidic device. The microfluidic device is incubated at 37° C. for at least 2 hours before flushing with PBS or EGM-2 cell culture media.

Some of the microfluidic devices are used with collagen coating alone (without cells). In other devices, HUVECs (e.g. from Lonza) are cultured in Endothelial Growth Medium-2 (EGM-2, from Lonza) and used between certain passages. The cells (5-10×10$^6$ cells/ml) are introduced into the collagen-coated channels and incubated for 20 minutes at 37° C. to promote cell attachment before a second similar HUVEC suspension is, then, introduced. The microfluidic devices are incubated upside down for an additional 20 minutes to seed the cells on the ceiling and walls of the lower chamber.

The lower chamber is then flushed with EGM-2 and, then, a suspension of primary alveolar epithelial cells (e.g., from ScienCell Research Labs, Carlsbad, Calif.; 5-6×10$^6$ cells ml$^{-1}$) is introduced into the top chamber of the device. After a few hours, the top and bottom chambers are flushed with their respective media, and the microfluidic devices are incubated at 37° C. under 5% $CO_2$ for 3 days (with media being replaced each day once). On day 4, the bottom vascular chamber is set on perfusion of EGM-2 media (e.g., 30 µL hr$^{-1}$; 0.5% fetal bovine serum) to provide shear to the HUVEC vessel chamber and a continuous supply of fresh media.

On day 6, the epithelial cell media in the top chamber is aspirated to create the air-liquid interface of the alveoli. Hereon, the cell culture continues for another 6-8 days, after which, in some cases, the top chamber is supplemented with 0, 5, or 100 ng ml$^{-1}$ TNF-α in PBS (e.g., from Sigma) overnight or LPS (e.g., 100 ng ml$^{-1}$ of *E. Coli*, from Sigma,) for 2 hours to cause cell activation. The LPS is sonicated in ultrasonic bath for about 20-30 minutes before introducing into the microfluidic device. After stimulation, the top chamber is clamped, the bottom chamber is rinsed with culture media, a reservoir cut from a 3 ml slip-tip syringe (e.g., from BD) is inserted on one end of the lower chamber, and a $^1$/$_{16}$-inch male luer connector (e.g., from Qosina Corp) is inserted on the other end of the lower chamber.

C. Blood Samples and Flow Conditions

Citrated human blood (e.g., from Research Blood Components, Cambridge, Mass.) is used within 5 hours of blood draw, to minimize pre-analytical effects on platelet function. Platelets are labeled with human CD41-PE antibody (e.g., 10 µl ml$^{-1}$, Invitrogen) that is directly added to the blood and is incubated at room temperature for about 10 minutes.

When analyzing the formation of fibrin, blood samples re added with 15 µg ml$^{-1}$ of fluorescently labeled fibrinogen (e.g., Alexa 488 from Invitrogen). The citrated blood is recalcified 2 minutes after the beginning of each experiment by adding 100 µl mL$^{-1}$ of a solution containing 100 mM calcium chloride and 75 mM magnesium chloride to the blood to permit calcium-dependent and magnesium-dependent platelet functions. Citrated human blood (e.g., 1.2 mL) is pipetted into a fluid reservoir fitted to one end of a microchannel on one side of the microfluidic device.

A piece of medical grade tubing (e.g., 1.58 mm inner diameter of Tygon S-50-HL from Saint Gobain Plastics) is fitted to the outlet port of the device via a barbed luer lock connector (e.g., Harvard Apparatus). The other end of the tube is connected to a 3 ml syringe (e.g., from Becton Dickinson) through which blood is withdrawn from the device by pulling the blood using a syringe pump (e.g., PHD Ultra CP, Harvard Apparatus), thereby driving blood flow through the microfluidic device. The flow rate is adjusted to result in a wall shear rate of 250 sec$^{-1}$ (e.g., approximately 10 dynes/cm$^2$ stress). For studying platelet-endothelial dynamics at a higher wall shear rate of 750 sec$^{-1}$ (e.g., approximately 30 dynes/cm$^2$ stress), a microfluidic device has an endothelial chamber smaller in size (e.g., 0.4 mm wide×0.1 mm high) to facilitate experiments in which less than 1 ml of blood is used.

D. Image Acquisition and Analysis

Platelet dynamics are visualized using time-lapse fluorescence imaging (e.g., LD Plan Neofluar 10×, NA 0.4; Zeiss Axio Observer; Hamamatsu ORCA C11440 CMOS digital camera) using an exposure time of 200 ms. Images are tiled to create a composite panoramic view (e.g., 18,600 pixels long and 2,050 pixels wide; 1 pixel=0.325 µm). Images are archived as OME-TIFF format files, and an image analysis is performed using, for example, Zeiss Zen 2012 imaging software and MATLAB 2014 routines.

E. Platelet-Endothelial Dynamics Algorithm

Referring generally to FIGS. 43-50, illustrations show the visualization and analysis of platelet-endothelial temporal dynamics. Specifically, the illustrations include space-time kymographs that are plotted to illustrate acquired image time-series and graphed fluorescence at a representative pixel over time, after removing the (linear) trend due to the increasing platelet adhesion alone.

Referring specifically to FIGS. 43-46, representative kymographs of a small section of a microchannel show an attachment and detachment pattern of platelets on a collagen surface (FIG. 43) or vessel that is untreated (FIG. 44) or TNF-α treated (FIG. 45). Referring specifically to FIG. 46, the coefficient of variance (CV) of a fluorescence signal is observed over time at a representative single pixel location of an image time-series of platelet accumulation, as plotted in the kymographs shown in FIGS. 43-45.

No significant fluctuations are shown on both the collagen-coated microfluidic surface (FIG. 43) and the surface lined with a healthy live endothelium (FIG. 44). Thus, on collagen, while there is platelet accumulation over time, there is hardly any detachment or dynamical surface interactions present. A healthy endothelium is devoid of any interaction at all. However, TNF-α stimulated endothelium results in significant fluctuations (FIG. 45), which is representative of occasional attachment and detachment of platelets (dynamics).

To define a parameter that quantitates these differences at a pixel level, a dimensionless statistical measure of dispersion is selected as a coefficient of variance (CV). The CV is defined as a ratio of standard deviation and mean. Although the CV at a representative pixel is near zero for collagen and untreated endothelium, as FIG. 46 illustrates the CV is much higher for a treated endothelium.

Figures 47, 48, 49, 50:
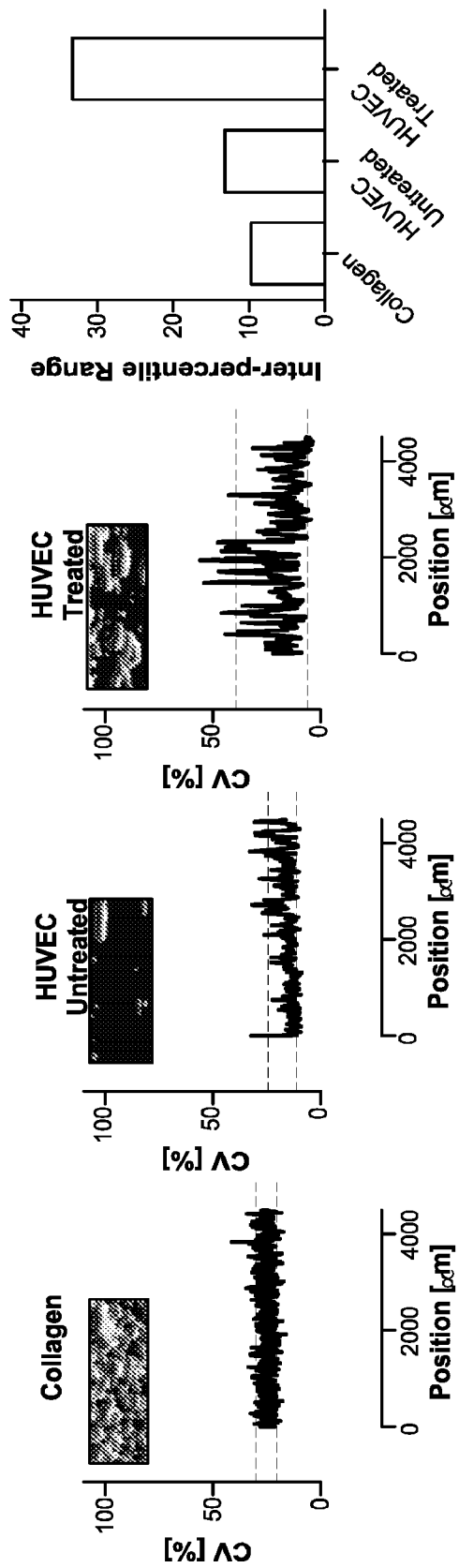
FIG. 47 shows a top image representative of a coefficient of variation (CV) colormap of a large section of a vessel, and a bottom image with a graph showing the CV across the length of the channel at a representative width location for a collagen-treated vessel.
FIG. 48 shows a top image representative of a coefficient of variation (CV) colormap of a large section of a vessel, and a bottom image with a graph showing the CV across the length of the channel at a representative width location for an untreated vessel.
FIG. 49 shows a top image representative of a coefficient of variation (CV) colormap of a large section of a vessel, and a bottom image with a graph showing the CV across the length of the channel at a representative width location for vessel treated with TNF-α.
FIG. 50 shows a graph illustrating the interpercentile range ($95^{th}$-$5^{th}$ percentile value) of the coefficient of variation (CV) plotted in the graphs illustrated in FIGS. 47-49, as a measure of depicting spatial heterogeneity in platelet accumulation.

Referring specifically to FIGS. 47-50, a visualization and analysis of platelet-endothelial spatial dynamics is illustrated. Top images are representative CV-colormaps of a large section of the vessel where each pixel in the map represents the temporal platelet dynamics (CV) on a collagen surface or vessel (untreated vs TNF-α treated, with a scale bar: 100 μm). Bottom graphs show CV across the length of the channel at representative width location for collagen (FIG. 47), untreated vessel (FIG. 48), and vessel treated with TNF-α (FIG. 49). The dotted lines are drawn at the $95^{th}$ percentile and $5^{th}$ percentile value of the CV respectively. The graph of FIG. 50 illustrates the interpercentile range ($95^{th}$-$5^{th}$ percentile value) of the CV plotted in the graphs illustrated in FIGS. 47-49, as a measure of depicting spatial heterogeneity in platelet accumulation.

FIGS. 47-50 are directed to a much larger area of the lumen, creating a 2-D image/map of the CV of all the pixels of the acquired image time-series. The resulting spatial image is reprocessed using a color map and is analysed using an intensity palette look-up table to contrast highly active versus dormant areas. This image intensity transformation enables spatial visualisation of dynamic behaviour of individual platelets, in addition to conveying an overall pattern of thrombi dynamics.

For example, FIG. 47 shows a uniform platelet adhesion pattern with a narrow range of variance on a cell free collagen surface. However, in FIG. 48, when blood is flowed over a healthy endothelium, platelets show very limited reactivity with the apical surface and, therefore, the color spectrum is almost entirely black. Nevertheless, in FIG. 49, the thrombi patterns on endothelium treated TNF-α are heterogeneous and fluctuate significantly.

Furthermore, FIG. 50 is representative of a visual analysis of the local heterogeneity within the thrombus. A plot of the CV, over the entire length of the microchannel, at a representative location along the width of the channel, provides the spatial heterogeneity or fluctuations of the dispersion parameter (CV) for a collagen coated device or an endothelium. The interpercentile range (e.g., the difference between the $95^{th}$ percentile and $5^{th}$ percentile) shows that the spatial heterogeneity also varies between the surfaces. On collagen and a healthy endothelium, there is very little variation between the surfaces. In contrast, the spatial heterogeneity is very high on a stimulated endothelium. Equation 1, described above, shows the derivation of the quantitative readout as a combination of CV and interpercentile range.

F. Immunostaining and Histology

Fluorescence microscopy is optionally performed on an endothelium that is fixed with 4% formaldehyde (from Sigma) and stained with antibodies against ICAM-1 (from Santa Cruz) and VE-Cadherin (from Santa Cruz). The endothelium is further counterstained with phalloidin and DAPI (from Invitrogen).

G. Parmodulin ("PM2") Drug Delivery

PM2 is optionally added to the endothelial cell or epithelial cell culture medium at a final concentration of 30 μM. The cells are exposed for about 4 hours. Then, the cells are stimulated with LPS (100 ng ml$^{-1}$) for about 2 hours. LPS also contains PM2 (30 μM). Blood is, then, perfused in the microfluidic device. In whole blood containing PM2, the blood is added to a final concentration of 30 μM, and is incubated for about 30 minutes before perfusion.

H. Mouse Laser Injury Model

In the above described techniques, C57BL/6J mice (about 8-12 weeks old) are used. For example, the mice are purchased from the Jackson Laboratory (Bar Harbor, Me.). Animal care and experimental procedures are performed in accordance with and under approval of the Beth Israel Deaconess Medical Center ("BIDMC") Institutional Animal Care and Use Committee.

LPS is isolated from *Escherichia coli* serotype 0111:B4 (e.g., from Sigma-Aldrich, St Louis, Mo.). The anti-platelet antibody CD42b conjugated to Dylight649 is purchased, for example, from Emfret Analytics (Eibelstadt, Germany).

A laser-induced injury model of thrombosis is optionally used to monitor thrombosis formation in cremaster arterioles and venules in response to intraperitoneal injection of LPS (e.g., 10 mg kg$^{-1}$) or vehicle (e.g., physiological saline solution). Intravital microscopy of the cremaster microcirculation is performed, with injury to a cremaster arteriolar (e.g., 30-50 μm diameter) vessel wall being induced with a Micropoint Laser System (e.g., from Photonics Instruments, Chicago, Ill.). The Micropoint Laser System is focused through a microscope objective, parfocal with the focal plane and tuned to 440 nm. Data is captured digitally in a single fluorescence channel at 647/670 nm. Data acquisition is initiated both prior to and following a single laser pulse for each injury. Images are captured using a CCD camera (e.g., from Hamamatsu) at frame rates of 1/0.2 s$^{-1}$ and 1/0.5 s$^{-1}$, for a total of 240 seconds. The microscope system is controlled and images are analyzed using Slidebook (e.g., from Intelligent Imaging Innovations, Denver, Colo.). Anti-platelet antibodies re infused into the mice prior to vessel wall injury.

Histology Lungs are harvested in 4% paraformaldehyde. Following overnight incubation, lungs re transferred to 70% ethanol. Paraffin-embedded lungs are sectioned and stained with Hematoxylin and eosin (MTS) or Masson's Trichome stain (MTS). This work is done by the histology and microscopy core at BIDMC.

I. Statistical Analysis

Unless otherwise specifically mentioned above or in the drawings, all data is presented as mean±standard error of the mean (SEM). Two-tailed P values are obtained from the statistical t-test or analysis of variance (ANOVA) to compare the means. Data analysis is optionally performed using Graphpad Prism V6.

VI. OTHER EMBODIMENTS

A. Organ-On-Chip (OOC) Device

Figure 51:
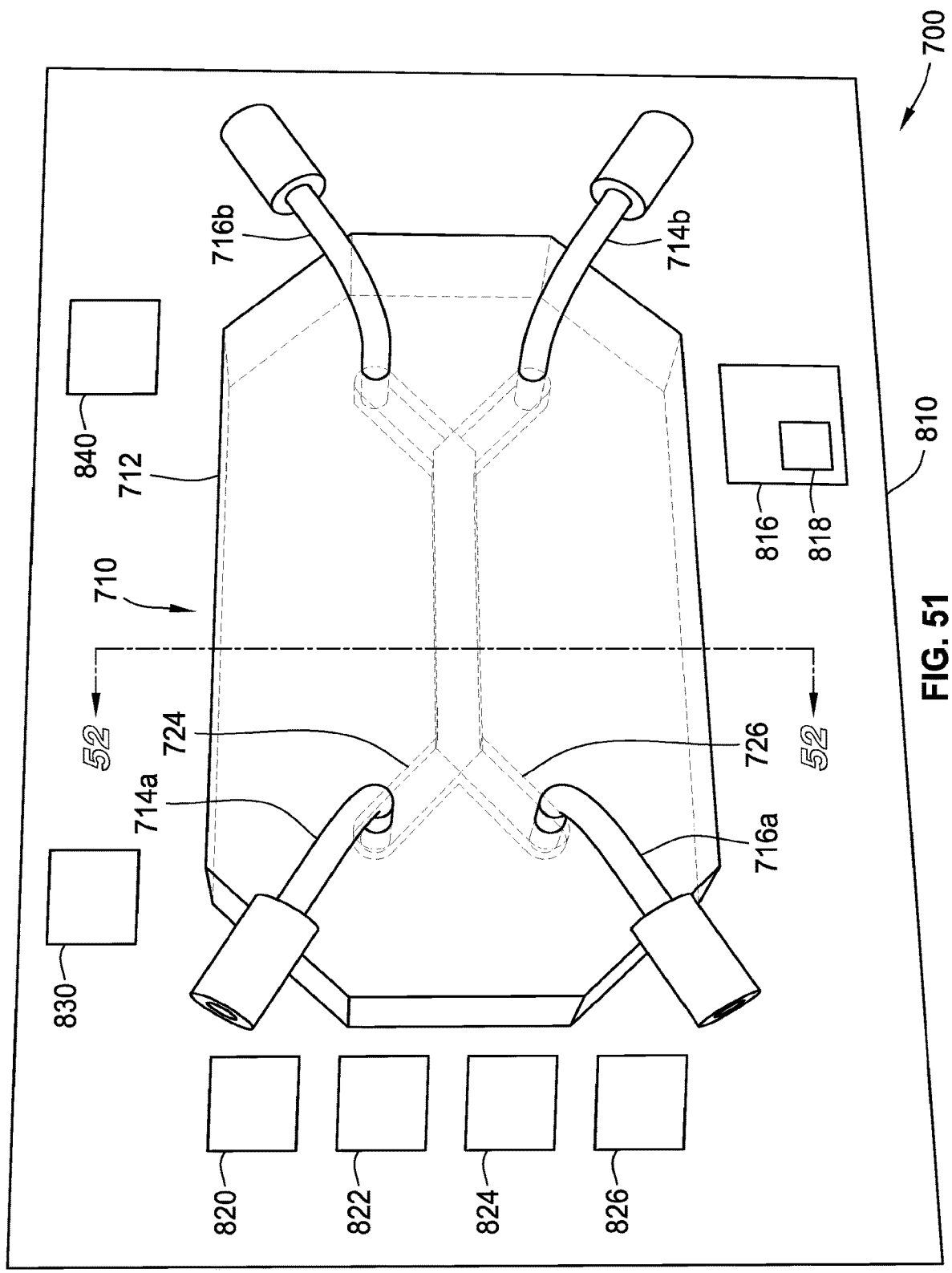
FIG. 51 illustrates an exemplary organ-on-chip (OOC) device in accordance with one embodiment of the present disclosure.
Figure 52:
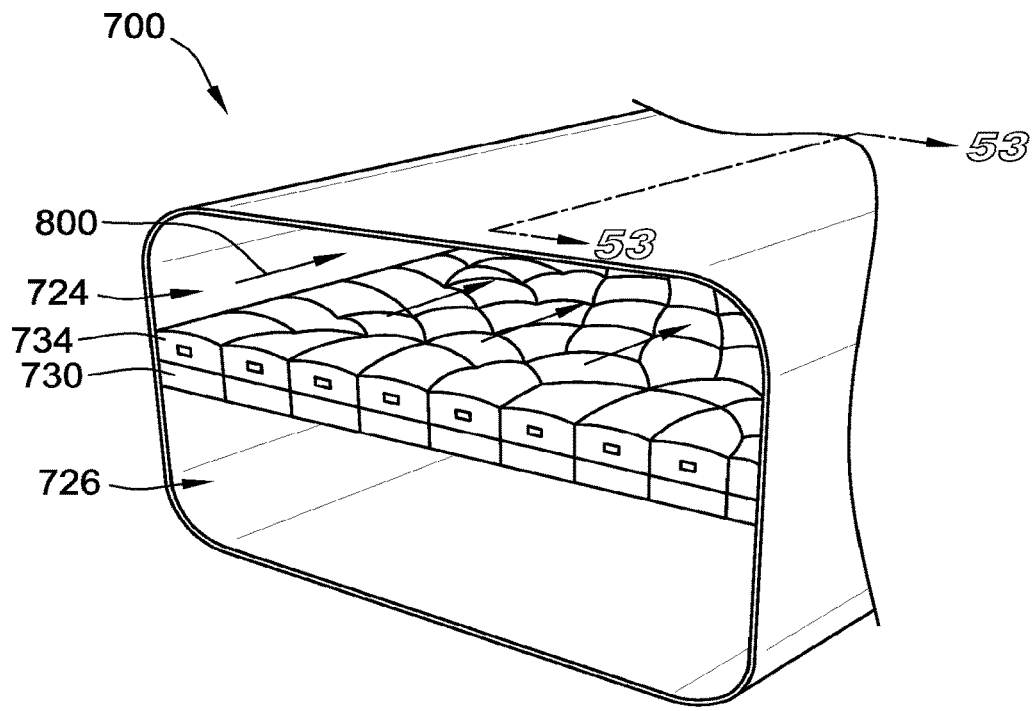
FIG. 52 is a cross-section of the organ-on-chip (OOC) device taken along line 52-52 of FIG. 51, illustrating first and second microchannels of the organ-on-chip (OOC) device.

Referring to FIGS. 51 and 52, a microfluidic system 700 is configured to function in accordance with one or more of the above-described techniques. According to the illustrated example, the microfluidic system 700 includes an organ-on-chip ("OOC") device 710. The OOC device 710 that includes a body 712 that is typically made of a polymeric material. The body 712 includes a first fluid inlet 714a and a first fluid outlet 714b. The body 712 further includes a second fluid inlet 716a and a second fluid outlet 716b. The first fluid inlet 714a and the first fluid outlet 714b allow fluid flow through a first microchannel 724. The second fluid inlet 716a and the second fluid outlet 716b allow fluid flow through a second microchannel 726.

The first microchannel 724 is separated from the second microchannel 726 by a barrier 730. The barrier 730 may be any suitable semi-permeable barrier that permits migration of cells, particulates, media, proteins, and/or chemicals between the first microchannel 724 and the second microchannel 726. For example, the barrier 730 includes gels, layers of different tissue, arrays of micro-pillars, membranes, combinations thereof, and the like. Depending on the application, the barrier 730 may have openings or pores to permit the migration of cells, particulates, media, proteins, and/or chemicals between the first microchannel 724 and the second microchannel 726. In some preferred embodiments, the barrier 730 is a porous membrane that includes a cell layer 734 disposed on at least a first surface of the membrane.

Optionally or alternatively, the barrier 730 includes more than a single cell layer 734 disposed thereon. For example, the barrier 730 includes the cell layer 734 disposed within the first microchannel 724, the second microchannel 726, or each of the first and second microchannels 724, 726. Additionally or alternatively, the barrier 730 includes a first cell layer 734 disposed within the first microchannel 724 and a second cell layer within the second microchannel 726. Additionally or alternatively, the barrier 730 includes a first cell layer 734 and a second cell layer disposed within the first microchannel 724, the second microchannel 726, or each of the first and second microchannels 724, 726. In one embodiment of the OOC device 710, the first and second microchannels 724, 726 generally have a length of less than about 2 cm, a height of less than 200 µm, and a width of less than 400 µm. More details on the OOC device 710 can be found in, for example, U.S. Pat. No. 8,647,861, which is owned by the assignee of the present application and is incorporated by reference in its entirety.

Figure 53:
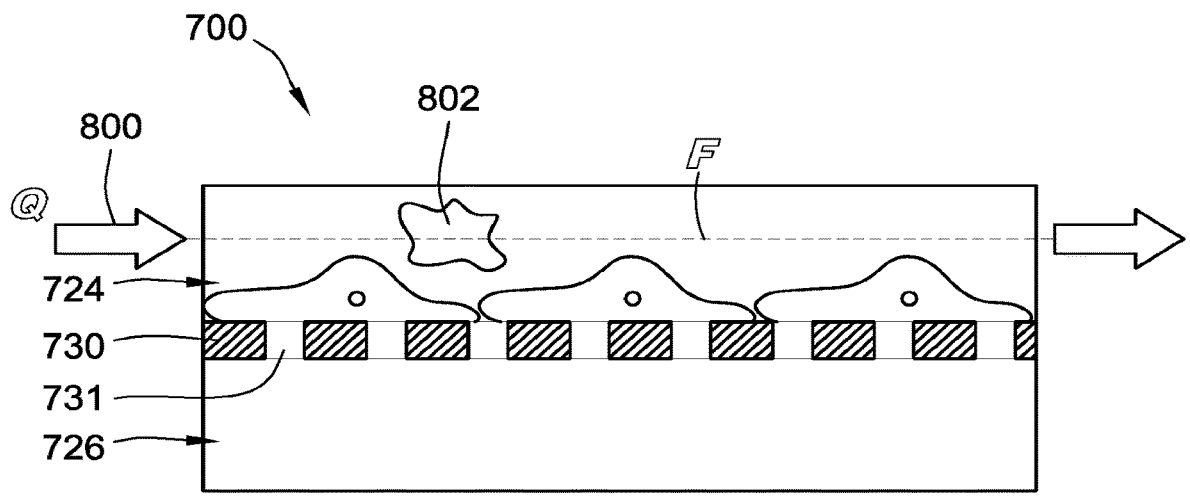
FIG. 53 is a cross-section of the organ-on-chip (OOC) device taken along line 53-53 of FIG. 52, illustrating fluid flow between the first microchannel and the second microchannel of the organ-on-chip (OOC) device of FIG. 51.

Referring to FIG. 53, the barrier 730 includes pores 731, which can have various dimensions based on the barrier 730 that is chosen. In the illustrated example, a cell layer 734 is disposed within the first microchannel 724 and on the first upper surface of the barrier 730. Fluid enters the first microchannel 724 and flows from the inlet toward the outlet of the first microchannel 724. As the fluid flows from the inlet toward the outlet of the first microchannel 724, contact between the fluid and the surface of the cells 734 exerts a shear stress on the cells 734. This shear stress deform the individual cells 734, or affect other changes in the physical or biological properties of the cells 734.

B. Exemplary Method for Determining Thrombosis Function

In accordance with the exemplary microfluidic system 700 (FIGS. 51-53), and the above-discussed techniques, an exemplary method is directed to determining a thrombosis function. The method includes flowing a fluid sample 800 over a top surface of the membrane 730, which includes a endothelial cell monolayer 734. The method further includes stimulating the fixed endothelial cell monolayer 734 to induce formation of a clot 802, the clot being formed via an interaction between the fixed endothelial cell monolayer 734 and the fluid sample 800. In response to the clot formation, a thrombosis function is determined that is associated with the fluid sample 800 and the fixed endothelial cell monolayer 734.

In accordance with an alternative embodiment, in reference to the above exemplary method, the fluid sample 800 includes platelets 804 that interact with the fixed endothelial cell monolayer 734. In this example, the thrombosis function is a function of platelets in the fluid sample 800.

In accordance with an alternative embodiment, in reference to the above exemplary method, the fixed endothelial cell monolayer is derived from one or more of (a) a fixing endothelial cell extract, (b) endothelial cell-associated proteins that are adhered to the surface, (c) a subject from which the fluid sample 800 is derived, (d) a subject that is different than a subject from which the fluid sample 800 is derived, (e) fixing an endothelial cell monolayer 734 that has been grown on the surface for a period of time, (f) healthy cells, and (g) diseased cells.

In accordance with an alternative embodiment, in reference to the above exemplary method, the fluid sample 800 includes one or more of a blood sample, a serum sample, a plasma sample, a lipid solution, and a nutrient medium.

In accordance with an alternative embodiment, in reference to the above exemplary method, the endothelial cell monolayer 734 is physically fixed by one or more of (a) exposing to air, (b) washing with alcohol, acetone, or a solvent that removes water, or lipids, (c) a chemical fixative, (d) a decellularization solvent that stabilizes surface membrane protein configuration and cytoskeleton of a cell, (e) drying, and (f) dehydration.

In accordance with an alternative embodiment, in reference to the above exemplary method, the chemical fixative is selected from a group consisting of formaldehyde, paraformaldehyde, formalin, glutaraldehyde, mercuric chloride-based fixatives, precipitating fixatives, and dimethyl suberimidate In accordance with an alternative embodiment, in reference to the above exemplary method, the method further includes measuring at least one of temporal and spatial interaction dynamics of cells in the fluid sample.

In accordance with an alternative embodiment, in reference to the above exemplary method, the cells are platelets and the spatial interaction dynamics of the cells includes at least one of (a) binding dynamics of the platelets to the fixed endothelial cell monolayer and (b) binding dynamics of the platelets to each other.

In accordance with an alternative embodiment, in reference to the above exemplary method, the method further includes storing the top surface of the membrane 730 at (a) room temperature for a predetermined period of time prior to said flowing the fluid sample 800 or (b) a temperature of about 4° C. or lower for a predetermined period of time prior to the flowing of the fluid sample 800.

In accordance with an alternative embodiment, in reference to the above exemplary method, the flowing of the fluid sample 800 is at (a) a physiological shear rate, (b) a pathological shear rate, or (c) at a shear rate of about 50 $sec^{-1}$ to about 10,000 $sec^{-1}$.

C. Exemplary Microfluidic System for Determining Thrombosis Function

In accordance with another alternative embodiment, the microfluidic system 700 is directed to determining a thrombosis function and includes a compartment in the form of the first microchannel 724. The membrane 730 has the fixed endothelial cell monolayer 734 on the top surface of the membrane 730. As such, the compartment 724 is configured to receive the fluid sample 800 flowing over the top surface of the membrane 730 such that cells in the fluid sample 800 interact with the fixed endothelial cell monolayer 734.

The microfluidic system 700 further includes a detection module 810 that is configured to detect interaction between the cells of the fluid sample 800 and the fixed endothelial cell monolayer 734. Additionally, the detection module 810 is configured to detect a function of the cells in the fluid sample 800.

In accordance with an alternative embodiment, in reference to the above exemplary microfluidic system 700, the compartment 724 includes a membrane 730 having a top surface and a bottom surface. The first microchannel 724 is a top microchannel that is separated from the second microchannel 726, which is a bottom microchannel, by the membrane 730.

In accordance with an alternative embodiment, in reference to the above exemplary microfluidic system 700, the fluid sample 800 interact with any internal surfaces of the compartment 724 or the top surface of the membrane 730. Alternatively or additionally, the fluid sample 800 flows through the bottom microchannel 726 and the fluid sample 800 interact with any internal surface of the compartment 726 or the bottom surface of the membrane 730.

In accordance with an alternative embodiment, in reference to the above exemplary microfluidic system 700, the top surface of the membrane 730 includes the fixed endothelial cell monolayer 734, and the bottom surface of the membrane 730 including adhered tissue-specific cells 814.

In accordance with an alternative embodiment, in reference to the above exemplary microfluidic system 700, the detection module 812 includes an imaging system 816 configured to provide images of interaction between the cells of the fluid sample 800 and the fixed endothelial cell monolayer 734.

In accordance with an alternative embodiment, in reference to the above exemplary microfluidic system 700, the imaging system 816 includes a time-lapse microscopy apparatus 818.

In accordance with an alternative embodiment, in reference to the above exemplary microfluidic system 700, the detection module 812 includes one or more of a wide-field holography apparatus 820, an impedance spectroscopy apparatus 822, a flow sensor apparatus 824, and a pressure sensor apparatus 826.

In accordance with an alternative embodiment, in reference to the above exemplary microfluidic system 700, the cells in the fluid sample 800 include platelets, the detection module 812 being configured to determine a function of the platelets in the fluid sample 800.

D. Exemplary System and Method for Quantifying Thrombosis

In accordance with another alternative embodiment, the microfluidic system 700 is a system for quantifying thrombosis in vitro based on physiological conditions. By way of example, the membrane 730 is in the form of a solid substrate having a top surface with the fixed endothelial cell monolayer 734. The microfluidic system 700 includes the detection module 812, which is configured to receive the solid substrate 730 and to detect spatial and temporal interaction between cells in the fluid sample 800 and the surface of the solid substrate 730 when the fluid sample 800 is flowed over the surface along a flow axis F.

The system 700 includes one or more controllers 830 that are configured to store time-lapse data of detectable signals collected from the detection module 812, the detectable signals representing spatial and temporal interaction between the cells of the fluid sample 800 and the surface of the fixed endothelial cell monolayer 734. The controllers 830 generate a kymograph from at least a portion of the stored time-lapse data, wherein a time axis of the kymograph indicates at least a portion of the time-lapse duration, a space axis of the kymograph indicating the detectable signals along the flow axis.

Based on the generated kymograph, the controllers 830 determine a rate of fluctuation in a coefficient of variation (CV) of the detectable signals to generate a temporal cell dynamics index. The controllers 830 further determine either (i) the presence of reactive cells in the fluid sample 800 when the temporal cell dynamics index is higher than a temporal control value, or (ii) the absence of reactive cells in the fluid sample 800 when the temporal cell dynamics index is no more than the temporal control value The system 700 further includes a display module 840 for displaying content that is based in part on output determined by the one or more controllers 830, wherein the content includes a signal indicative of either presence or absence of at least one of reactive cells or cell aggregation in the fluid sample 800.

In accordance with an alternative embodiment, in reference to the above exemplary system 700, the fluid sample 800 is blood and the cells are platelets.

In accordance with an alternative embodiment, in reference to the above exemplary system 700, the detectable signals are averaged across a width of the surface prior to generating the kymograph.

In accordance with an alternative embodiment, in reference to the above exemplary system 700, the width of the surface is transverse to the flow axis.

In accordance with an alternative embodiment, in reference to the above exemplary system 700, the controllers 830 are further configured to generate, from at least a portion of the stored time-lapse data, a spatial map of temporal variances of the detectable signals, each pixel of the spatial map corresponding to a time-averaged CV of the detectable signals.

In accordance with an alternative embodiment, in reference to the above exemplary system 700, the controllers 830 are further configured to determine, based on the generated spatial map, an inter-quartile range (IQR) of the map to generate a spatial cell dynamics index.

In accordance with an alternative embodiment, in reference to the above exemplary system 700, the controllers 830 are further configured to determine the presence of cell aggregation in the fluid sample 800 when the spatial platelet dynamics index is higher than a spatial control value, and the absence of cell aggregation in the fluid sample 800 when the spatial platelet dynamics index is no more than the spatial control value.

In accordance with an alternative embodiment, in reference to the above exemplary system 700, the time-lapse data is presented in the form of images.

In accordance with an alternative embodiment, in reference to the above exemplary system 700, the controllers 830 are further configured to determine cell reactivity based on a linear or non-linear function that includes spatial and temporal dynamic parameters.

In accordance with an alternative embodiment, a method is directed to quantifying thrombosis in vitro based on physiological conditions in accordance with the above exemplary system 700.

VII. EXEMPLARY EMBODIMENTS

A. Displayed Content of Display Module

Figure 62:
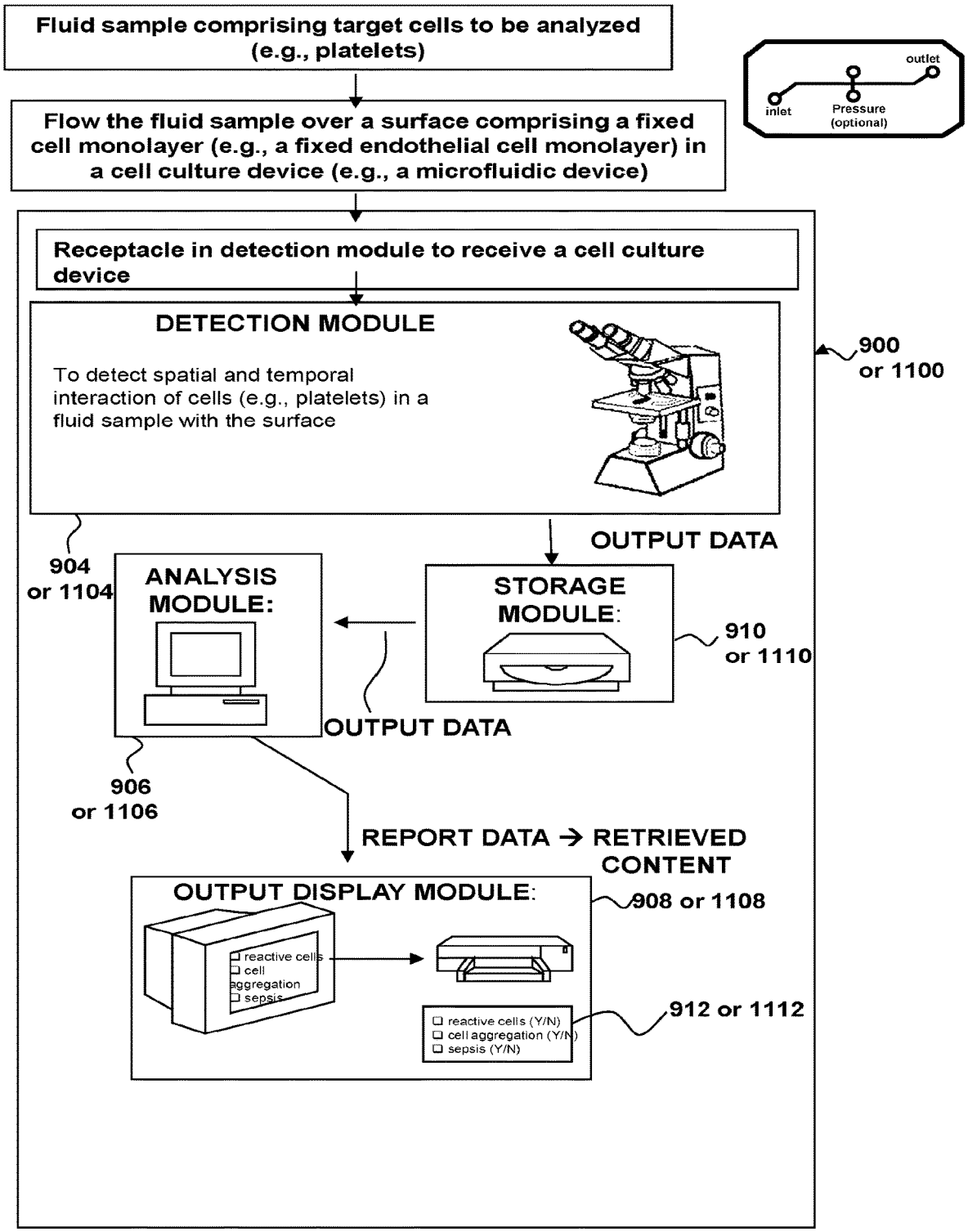
FIG. 62 is a block diagram showing an exemplary system for use in the methods described herein, e.g., for determining temporal and/or spatial dynamics of cells (e.g., platelets) binding to each other and/or a cell monolayer (e.g., an endothelial cell monolayer).
Figure 63:
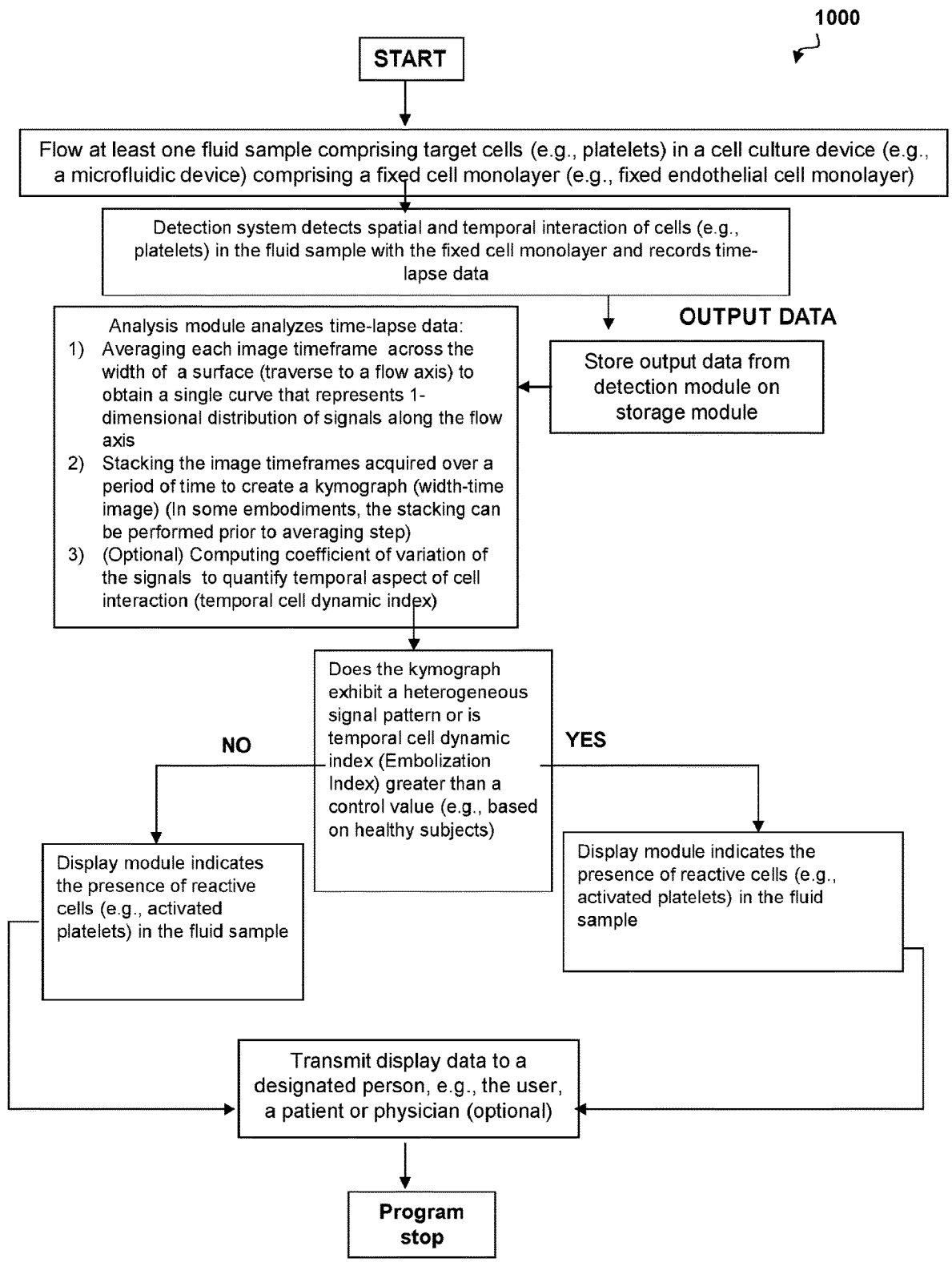
FIG. 63 is an exemplary set of instructions on a computer readable storage medium for use with the systems described herein to determine temporal dynamics of cells (e.g., platelets) binding to each other and/or a cell monolayer (e.g., an endothelial cell monolayer).
Figure 64:
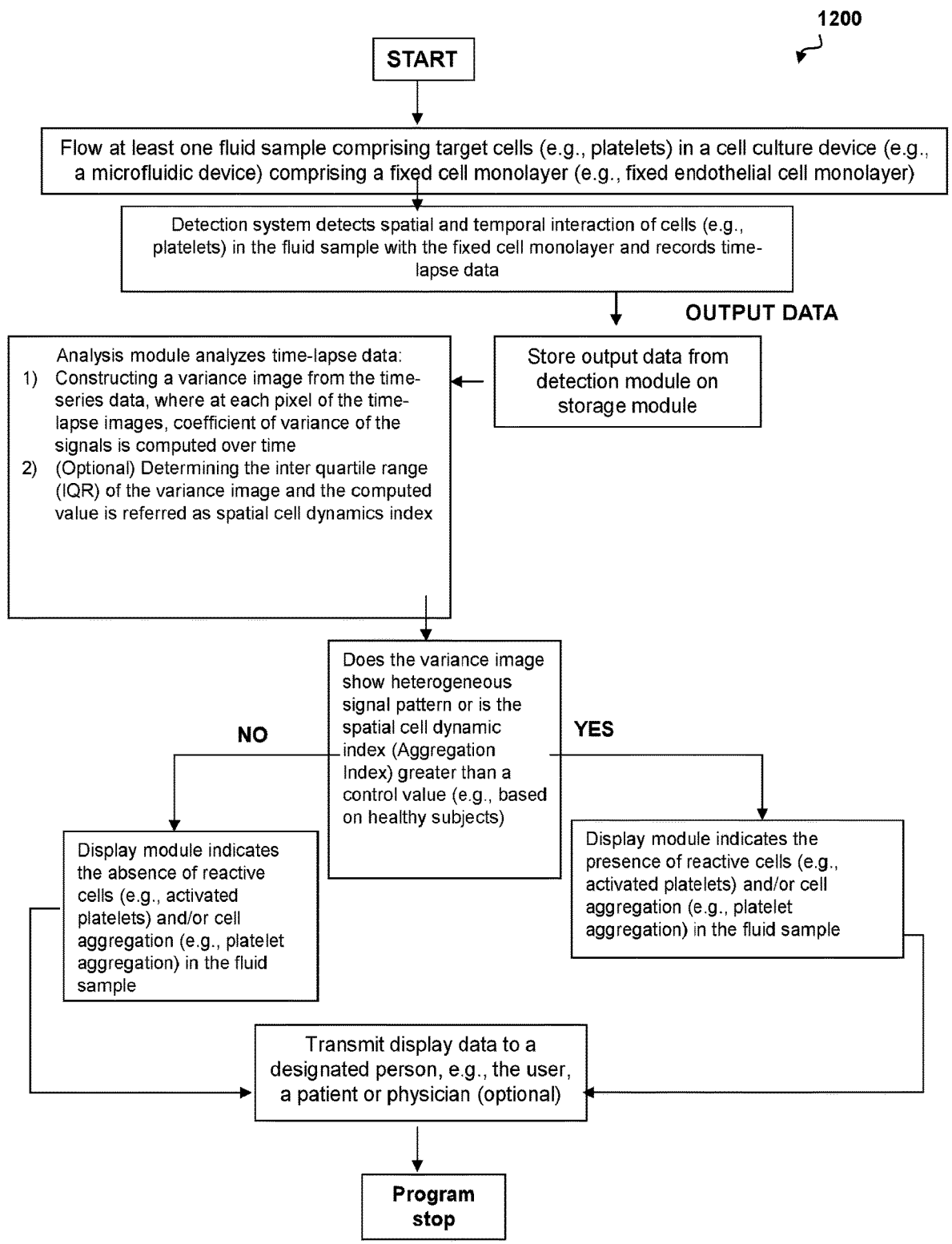
FIG. 64 is an exemplary set of instructions on a computer readable storage medium for use with the systems described herein to determine spatial dynamics of cells (e.g., platelets) binding to each other and/or a cell monolayer (e.g., an endothelial cell monolayer). In some embodiments, the exemplary set of instructions can further comprise a portion of the instructions from FIG. 63 to compute temporal dynamics of the cells (e.g., platelets) binding to each other and/or a cell monolayer. When both Aggregation (spatial) Index (FIG. 64) and Embolization (temporal) Index (FIG. 63) are used to determine cell dynamic behavior, to diagnose disease, and/or to monitor therapy, in some embodiments, both indices can be greater than their respective control values. In some embodiments, both indices can be lower than their respective control values. In some embodiments, one index can be greater than its respective control value, while another index can be lower than its respective control value. For example, samples from patients with hypercoagulable disorders can show normal/strong platelet aggregation (e.g., represented by a high Aggregation Index), but very low "embolization."

In some embodiments, referring to FIG. 62, depending on the nature of the fluid samples and/or applications of the systems as desired by users, the display module 908, 1108 can further display additional content. In some embodiments where the fluid sample is collected or derived from a subject for diagnostic assessment, the content displayed on the display module 908, 1108 can further comprise a signal indicative of a diagnosis of a condition (e.g., disease or disorder) or a state of the condition (e.g., disease or disorder) in the subject. For example, in some embodiments where the subject is diagnosed for platelet dysfunction, the content can further comprise a signal indicative of a disease or disorder induced by platelet dysfunction. Examples of the disease or disorder induced by platelet dysfunction can include, but are not limited to thrombosis, an inflammatory vascular disease (e.g., sepsis, or rheumatoid arthritis), a cardiovascular disorder (e.g., acute coronary syndromes, stroke, or diabetes mellitus), vasculopathies (e.g., malaria, disseminated intravascular coagulation), or a combination of two or more thereof.

In some embodiments wherein the fluid sample is collected or derived from a subject for selection and/or evaluation of a treatment regimen for a subject, the content can further comprise a signal indicative of a treatment regimen personalized to the subject, based on the computed temporal cell (e.g., platelet) dynamic index and/or spatial cell (e.g., platelet) dynamic index, as compared to a corresponding control value (e.g., based on healthy subjects, or from the same subject before the onset of the treatment regimen, or at an earlier time point of the treatment regimen).

The methods and/or systems described herein can provide tools to diagnose a disease or disorder induced by cell dysfunction and/or abnormal cell-cell interaction in a subject. Accordingly, another aspect described herein relates to a method of determining if a subject is at risk, or has, a disease or disorder induced by cell dysfunction or abnormal cell-cell interaction. The method comprises: (a) flowing a fluid sample of the subject over a surface comprising a fixed cell monolayer thereon; (b) detecting interaction of cells in the fluid sample between each other and/or with the fixed cell monolayer; and (d) identifying the subject to be at risk, or have the disease or disorder induced by cell dysfunction when the cell-cell interaction is higher than a control; or identifying the subject to be less likely to have a disease or disorder induced by cell dysfunction when the cell-cell interaction is no more than the control.

In some embodiments, the fixed cell monolayer used in the methods described herein can be subject-specific.

In some embodiments, the method of determining if a subject is at risk, or has a disease or disorder induced by cell dysfunction and/or abnormal cell-cell interaction can be used for diagnosis and/or prognosis of a disease or disorder induced by blood cell dysfunction (e.g., platelet dysfunction), and/or guiding and/or monitoring of an anti-platelet and/or anti-inflammation therapy. Accordingly, in some embodiments, the fixed endothelial cell monolayer can comprise a fixed endothelial cell monolayer. The fixed endothelial cell monolayer can be subject-specific. In some embodiments, the fluid sample can comprise blood cells such as platelets. Thus, a method of determining if a subject is at risk, or has a disease or disorder induced by blood cell dysfunction (e.g., platelet dysfunction) is also described herein. Non-limiting examples of the disease or disorder induced by blood cell dysfunction (e.g., platelet dysfunction) include, but are not limited to thrombosis, an inflammatory vascular disease (e.g., sepsis, or rheumatoid arthritis), a cardiovascular disorder (e.g., acute coronary syndromes, stroke, or diabetes mellitus), vasculopathies (e.g., malaria, disseminated intravascular coagulation), or a combination of two or more thereof. In these embodiments, the method can further comprising administering to the subject identified to at risk or has the disease or disorder induced by blood cell dysfunction (e.g., platelet dysfunction) an appropriate treatment (e.g., anti-platelet therapy, or an anti-inflammation therapy).

B. Compositions for Determining Cell-Cell Interaction

Compositions for determining cell-cell interaction are also described herein. In one aspect, the composition comprises (a) a solid substrate having a surface comprising a monolayer of cells of a first type thereon; and (b) a fluid sample in contact with the surface, wherein the fluid sample comprises cells of a second type.

In some embodiments, the monolayer of cells of the first type can comprise a fixed endothelial cell monolayer. In some embodiments, the cells of the second type in the fluid sample can comprise blood cells such as platelets.

In some embodiments, the fluid sample can comprise a blood sample.

The cell monolayer can comprise fixed cells (e.g., fixed endothelial cells), fixed cell extract(s) (e.g., fixed endothelial cell extract(s)), and/or fixed cell-associated proteins (e.g., fixed endothelial cell-associated proteins) that are adhered to the surface.

In some embodiments, the cell monolayer (e.g., endothelial cell monolayer) can be derived from fixing a cell layer (e.g., an endothelial cell monolayer) that has been grown on the surface for a period of time, e.g., until the cell layer reaches confluence.

The surface with which the fluid sample is in contact can be a surface of any fluid-flowing conduit disposed in a solid substrate. The solid substrate can be any solid substrate that is compatible to the fluid sample and the cell monolayer. Non-limiting examples of the solid substrate include a cell culture device, a microscopic slide, a cell culture dish, a microfluidic device, a microwell, and any combinations thereof.

In one embodiment, the surface can be a wall surface of a microchannel. In one embodiment, the surface can be a surface of a membrane. In some embodiments where the surface is a surface of a membrane, the membrane can be configured to separate a first chamber (e.g., a first microchannel) and a second chamber (e.g., a second microchannel) in a microfluidic device.

In some embodiments, the microfluidic device can be configured to comprise an organ-on-a-chip device as described herein. An exemplary organ-on-chip can comprise a first chamber (e.g., a first microchannel), a second chamber (e.g., a second microchannel), and a membrane separating the first chamber and the second chamber. In these embodiments, a first surface of the membrane facing the first chamber can comprise the cell monolayer (e.g., endothelial cell monolayer) thereon, and a second surface of the membrane facing the second chamber can comprise tissue-specific cells adhered thereon.

C. Additional Example of Applications of the Methods, Systems, and Compositions Described Herein The methods, systems, and compositions of various aspects described herein can be used to determine cell-cell interaction, e.g., but not limited to spatial and/or temporal dynamics of cells of a first type interacting with each other or with cells of a second type. In some embodiments, the methods, systems, and compositions of various aspects described herein can be used to determine blood cell dynamics (e.g., platelet dynamics).

For example, in some embodiments, the methods, systems, and/or compositions described herein can be configured to permit a blood cell-comprising fluid sample (e.g., platelet-comprising fluid sample) flowing over a more reliable and physiologically relevant endothelialized surface inflamed by a cytokine, thus mimicking the in vivo endothelium-blood cell (e.g., platelet) crosstalk environment, e.g., in a normal or diseased state. The blood cell (e.g., platelet) dynamics (e.g., adhesion, translocation and/or detachment) can be recorded and quantified, which is not possible with the existing gold standard tests. As the blood cell (e.g., platelet) function/interaction can be reproduced even when the live endothelial cells are fixed, the compositions with a fixed endothelial cell monolayer described herein can be stored under standard laboratory conditions for a period of time (e.g., days or weeks) and still remain functional. Thus, the compositions described herein can be operated near patients' bedside, e.g., in clinics or hospitals, to determine blood cell (e.g., platelet) dysfunction, e.g., for diagnosis of a disease or disorder induced by blood cell (e.g., platelet) dysfunction.

In some embodiments, the compositions described herein can further comprise tissue-specific cells. For example, in some embodiments, a microfluidic device can comprise a first chamber (e.g., a first microchannel), a second chamber (e.g., a second microchannel), and a membrane separating the first chamber and the second chamber, wherein a first surface of the membrane facing the first chamber can comprise a endothelial cell monolayer thereon, and a second surface of the membrane facing the second chamber can comprise tissue-specific cells adhered thereon. A fluid comprising blood cells (e.g., blood or blood substitute) can be introduced into the first chamber such that blood cells can interact with the endothelial cell monolayer. In some embodiments, the endothelial monolayer can be an inflamed or diseased endothelial cell monolayer. By incorporating luminal blood cell fluid transport (e.g., a fluid comprising blood cells such as platelets) over a fixed endothelial cell monolayer and live culture of tissue specific cells, a physiologically relevant in vitro model of blood cell-induced inflammation can be created to probe its pathophysiology and/or to permit drug screening.

Accordingly, in one aspect, a method for modeling a blood cell-induced disease or disorder in vitro is also described herein. Examples of a blood cell-induced disease or disorder can include, but are not limited to, thrombosis, an inflammatory vascular disease (e.g., sepsis, or rheumatoid arthritis), a cardiovascular disorder (e.g., acute coronary syndromes, stroke, or diabetes mellitus), vasculopathies (e.g., malaria, disseminated intravascular coagulation), or a combination of two or more thereof. The method comprises flowing a fluid sample comprising diseased blood cells (e.g., red blood cells, white blood cells, and/or platelets) over a surface comprising an endothelial cell monolayer (endothelium) in a cell or tissue culture device; and detecting interaction between the blood cells in the fluid sample and the endothelium, e.g., using the analytical methods and/or systems described herein to determine dynamics of blood cells binding to each other and/or to the endothelium. In some embodiments, the endothelium can be a normal endothelium. In some embodiments, the endothelium can be an inflamed endothelium.

The endothelium can comprise living endothelial cells or can be fixed as described herein. In some embodiments where a fixed endothelium is used, the disease state is induced in the endothelium prior to fixation. In some embodiments, a fixed endothelium can be used to model a disease when the disease state is a result of components in the blood that do not act on the endothelium.

In some embodiments, the diseased blood cells and/or endothelial cells can be collected from a subject diagnosed with a blood cell-induced disease or disorder.

In some embodiments, diseased blood cells and/or endothelial cells can be differentiated from induced pluripotent stem cells derived from patients carrying a blood cell-induced disease or disorder. The diseased blood cells and/or endothelial cells can then be manipulated, e.g., using genome engineering technologies such as CRISPRs (clustered regularly interspaced short palindromic repeats), to introduce or correct mutations present in the cells.

In some embodiments where normal, healthy blood cells and/or endothelial cells are used, the blood cells and/or endothelial cells can be contacted with an agent (e.g., an inflammation-inducing agent as described herein) that induces the blood cells and/or endothelial cells to acquire at least one phenotypic characteristic associated with a blood cell-induced disease or disorder.

In another aspect, a method for assessing blood substitute is also described herein. The method comprising flowing a blood substitute over a surface comprising an endothelial cell monolayer (endothelium) in a cell or tissue culture device, and detecting interaction between the blood cells in the fluid sample and the endothelium; and determining temporal and/or spatial dynamics of blood substitute cells binding to each other and/or to the endothelium using the analytical methods and/or systems described herein.

As used herein, the term "blood substitute" is a substitute for blood, which has the ability to transport and supply oxygen to cells.

In a further aspect, a method for screening for agent(s) to reduce at least one phenotypic characteristics of blood cell dysfunction (e.g., platelet dysfunction) is also described herein. The method comprises (a) flowing a fluid sample comprising diseased blood cells (e.g., increased cell adhesion to an endothelium and/or aggregation) over a surface comprising an endothelial cell monolayer (endothelium) in a cell or tissue culture device; (b) contacting the diseased blood cells and/or endothelium with a library of candidate agents; and (c) detecting response of the diseased blood cells and/or endothelium to the candidate agents to identify agent(s) based on detection of the presence of a reduction (e.g., by at least about 30% or more) in the phenotypic characteristic of blood cell dysfunction (e.g., platelet dysfunction).

In some embodiments, the endothelium can be a normal endothelium. In some embodiments, the endothelium can be an inflamed endothelium.

The candidate agents can be selected from the group consisting of proteins, peptides, nucleic acids (e.g., but not limited to, siRNA, anti-miRs, antisense oligonucleotides, and ribozymes), small molecules, and a combination of two or more thereof.

Effects of the candidate agents on the diseased blood cells and/or endothelium can be determined by measuring response of the cells and comparing the measured response with cells that are not contacted with the candidate agents. Various methods to measure cell response are known in the art, including, but not limited to, cell labeling, immunostaining, optical or microscopic imaging (e.g., immunofluorescence microscopy and/or scanning electron microscopy), spectroscopy, gene expression analysis, cytokine/chemokine secretion analysis, metabolite analysis, polymerase chain reaction (PCR), immunoassays, ELISA, gene arrays, spectroscopy, immunostaining, electrochemical detection, polynucleotide detection, fluorescence anisotropy, fluorescence resonance energy transfer, electron transfer, enzyme assay, magnetism, electrical conductivity (e.g., trans-epithelial electrical resistance (TEER)), isoelectric focusing, chromatography, immunoprecipitation, immunoseparation, aptamer binding, filtration, electrophoresis, use of a CCD camera, mass spectroscopy, or any combination thereof. Detection, such as cell detection, can be carried out using light microscopy with phase contrast imaging and/or fluorescence microscopy based on the characteristic size, shape and refractile characteristics of specific cell types.

In some embodiments, a first surface of the membrane facing the first channel comprises an endothelium adhered thereon. In some embodiments, a second surface of the membrane facing the second channel can comprise tissue-specific cells adhered thereon. As used herein, the term "tissue-specific cells" refers to parenchymal cells (e.g., epithelial cells) derived from a tissue or an organ, including, e.g., but are not limited to, lung, brain, nerve network, blood-brain-barrier, kidney, liver, heart, spleen, pancreas, ovary, testis, prostate, skin, eye, ear, skeletal muscle, colon, intestine, and esophagus. By way of example only, platelets have been contemplated to play a central role in a variety of inflammatory vascular diseases, such as sepsis, rheumatoid arthritis etc. and other vasculopathies that may involve endothelial barrier dysfunction, such as malaria, where lung or brain are involved. Accordingly, in some embodiments, the second surface of the membrane facing the second channel can comprise lung cells or brain cells (e.g., astrocytes) to create an in vitro model of malaria that incorporates blood transport and endothelial barrier function.

D. Exemplary Fluid Sample

In accordance with various aspects described herein, a fluid sample (processed or unprocessed) comprising target cells to be analyzed can be subjected to the methods and systems described herein. In some embodiments, the fluid sample can comprise a biological fluid obtained from a subject. Exemplary biological fluids obtained from a subject, e.g., a mammalian subject such as a human subject or a domestic pet such as a cat or dog, can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof.

In some embodiments, the biological fluid sample can comprise a blood sample, a serum sample, a plasma sample, a lipid solution, a nutrient medium, or a combination of two or more thereof.

The biological fluid sample can be freshly collected from a subject or a previously collected sample. In some embodiments, the biological fluid sample used in the methods and/or systems described herein can be collected from a subject no more than 24 hours, no more than 12 hours, no more than 6 hours, no more than 3 hours, no more than 2 hours, no more than 1 hour, no more than 30 mins or shorter.

In some embodiments, the biological fluid sample or any fluid sample described herein can be treated with a chemical and/or biological reagent described herein prior to use with the methods and/or systems described herein. In some embodiments, at least one of the chemical and/or biological reagents can be present in the sample container before a fluid sample is added to the sample container. For example, blood can be collected into a blood collection tube such as VACUTAINER®, which has already contained heparin or citrate. Examples of the chemical and/or biological reagents can include, without limitations, surfactants and detergents, salts, cell lysing reagents, anticoagulants, degradative enzymes (e.g., proteases, lipases, nucleases, collagenases, cellulases, amylases), and solvents such as buffer solutions.

In some embodiments, a fluid sample can comprise certain cells isolated from a biological sample and resuspended in a buffered solution or culture medium. For example, fractions of blood or platelets can be isolated from a blood sample and resuspended in a buffered solution or culture medium. As used herein, the term "culture media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

E. Example 1. Development of a Microfluidic Platelet Function Assessment Interaction (µPFA) Devices/Assays In one aspect, microfluidic platelet function assessment (µPFA) devices comprising or consisting essentially of at least one layer or multiple layers (e.g., at least two layers or more) of microfluidic chambers, separated by one or more porous membranes, were developed. The porous membranes can act as a biomimetic interstitium and comprise living or fixed cells adhered thereto. In some embodiments, at least one chamber can have a monolayer of endothelial cells (normal or cytokine activated; live or fixed) and/or extracellular matrix proteins, such as collagen, and the chamber itself can be perfused with whole blood (a biomimetic blood vessel—"vascular chamber") (FIG. 54A). The monolayer of endothelial cells and/or extracellular matrix proteins can be adhered to the side of the membrane facing the chamber and/or at least one or more of the chamber fluid-contact surfaces (e.g., a portion of the chamber fluid-contact surface or entire chamber fluid-contact surface). In some embodiments, the vascular chamber can comprise or consist essentially of a microchannel dimensioned to be comparable to an arterial blood vessel. For example, in one embodiment, the microchannel can be a rectangular microchannel equivalent in size to a ~125 µm size arterial blood vessel. In one embodiment, the microchannel can have a width of about 400 µm and a height of about 100 µm (FIGS. 54B-54C).

In some embodiments, the µPFA devices can comprise a second chamber separating from the first chamber by a porous membrane. The second chamber can comprise cultured cells of interest (e.g., but not limited to astrocytes, pericytes, hepatocytes, respiratory epithelial cells, and any combinations thereof) that exhibit the functionality of a tissue of interest (FIG. 54D). The entire device, therefore, can represent a physiologically relevant, three dimensional, organ system that permits blood flow and can enable dynamic interaction of blood cells such as platelets with the endothelium and its impact on the perivascular cells, maintained in the device.

In some embodiments, the vascular coating (e.g., the monolayer of endothelial cells and/or extracellular matrix proteins that are in contact with flowing blood) can also mimic inflammatory endothelial conditions (e.g., endothelial dysfunction) by culturing the cells in the presence of cytokines such as tumor necrosis factor alpha (TNF-α) (FIG. 54E).

The μPFA devices described herein can be utilized at patients' bedside, e.g., for example, to analytically measure the spatiotemporal dynamics of platelets in whole human blood at a user-designated flow rate (shear stress). In some embodiments, no more than 0.5 ml of blood is needed for each assay using the μPFA devices described herein.

This is one of the key departure and advancement from the existing instruments and analytical devices that are currently applied to measure platelet function and reactivity, because the existing instruments and analytical devices do not incorporate shear stresses, blood vessel geometries, and interactions with inflamed endothelium or perivascular tissue.

In some embodiments, to assess platelet function using one or more embodiments of the μPFA devices described herein, human whole blood can be drawn in standard 3.2% sodium citrate vacutainers, e.g., by phlebotomy, and the assay can be performed within a period of time of the blood draw. In one embodiment, the assay can be performed within 6 hours of the blood draw. The collected blood can be stored in a reservoir attached to an inlet of the μPFA devices described herein and introduced into the "vascular chamber," for example, via a syringe pump, at a designated flow rate (shear stress) (FIG. 54A). The blood can be recalcified, e.g., using 100 mM calcium chloride and/or 75 mM magnesium chloride solution (100 μL/mL blood), after introduced into the "vascular chamber" of the device. In some embodiments, the blood can be recalcified about 2 minutes after the microfluidic experiments begin.

In some embodiments, platelets in a blood sample can be fluorescently labeled. In some embodiments, CD41 conjugated antibody can be used to label platelets. Imaging can be automated to acquire and stitch multiple image tiles (e.g., about 5-10 image tiles) along the length of the chamber every certain period of time (e.g., every 15 or 30 seconds). Image processing and analysis can be done using any art-recognized programs, e.g., but not limited to, Matlab, ImageJ and MSExcel.

For measurement of the spatiotemporal dynamics of platelet interaction, mathematical algorithms that quantitate the dynamical interactions between the platelets and the fixed endothelial cell monolayer (e.g., cytokine stimulated fixed endothelial cell monolayer) were developed as described in Example 1. Characteristic spatial and temporal indices of platelet dynamics computed based on acquired images of platelet interaction in the devices can be patient-specific, e.g., when patient-specific blood sample and/or patient-specific endothelial cells are used in the devices described herein. Accordingly, in some embodiments, these spatial and temporal indices of platelet dynamics can be used as prognostic or diagnostic markers of platelet-related diseases and/or to help in modulating antiplatelet therapy to prevent recurrent thrombosis or bleeding. In some embodiments, these indices can be used as quantitative markers of drug efficacy or toxicity, when the devices described herein are used for drug or small molecule screening (e.g., novel drug compounds). Thus, in some embodiments, these indices can be used to determine drug toxicology.

F. Example 2. Exemplary Quantitative Algorithms for Computing Platelet Adhesion Kinetics and/or Dynamics This Example describes exemplary embodiments of mathematical algorithms that each can used alone or in combination to quantitate the dynamic interactions between platelets and one or more natural and/or artificial surfaces. In some embodiments, the natural and/or artificial surface can form a wall portion or entire wall on all sides of the "vascular chamber" of the μPFA devices as described herein. The natural and/or artificial surface can be coated with extracellular matrix molecules (e.g., collagen), cultured with an endothelial cell monolayer (e.g., live or fixed cells with or without cytokine stimulation), and/or a bare surface of the device (e.g., PDMS).

Figure 55:
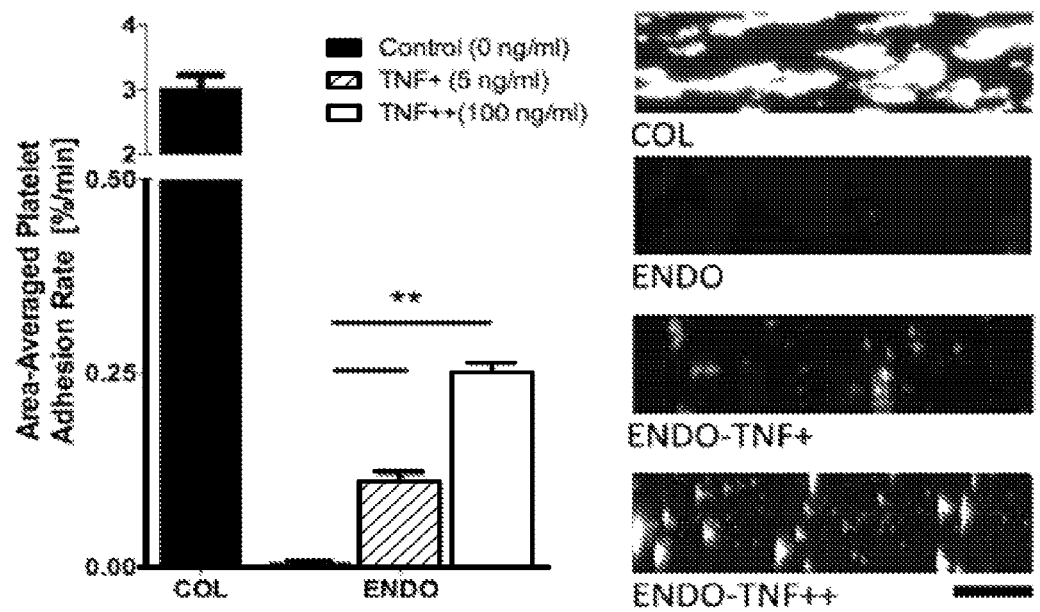
FIG. 55 is a set of data showing platelet adhesion on different surfaces. (Left panel) Bar graph showing area-averaged platelet adhesion rate on collagen, unstimulated endothelium and cytokine-stimulated endothelium. (Right panels) Snapshots of a section of the vascular chamber after 15 minutes of whole blood flow containing labeled platelets. Scale bar=50 μm. $P<0.001$
Figure 56:
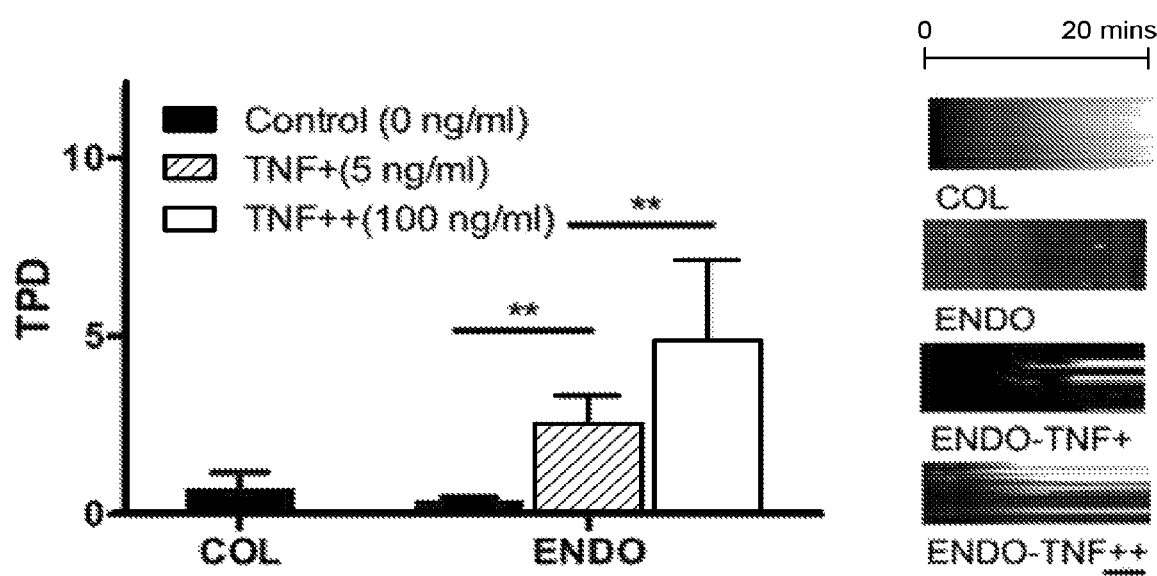
FIG. 56 is a set of data showing temporal dynamics of platelets interacting with different surfaces. (Left panel) Bar graph showing Temporal Platelet Dynamics (TPD) indices varying with different surfaces, namely, collagen, unstimulated endothelium and cytokine-stimulated endothelium. (Right panels) Kymographs of a section of the vascular chamber perfused with whole blood containing labeled platelets. Scale bar=50 μm (vertical direction). $P<0.001$
Figure 57:
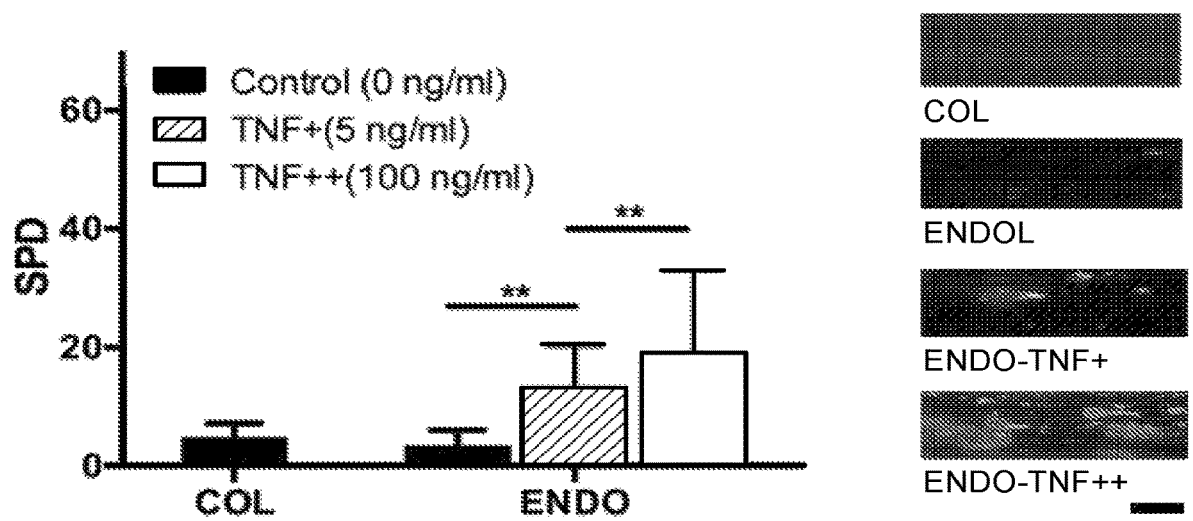
FIG. 57 is a set of data showing spatial dynamics of platelets interacting with different surfaces. (Left panel) Bar graph showing Spatial Platelet Dynamics (SPD) indices varying with different surfaces, namely, collagen, unstimulated endothelium and cytokine-stimulated endothelium. (Right panels) Time-averaged coefficient of variation (CV) maps of a section of the vascular chamber perfused with whole blood containing labeled platelets. Scale bar=$P<0.001$

Adhesion was almost completely suppressed on human umbilical vein endothelial cell (HUVEC)-coated chambers or channels, indicating that platelets are not adhering and are mimicking transport in vivo inside a healthy blood vessel (FIG. 55). However, TNF-α stimulated HUVECs (TNF+; TNF++) caused an increase in platelet adhesion and the HUVECs treated with a higher concentration of TNF-α caused a higher increase in platelet adhesion as compared to the HUVECs treated with a lower TNF-α concentration, indicative of an active and dynamic endothelial-platelet crosstalk under inflammatory conditions. However, these adhesion rates were still significantly lower when compared to a collagen surface, which is one of the most potent natural platelet agonist.

Figure 58:
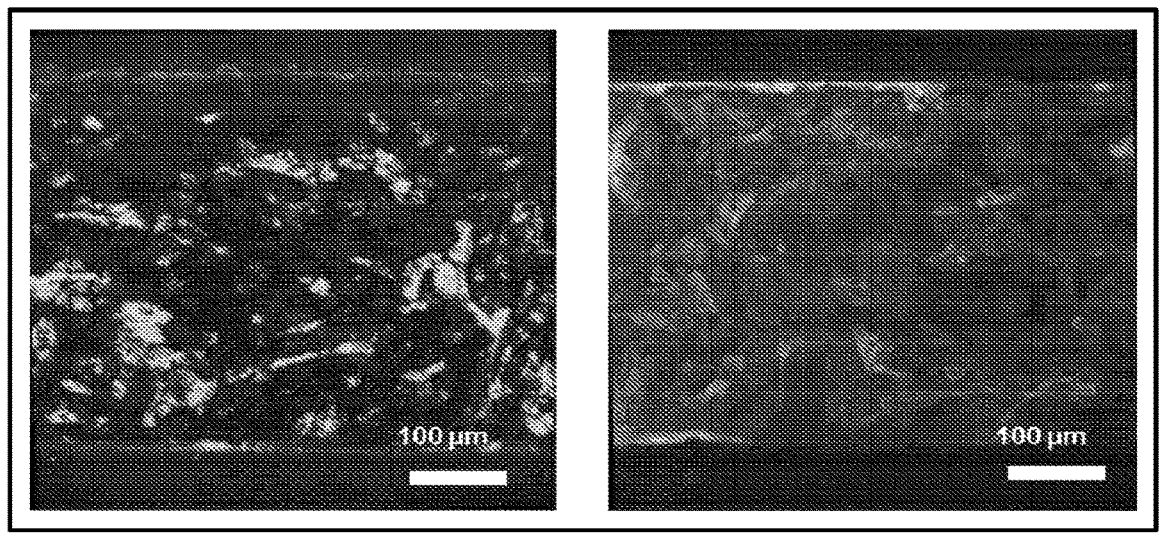
FIG. 58** is a set of micrographs showing formaldehyde-fixed human umbilical vein endothelial cells (HUVECs) in the device according to one or more embodiments described herein. (Left panel) von Willebrand factor staining (green). (Right panel) Tissue factor (TF) staining (green).
Figure 59A:
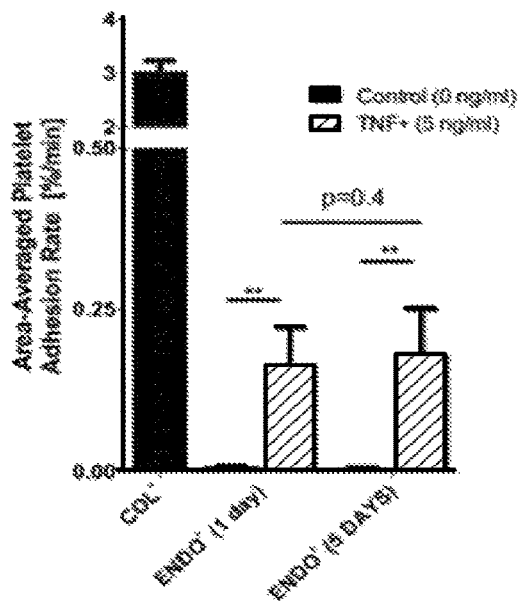
FIGS. 59A-59C are bar graphs showing area averaged platelet adhesion (FIG. 59A), Temporal Platelet Dynamics (TPD) (FIG. 59B) and Spatial Platelet Dynamics (SPD) (FIG. 59C) of platelets over collagen (COL*) and endothelium fixed for 1 day or 5 days (ENDO*). **P<0.001

G. Example 3. A Fixed Endothelialized Surface as a Physiologically Relevant Activator for Platelet Function Analysis To increase practicality and reliability of the μPFA devices so that it can also be utilized at the patient bedside environment, such as room temperature, variable humidity etc. and stored for longer periods, the inventors have discovered that platelet adhesion and dynamics can be similarly reproduced over an endothelial cell monolayer that has been fixed, for example, with 3% formaldehyde, as compared to a live cultured layer. Without wishing to be bound by theory, when the endothelium is fixed, it can still conserve the expression of many procoagulatory proteins such as vWF and tissue factor, that results in a spatially and temporally heterogeneous surface, like in vivo or live cells (FIG. 58). This novel physiologically relevant surface, heterogeneously presenting procoagulant molecules such as vWF and tissue factor, can allow a more accurate and patient-specific platelet function analysis. This surface is significantly different from a uniform monolayer of collagen that is classically used in existing flow chambers for analyzing platelet function and thrombosis. To demonstrate reliability of measuring platelet function over this fixed endothelial surface, platelet adhesion rate was measured on fixed HUVECs (ENDO*) and kept for 1 day or 5 days. It was determined that relative to the control (no treatment with TNF-α prior to fixation), the adhesion rates of platelets were significantly higher when the endothelial cells were treated with TNF-α at 5 ng/ml physiological concentration, followed by paraformaldehyde fixation (TNF+) (FIG. 59A). Yet, the fixed endothelial surface was much less adhesive than fixed collagen surface (COL*). In addition, the TPD (FIG. 59B) and SPD (FIG. 59C) analysis as described in Example 2 showed similar trends, that is, platelet dynamics over treated and fixed endothelium was elevated relative to fixed collagen or untreated, fixed endothelium.

Figure 59B:
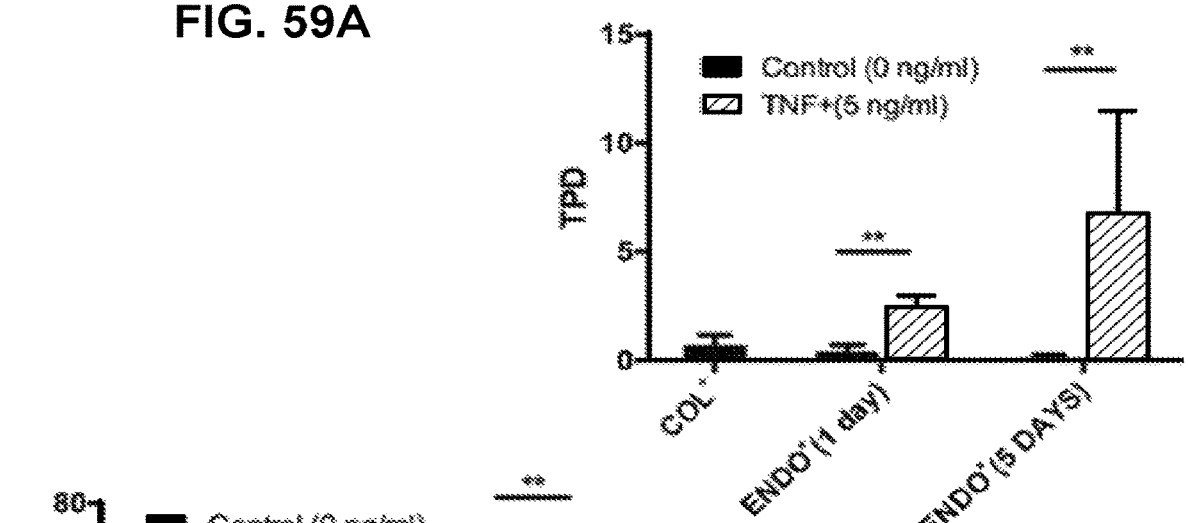
Figure 59C:
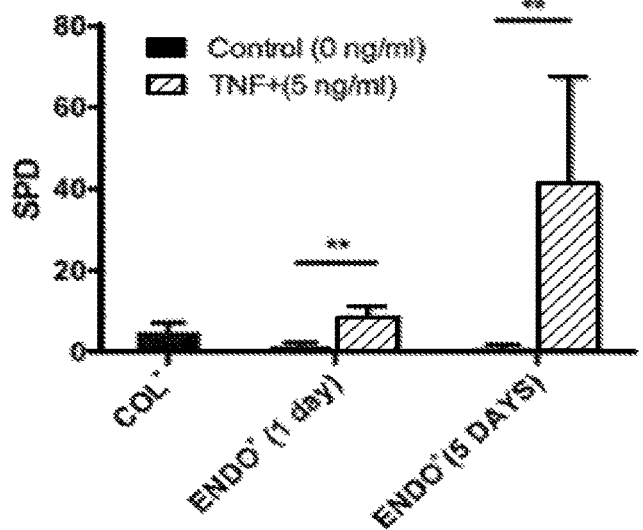

While the devices stored for 5 days at 4° C. showed increased dynamic behavior, as compared to when they were stored for only a day, the difference relative to the controls was still significant (FIGS. 59A-59C). Without wishing to be bound by theory, fixation with paraformaldehyde can be partially reversible, and/or the endothelial surfaces can have undergone morphological change over time impacting the dynamics. As shown in FIG. 59A, longer storage time does not appear to significantly affect total adhesion.

Figure 60:
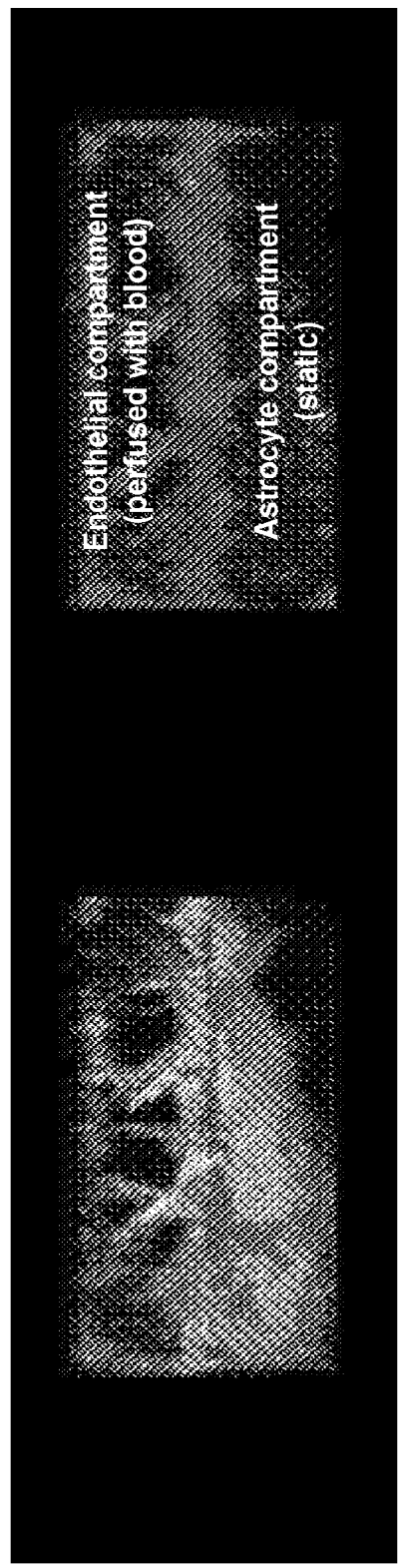
FIG. 60 is a set of confocal images showing a cross-section of a two-compartment organ-on-a-chip with co-cultures of HUVECs (top compartment) and human astrocytes (bottom compartment). The HUVECs and astrocytes were both treated overnight with 100 ng/ml TNF-α. The endothelial compartment (in which the endothelial cells were cultured on all walls of a channel) was perfused with whole blood for about 15 minutes. (Left panel) Platelets (red) were observed to be mainly on the walls of the endothelial compartment, while fibrin has formed mostly in the static (no shear) astrocyte compartment due to the reaction between blood fibrinogen and thrombin. The fibrin passed through the endothelial compartment (high shear). (Right panel) F-actin/nuclear staining shows astrocyte localizations on the membrane and the floor of the bottom compartment.
Figure 61:
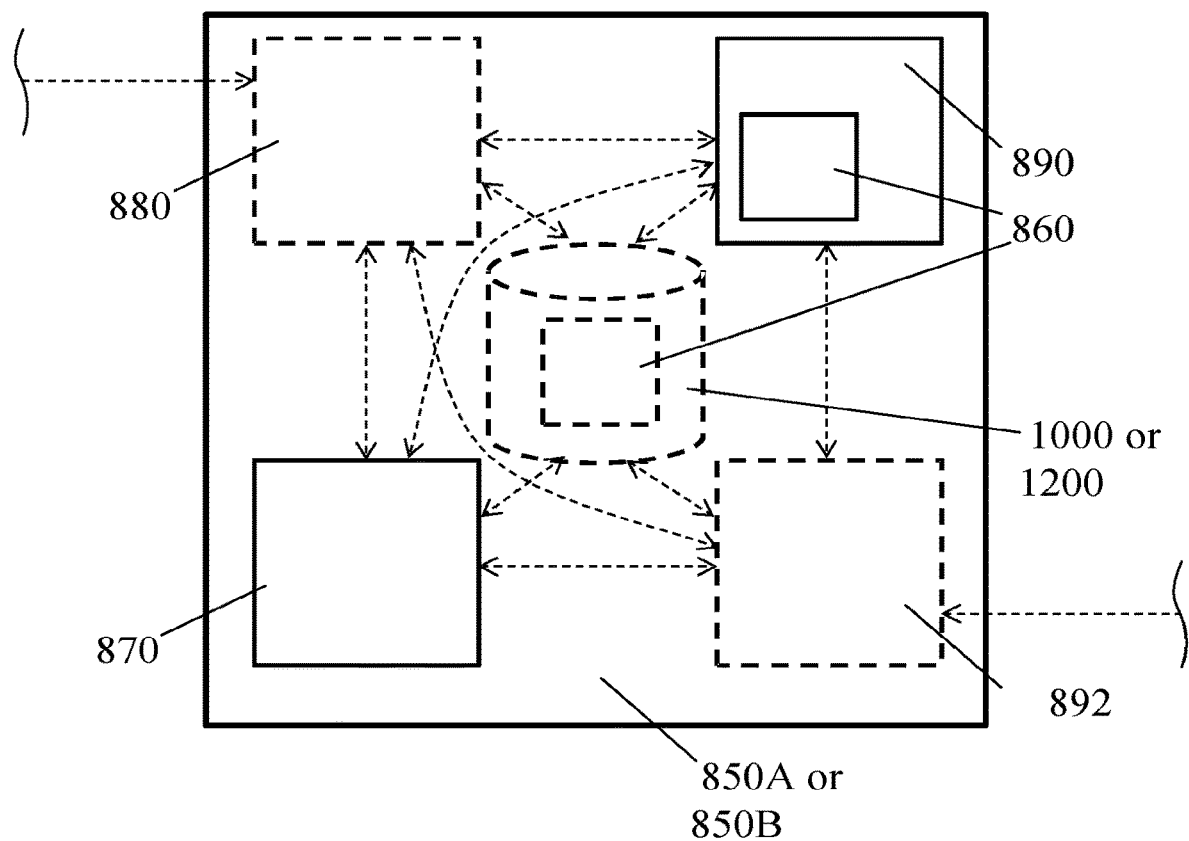
FIG. 61 is a block diagram showing an exemplary system for use in the methods described herein, e.g., for determining temporal and/or spatial dynamics of cells (e.g., platelets) binding to each other and/or a cell monolayer (e.g., an endothelial cell monolayer).

H. Example 4. Platelet Analysis on an Organ-On-A-Chip Integrated with Luminal Whole Blood Transport Using a blood-brain-barrier-on-a-chip as an example, in one embodiment, the μPFA device can comprise a first chamber and a second chamber, wherein the first chamber and the second chamber are separated by a porous membrane. The first chamber can comprise live cultured astrocytes, while the second chamber can comprise endothelial cells. In some embodiments, at least one or all of the walls (including the side of the membrane facing the second chamber) can be lined with an endothelial cell monolayer. The endothelial cells can be treated with or without a pro-inflammatory factor. In this Example, both the astrocytes and the endothelial cells were treated with TNF-α prior to exposure to blood perfusion, thus creating an inflammatory blood-brain-barrier-on-a-chip model including whole blood transport that can be utilized, for example, for the study of thrombosis, platelet activation, aggregation, platelet-endothelial and platelet-epithelial crosstalk (FIG. 60). Platelets were observed to be mainly on the walls of the endothelial compartment, while fibrin has formed mostly in the static (no shear) astrocyte compartment due to the reaction between blood fibrinogen and thrombin. The endothelium shown in FIG. 60 is a living cell culture without fixation. However, in some embodiments, the endothelium can be fixed to create a blood-brain-barrier-on-a-chip model.

I. Example 5. A Platelet Function Assessment Microdevice for Quantitative Analysis of Dynamic Platelet Interactions with Endothelium Under Flow Activation, aggregation, adhesion, translocation and embolization of platelet-rich thrombi are finely controlled dynamical processes that occur during hemostasis and thrombosis as a result of vessel wall injury or vascular inflammation. Due to the inherent complexity in the way platelets interact with the vessel wall, it is challenging to study all aspects of platelet function in a comprehensive, controlled and reproducible way. In one aspect, described herein is a biomimetic microfluidic blood perfusion assay where large-scale, spatiotemporal fluorescence imaging and statistical algorithms are applied to measure and quantify platelet-endothelial dynamics, independent of fluorescence intensity. The device comprises, essentially consists of, or consists of a set of microfluidic channels in which human umbilical vein endothelial cells (HUVECs) are cultured with or without various concentrations of one or more inflammatory cytokine, e.g., Tumor Necrosis Factor-α (TNF-α). The channels are then perfused with human whole blood containing fluorescently labeled platelets at a shear rate of about 750 s$^{-1}$. Platelet-rich thrombi form and dissociate on the endothelial cell surface over a 15 min time course and the dynamics of platelet aggregation and thrombus embolization are quantified by analyzing temporal and spatial variances in the fluorescent signal. This analysis revealed a TNF-α dose-dependent increase in both the spatial and temporal dispersion (heterogeneity) of interactions between living platelets and endothelium in the device.

In contrast, these spatiotemporal dynamics were absent when platelets interacted with healthy endothelium or a cell free, collagen-coated surface that is commonly used to analyze platelet activation and thrombus formation in most existing flow chambers. The device and quantitative methods described here represent a valuable tool for analyzing platelet-endothelial interactions under pathophysiological conditions relevant for thrombosis research, toxicology, drug screening, and clinical diagnostics.

Platelet hyper-reactivity plays a central role in the etiology of various cardiovascular diseases and vascular disorders, including acute coronary syndrome, stroke, pulmonary embolism, and diabetes. Platelet activation also contributes to the failure of implanted cardiovascular and extracorporeal devices, such as pumps, arterial stents and artificial valves. The important role that platelets play in multiple pathologies has resulted in the development of a wide array of antiplatelet drugs over the last two decades. For these reasons, it has become increasingly important to measure platelet function in patients reliably and accurately in laboratories for screening, diagnosis, and monitoring of antiplatelet therapy, as well as for predicting thrombosis or recurrent bleeding. Conventional clinical tests, such as light transmission aggregometry or viscoelastic platelet function analysis, have been indispensable in unraveling much of what is currently know about platelet biology and its contribution to thrombosis. However, these assays are limited in that they often do not incorporate relevant fluid mechanics or physiological interactions with the endothelial surface, which are key determinants of thrombosis.

Parallel plate-flow chambers are macroscale devices that are widely used to measure thrombus formation and platelet adhesion kinetics; however, they require large sample volumes for analysis and usually do not incorporate an endothelium. While previous studies have reported application of arterial shear stresses in microfluidic devices to show that thrombus formation, platelet adhesion and aggregation can be visualized and measured on a variety of prothrombogenic surfaces using small volumes of whole blood or plasma, these microfluidic platelet function assays do not permit analysis of the contributions of platelet interactions with endothelium or a fixed endothelium that lead to complex dynamics in which platelets tether, adhere, aggregate, detach, and/or translocate in space and time, as they do in vivo.

J. Other Examples

In one aspect, described herein is a biomimetic platelet function assessment device that permits robust and quantitative analysis of how endothelial inflammation affects platelet dynamics during thrombosis under flow in vitro. The device, being able to emulate relevant features of an in vivo blood vessel, includes many essential mediators of thrombosis upon stimulation (FIGS. 65A-65B). Analysis shows that the integrated interplay between platelets, thrombi, the vessel wall, blood-borne factors and flow dynamics can be analyzed in the integrated system-level assay (FIG. 65C).

This new microfluidic method can therefore be used in a variety of applications relevant for thrombosis research and clinical practice.

Blood Samples.

Citrated human blood (Research Blood Components, Cambridge, Mass.) was used within 5 hours of blood draw, to minimize pre-analytical effects on platelet function. Platelets were labeled with human CD41-PE antibody (10 µl/ml, Invitrogen) directly added to the blood and incubated at room temperature for 10 min. When analyzing the formation of fibrin, blood samples were added with 15 µg/ml of fluorescently labeled fibrinogen (Alexa 488, Invitrogen). The citrated blood was recalcified 2 minutes after the beginning of each experiment by adding 100 µl/ml of a solution containing 100 mM calcium chloride and 75 mM magnesium chloride to the blood.

Cell Culture.

Human umbilical vein endothelial cells (HUVECs, Lonza) were cultured in Endothelial Growth Medium-2 (EGM-2, Lonza) and used between passages 3 and 7. Before seeding HUVECs in the devices, the microchannels were pre-treated with 1% (3-aminopropyl)-trimethoxysilane in phosphate-buffered saline (PBS) for 10 min, flushed sequentially with 70% ethanol in water and 100% ethanol, and then incubated at 80° C. for two hours before rat tail collagen I (100 µg/ml in PBS; BD Biosciences) was introduced in the channels. Some of the devices were used with the collagen coating alone (without cells) after incubation overnight at 37° C. and flushing of the channels with EGM-2. In other studies for comparison, HUVECs ($12.5 \times 10^6$ cells/ml) were introduced into the collagen-coated channels and incubated for 20 min at 37° C. to promote cell attachment before a second similar HUVEC suspension was then introduced and the devices were incubated upside down for an additional 20 min to seed the cells on the ceiling and walls of the microfluidic channels. Channels were then flushed with EGM-2 and the devices were incubated at 37° C. under 5% $CO_2$ for 24 hours to promote HUVEC monolayer formation on all exposed surfaces of the microchannel. In some cases, the medium was supplemented with one or more inflammatory cytokines (e.g., 5 or 100 ng/ml TNF-α (Sigma)) to activate the HUVEC monolayer. Fluorescence microscopy was performed on endothelium that was fixed with 4% formaldehyde (Sigma) and stained with antibodies against TF (Santa Cruz), vWF (Abcam), VE-Cadherin (Santa Cruz), followed by counterstaining with phalloidin and DAPI (Invitrogen).

Microfluidic Device Design.

The microfluidic platelet function assessment device was designed to operate at an arterial shear rate of 750 $sec^{-1}$ (30 dynes/$cm^2$), for example, by maintaining the flow rate at 30 µl/min using a syringe pump. The flow rate can vary with the channel dimensions and/or fluid property to maintain substantially similar ranges of the arterial shear rate. If lower flow rates are used, red blood cell sedimentation can occur, whereas undesirably large volumes of human donor blood are required if higher flow rates are utilized. The channel dimensions were determined such that they enable real-time optical microscopic imaging using a moderate magnification (20×, 0.4 N.A.) objective. For these practical reasons, and to mimic the size of a small blood vessel, the microdevice contains a microchannel that is 400 µm wide, 100 µm high, and 2 cm long (FIG. 65A); the hydraulic diameter of this channel is equivalent to a 160 µm diameter circular arteriole. Six of these channels were fit on a standard (75×25 mm) glass slide, allowing high assay throughput and replicates on the same chip for testing assay reproducibility (FIG. 65B).

Engineering of an Endothelial Lining in the Microchannel.

Figure 71A:
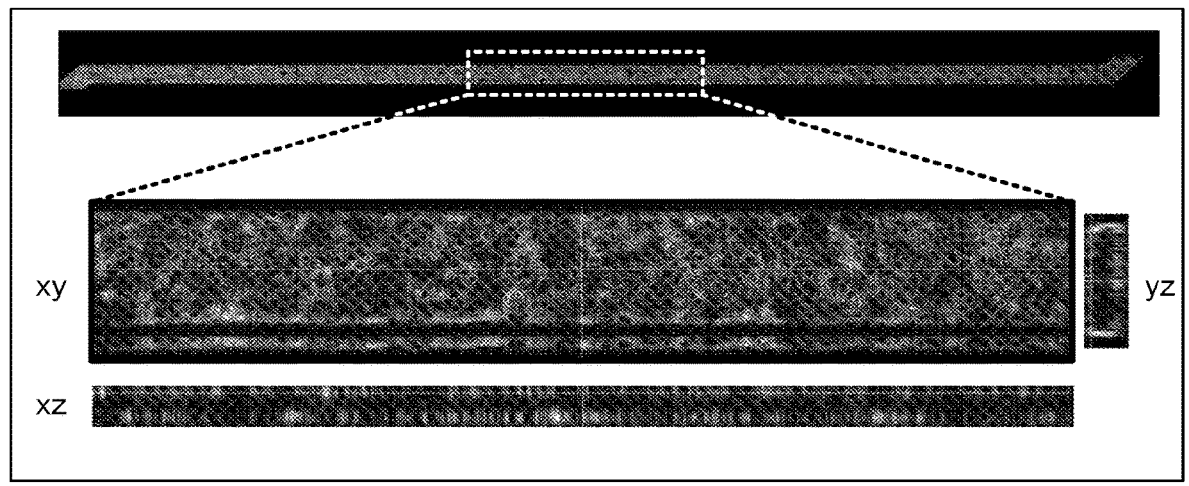
FIGS. 71A-71B depict the engineering of one embodiment of a responsive endothelium-lined microfluidic channel described herein.
Figure 71B:
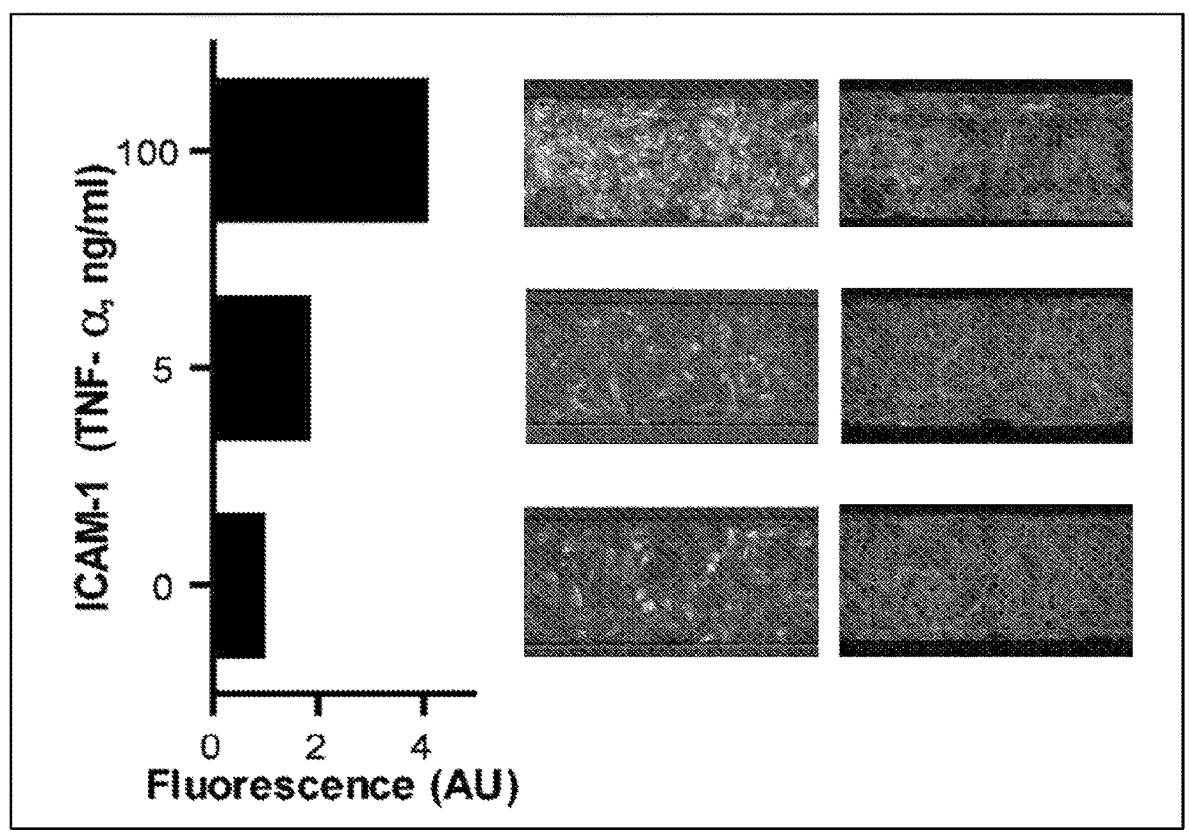
Figure 72:
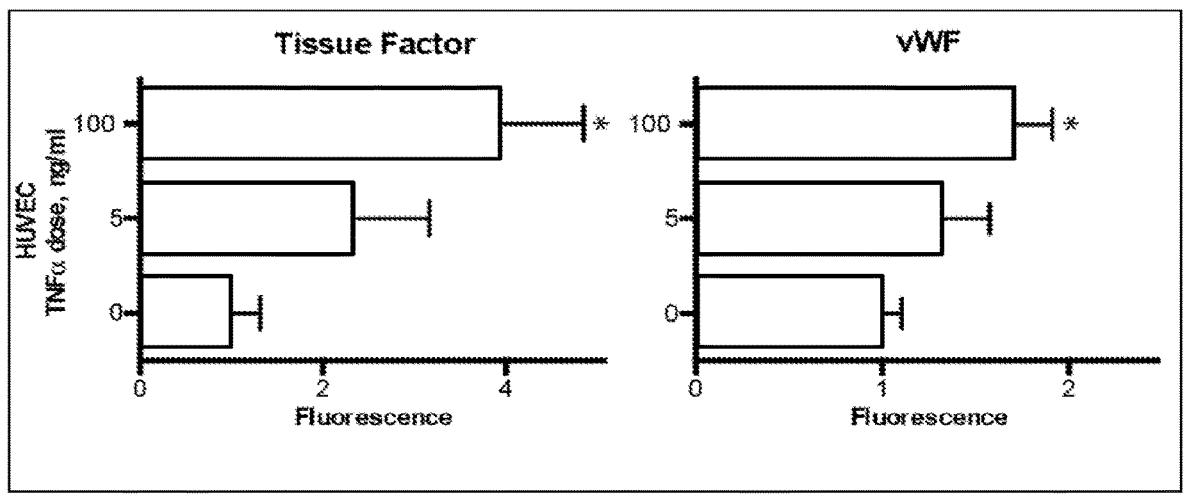
FIG. 72 is a set of bar graphs showing expression of tissue factor (TF) and von Willebrand factor (vWF), respectively, on TNF-α inflamed endothelium. HUVECs were cultured on PDMS-coated 24 well plates for 48 h and left untreated or stimulated with 5 or 100 ng/ml TNF-α. The effect of TNF-α on TF (left panel) and vWF (right panel) expression on the endothelial cell surface was estimated by measuring immunofluorescence intensity, normalized with respect to the untreated case. (*P<0.05, n=3)

To recapitulate physiological interactions between flowing platelets and the endothelial surface of living microvessels, HUVECs were cultured on all four collagen-coated walls of the rectangular channel. This led to the formation of rectangular channel lined by a continuous, confluent endothelial monolayer, as demonstrated by VE-Cadherin and F-actin staining (FIG. 71A). When the living endothelium was stimulated with one or more inflammatory cytokine, e.g., TNF-α, monolayer integrity was maintained, but ICAM-1 expression increased in a dose-dependent manner (FIG. 71B), which closely mimics endothelial activation observed during inflammation in vivo. An increase in the endothelial expression of prothrombogenic tissue factor (TF) and von Willebrand Factor (vWF) is also found in a dose dependent manner (FIG. 72).

Spatiotemporal Visualization of Platelet Function in Flowing Blood.

Figure 66A:
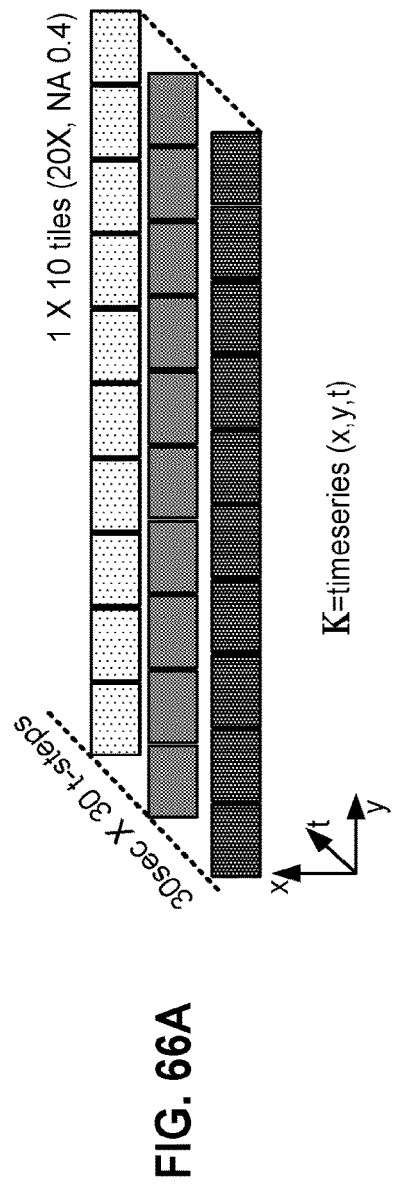
FIGS. 66A-66B depict the comparison of platelet aggregation on collagen versus living endothelium.

When the device is perfused with whole blood, thrombi that are rich in platelets and fibrin form on the surface (FIG. 65C). The spatiotemporal dynamics of fluorescent platelet activity during formation of these thrombi on the endothelial surface was analyzed by time-lapse imaging. As flow was stable for at least 15 min, all experiments were carried out within the first 15 minutes. In some embodiments, blood might begin to clot in the tubing connected to the chip at later times (leading to decreased perfusion rates). It was discovered that contrary to results obtained with surfaces coated with thrombogenic proteins, the reactive surface of a living activated endothelium is highly heterogeneous, as evidenced by detection of significant spatial and temporal variability in platelet adhesion, aggregation, translocation, and embolization (data not shown). To analyze these dynamic changes in platelet interactions with the surface of the endothelium, an automated imaging program was created that creates a 10-frame panorama, collectively covering a large (6 mm long×0.665 mm wide) region of the microchannel. Image analysis was limited to the 200 µm central region where shear rate gradients are minimal to avoid potential boundary layer effects. This resulted in an analytical volume of ~0.12 µL it after image cropping, which permits analysis of ~24,000 platelets (mean platelet count: 200,000 per µL whole blood) in a single composite view. The temporal resolution was fixed to 30 sec (limited by the speed of the image acquisition of the microscope), and imaging was automatically performed for 30 time steps over 15 minutes (FIG. 66A). Analysis was focused on the 2.5-12.5 min time points of the acquired time series, K(x,y,t), which covers the period of steady growth (accelerating phase) of native whole blood clotting.

Platelet Aggregate Morphology.

Figure 66B:
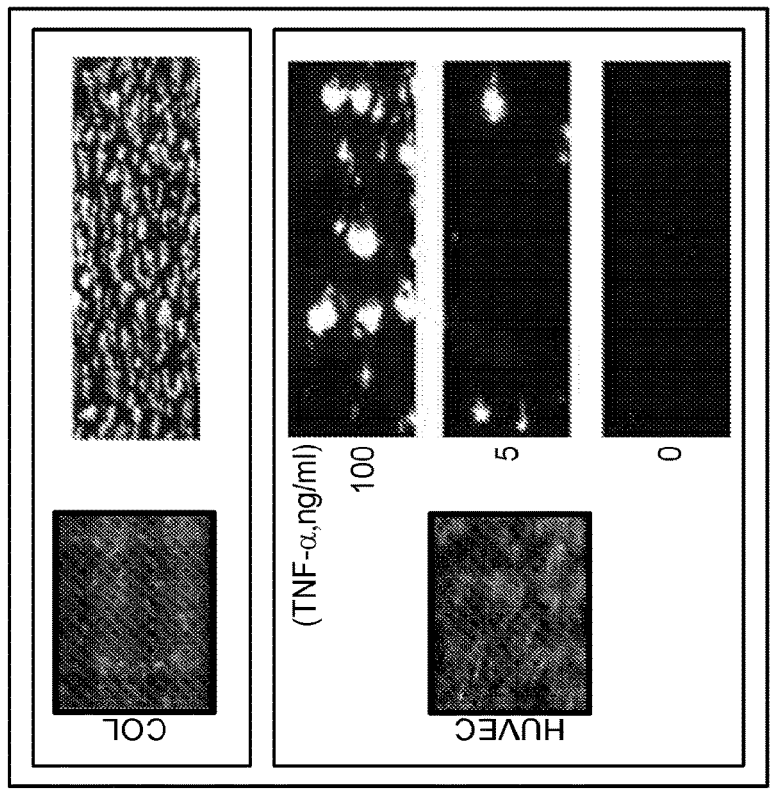

Perfusion of blood through the microchannels consistently resulted in formation of large and stable platelet aggregates when the channels were coated with type I collagen without endothelial cells (FIG. 66B), which is consistent with previous in vitro studies modeling hemostasis induced by vascular wall injury. In contrast, when the collagen-coated microchannel was covered with a continuous living endothelial monolayer, very little platelet interactions and aggregate formation were observed over the course of the 15 min experiment, much as what is observed in blood flowing in a healthy human blood vessel. However, when the endothelium was pre-treated with varying doses of TNF-α, platelet adhesion and aggregation again resulted, but the morphology of the platelet aggregates was clearly distinct from the aggregates that formed on the collagen surface (FIG. 66B). The typical size of aggregates on activated endothelium was visibly larger and they were more sparsely distributed. Interestingly, the size, shape and organization of the thrombi that formed on the activated endothelium in this in vitro model were reminiscent of what has been previously observed in vivo in animal models. Despite these distinct qualitative observations under different conditions, no quantitative parameters currently exist for the comparative analysis of platelet-endothelial interactions in platelet function assessment microdevice. In one aspect, described herein are methods to quantify platelet-endothelial dynamic interactions in an in vitro device, e.g., a platelet function assessment microdevice described herein.

Platelet Adhesion and Aggregation.

Figure 73A:
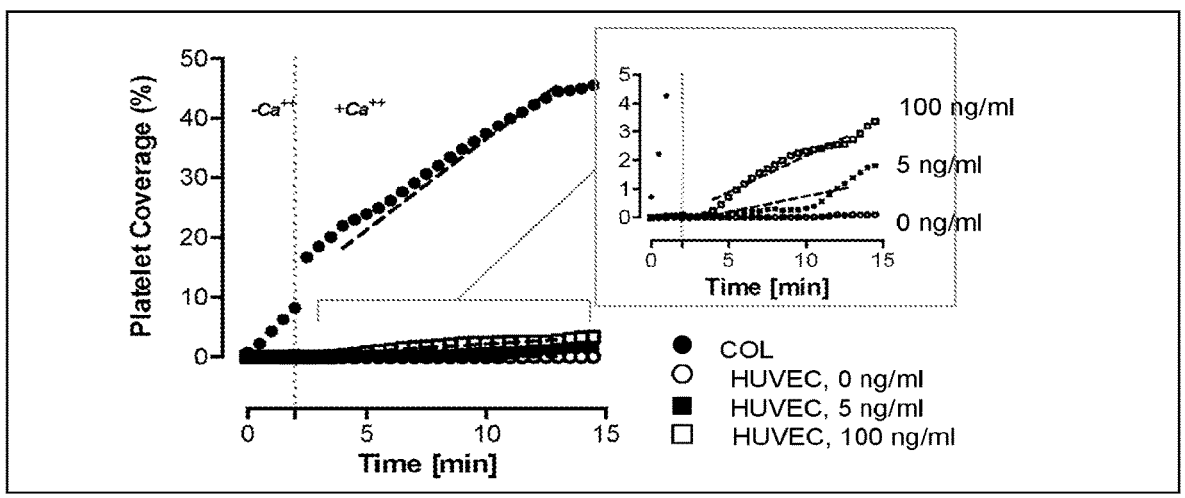
FIGS. 73A and 73B are data graphs showing area averaged platelet adhesion rate.
Figure 73B:
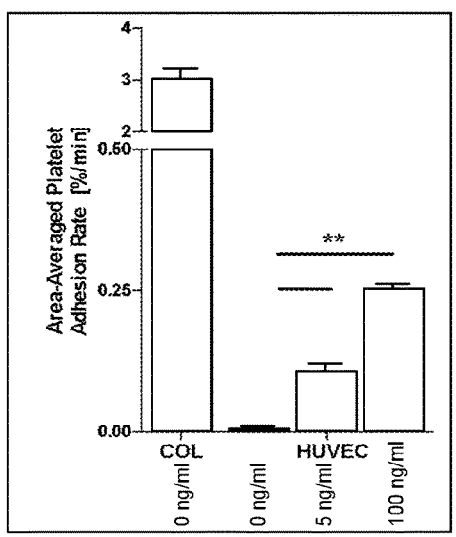

Platelet adhesion and aggregation events that mediate arterial thrombosis are mediated by glycoproteins and integrins that are expressed on the surfaces of platelets and endothelial cells. In most of the previous studies analyzing this process, the response was measured by quantifying the percentage of the endothelial surface that was covered with adherent platelets, with a spatial resolution of a few hundred microns. This analysis is typically performed by binary segmentation of the image after setting a threshold fluorescence intensity for each image acquired. The percentage area covered is then calculated as the ratio of the number of labeled pixels to the size of the binary image and plotted against time (FIGS. 73A-73B). There are two major limitations of this method. First, this analysis relies on variables that can alter platelet fluorescence (e.g., dye concentration, labeling efficiency, light intensity, diffraction, exposure time, etc.) that may vary from sample to sample, or experiment to experiment. Another significant problem is that the area averaging parameter does not provide any in-depth information regarding the heterogeneity of the platelet aggregates or the variation in spatiotemporal platelet dynamics (i.e., whether the individual platelet-rich thrombi are adhering, aggregating, translocating or embolizing).

Figure 67B:
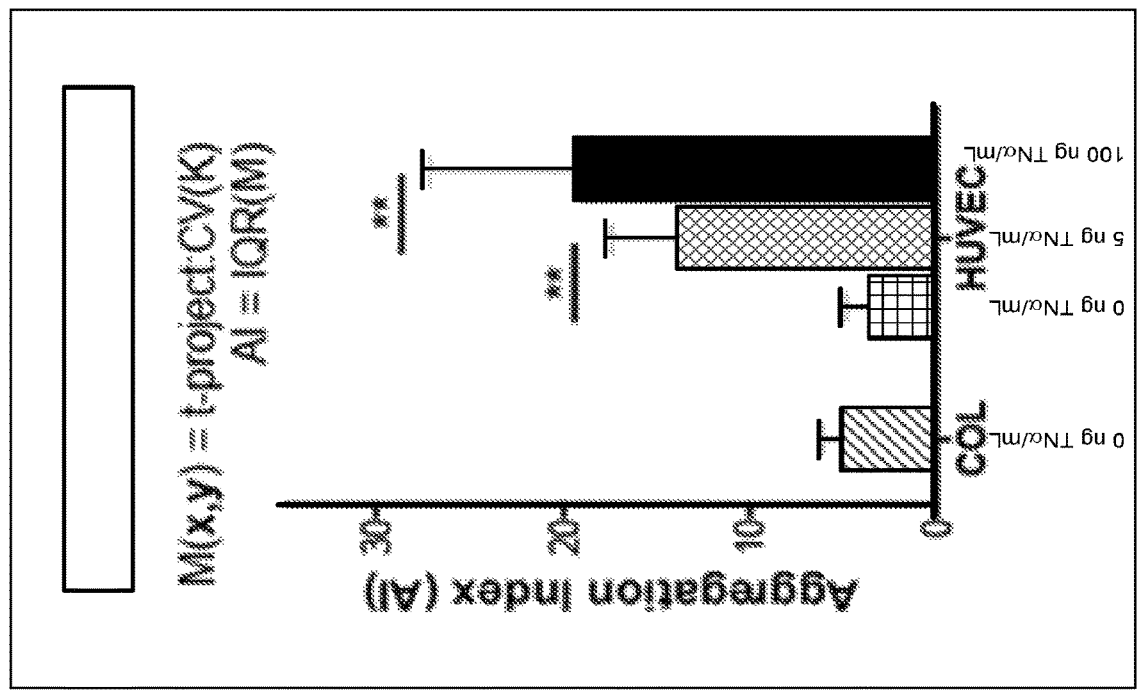
FIGS. 67A-67B depict the quantitative analysis of platelet adhesion and thrombus formation using an Aggregation Index (AI).
Figure 67A:
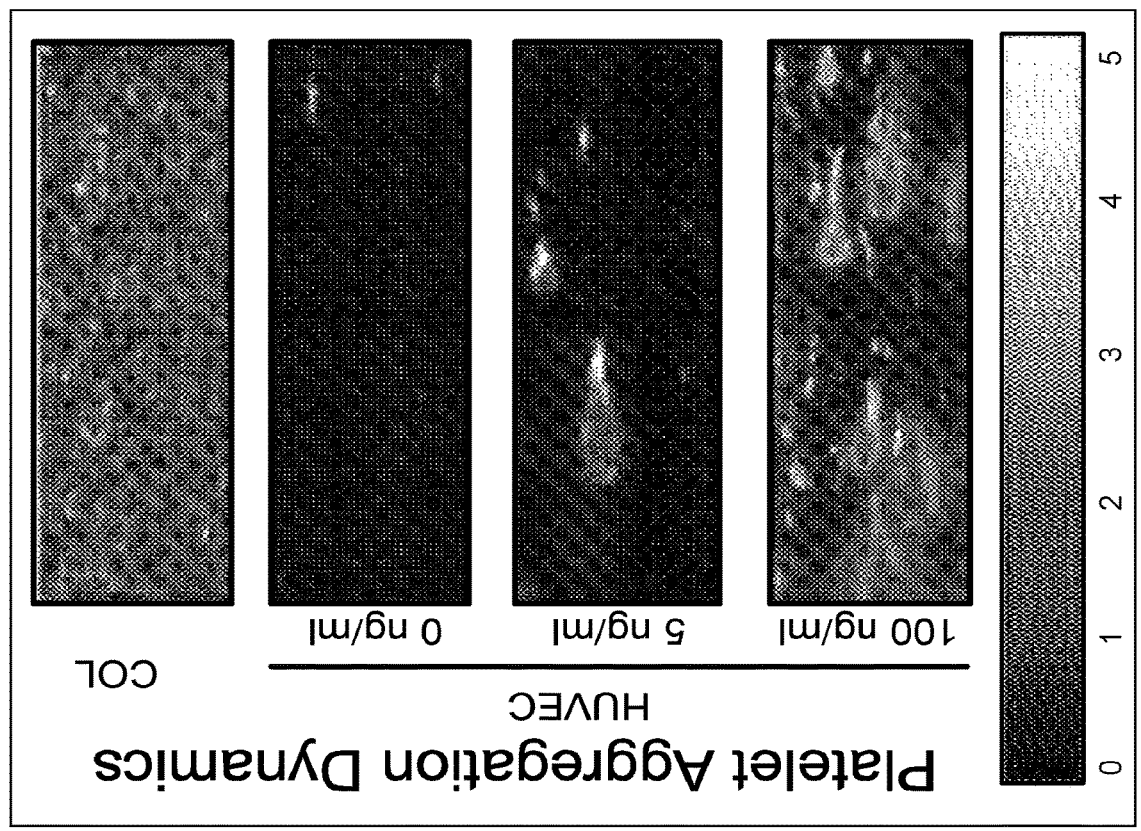
Figure 74:
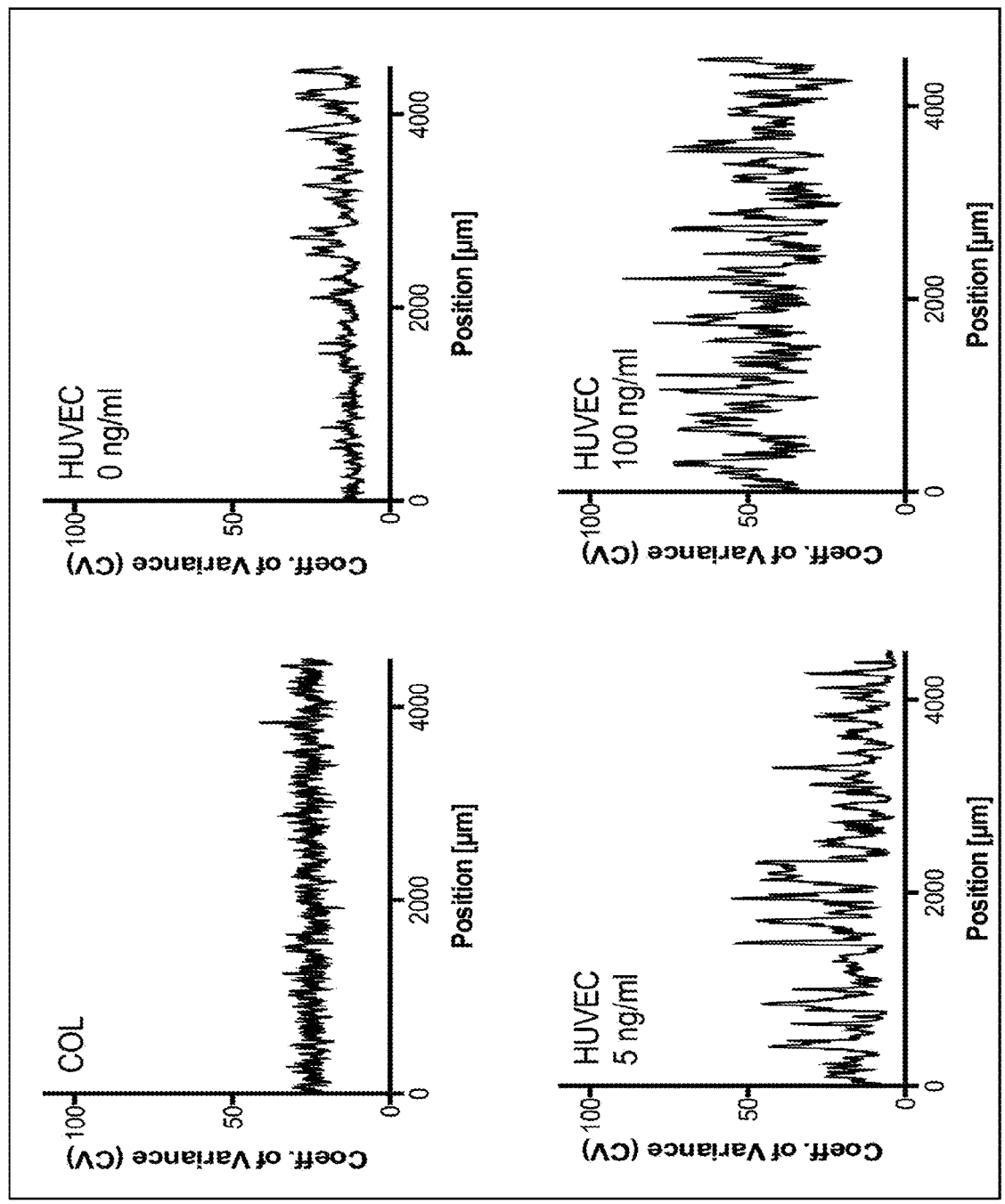
FIG. 74 is a set of data graphs showing platelet adhesion and aggregation dynamics. Graphical representation of the coefficient of variance (CV) image M(x,y). On a collagen (COL) and healthy endothelial (HUVEC 0 ng/ml) surface, the range of variance is narrow. However, the platelet patterns on TNF-α treated endothelium (HUVEC) are heterogeneous and fluctuate in a dose-dependent manner. The inter-quartile range (IQR) of the signal is termed platelet aggregation index (AI).

To analyze the behavior of platelet aggregates and thrombus forming on collagen or activated endothelium directly (i.e., independently of fluorescence intensity), the coefficient of variance (CV)—the ratio of standard deviation to the mean—of the fluorescent signal over time was calculated, and a t-projection of the time series (K) was performed, resulting in a spatial map, M(x,y), of platelet adhesion and aggregation dynamics (FIG. 67A). The resulting spatial image can then be reprocessed using a color map and analyzed using an intensity palette look-up table to contrast highly active versus dormant areas (FIG. 67A). This image intensity transformation enabled visualization of dynamic behavior of individual platelet aggregates, in addition to conveying the overall pattern of platelet aggregation. For example, a uniform platelet adhesion pattern with a narrow range of temporal variance on a cell free collagen surface was observed (FIG. 67A). When blood was flowed over a healthy endothelium, platelets show very limited reactivity with the apical surface and therefore, the color spectrum was almost entirely black; however, the platelet patterns on endothelium treated TNF-α were heterogeneous and fluctuated in a dose-dependent manner (FIG. 67A and FIG. 74).

An Aggregation Index (AI) was developed to quantitatively capture spatial variance in platelet-rich thrombus formation on collagen and endothelium. AI corresponds to the statistical inter-quartile range (IQR) (difference between the third and first quartile of CV values) for each image M(x,y). This analysis revealed that platelet behavior on the collagen surface was highly reactive, but uniform, and there was negligible adhesion or reactivity on surface of the healthy endothelium; thus both had a low AI (FIG. 67B). Further, it was found that the AI of platelet-rich thrombi on inflamed endothelium varied depending on the dose of TNF-α, and hence, the state of inflammation (FIG. 67B).

Figure 68B:
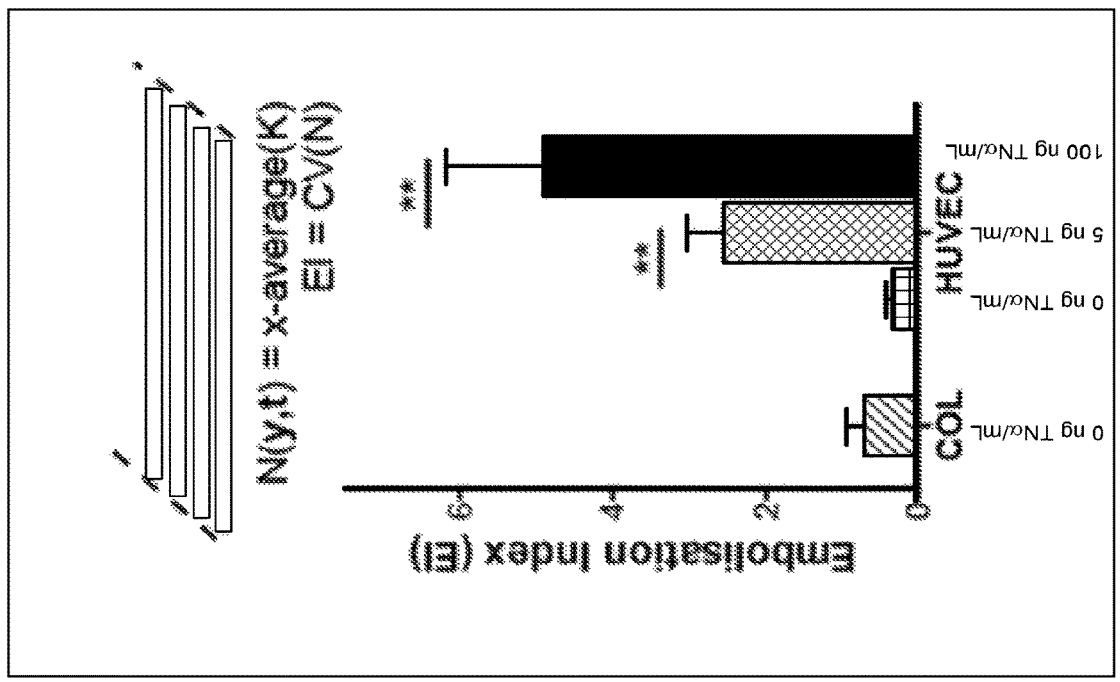
FIGS. 68A-68B depict the quantitative analysis of translocation and embolization of platelet-rich thrombi using an Embolization Index (EI).
Figure 68A:
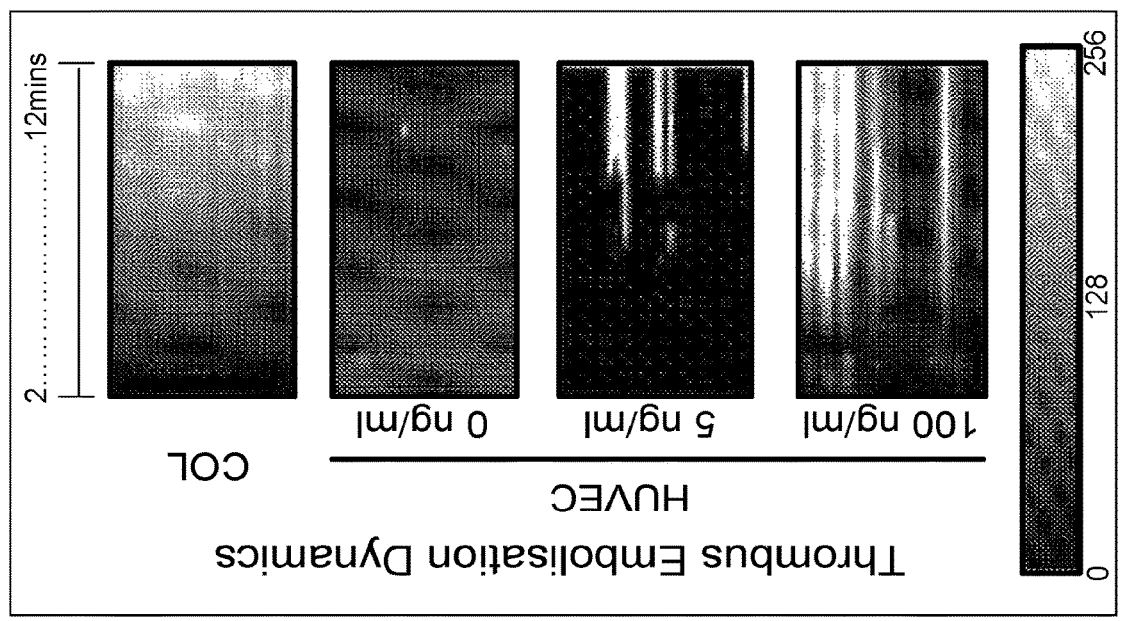

Thrombus Translocation and Embolization. It was observed that in addition to platelets adhering and aggregating into larger platelet-rich thrombi, the thrombi themselves would sometimes also translocate or embolize over time. This embolization of platelet-rich thrombi is important from a clinical perspective, as embolisms sometimes may lead to fatal complications. Time-averaged parameters analyzed in in vitro assays, such as area fraction and AI, do not adequately capture this process. Thus, to analyze temporal platelet and thrombotic processes, such as platelet-rich thrombi translocation and embolization, parametrically using this assay, the technique of kymography was applied. In this method, the time series K(x,y,t) is averaged across the x-axis and transformed to create a space-time map N(y,t), such that the horizontal spatial axis is time (t) and the vertical axis is platelet fluorescence along the length of channel (y) (FIG. 68A). On a collagen surface, platelet adhesion on the substrate increased at a steady rate over time and there were no deviations or abrupt changes in fluorescence (FIG. 68A). Similar analysis of an unstimulated (control) endothelial surface resulted in a uniform and dark kymograph (FIG. 68A). However, the kymographs on TNF-α treated endothelium exhibited great variation in the fluorescent signal over time and space representing translocation or embolization of platelet-rich thrombi, and this behavior altered in a dose-dependent manner.

A fluorescence-independent quantitative parameter was defined to capture this variation in pattern, or embolization index (EI), which corresponds to the statistical coefficient of variance (CV) of the image N(x,y). Similar to the results obtained with the AI, surfaces coated with collagen or quiescent endothelium exhibited a low EI, as the platelet behavior was either uniformly highly reactive or negligible, respectively (FIG. 68B). This analysis also showed that the EI of platelets on inflamed endothelium increased with increasing doses of one or more inflammatory cytokine, e.g., TNF-α, and thus this parameter was able to capture the processes of translocation and embolization in this model of an inflamed vessel.

In one aspect, described herein is a new microdevice with integrated analytical methods that represent a novel in vitro tool for quantitatively assessing the dynamic functions of platelet and thrombus interactions with living endothelium under flow. This assay can be utilized in biomedical research or clinical settings because of its ease-of-use, small sample size, automated analysis and high information content. The novel analytical methods described herein have several advantages relative to the existing microfluidic thrombosis and platelet analysis models. First, endothelial cells are an integrated component of the assay, which allows one to study the interplay of endothelial dysfunction and blood-derived factors in causing thrombosis or bleeding. This advantage is clearly demonstrated by the finding presented herein that TNF-α treatment produces dose-dependent effects on several aspects of platelet dynamics when endothelium is present. The other main advantage of the methods described herein is that it simultaneously permits stochastic analysis of relevant parameters of platelet dynamics at a large scale and by enabling high resolution visualization of cellular responses at the single platelet level. Moreover, the ability to quantify and compare various parameters relating to platelet function (adhesion, aggregation, translocation and embolization of platelet-rich thrombi), while also carrying out morphological observations, enabled clear comparison between the effects of the different biomimetic surfaces. The working principle of this microfluidic assay and/or methods described herein is also flexible, in that the methods described herein can be integrated with a variety of other biomedical assays and in vitro disease models. For example, the methods or assays described herein can be easily combined with fibrin analysis, by introducing fluorescent fibrinogen along with labeled platelets (FIG. 65C). In some embodiments, the methods and/or devices described herein can also be integrated with organ-on-a-chip technology to study the effects of parenchymal tissue damage, organ inflammation, and vascular (or perivascular) tissue dysfunction on platelet dynamics and thrombosis in vitro in a comprehensive fashion.

In addition, a standardized device can permit this assay to be used to evaluate patient samples in clinical diagnostic settings. This ability to assess the full spectrum of platelet function enables a more informed risk assessment for thrombosis in at-risk disease populations. For example, the fluorescence microscopic analysis can be replaced with other imaging modalities, such as wide-field holography or impedance spectroscopy.

K. Example 6. Whole Blood Platelet Analysis on a Chemically Preserved Bioactive Endothelium Inside a Microfluidic Device Thrombosis depends on blood interacting with an inflamed vascular endothelium under flow, but it is impractical to incorporate living endothelial cells in platelet function diagnostic devices used in laboratories or at the bedside. In one aspect, described herein is a microfluidic device lined by a non-living, fixed, stimulated endothelium that supports formation of platelet-rich thrombi as blood flows through its channels. The clinical value of chemopreserved endothelialized devices is demonstrated herein, e.g., by showing that they can be used to monitor antiplatelet therapy in cardiac patients.

Mutual signaling between an inflamed endothelium and activated platelets is commonly recognized as the cause of disturbances in hemostasis, platelet aggregation and resulting thrombotic disorders in various diseases, yet no reliable diagnostic assays exist that can measure the effects of cross-talk between platelets and an inflamed vessel wall. Microfluidic devices that incorporate microchannels with a physiological relevant size that are lined by living inflamed endothelium exposed to flowing blood can be used to study thrombosis in vitro. However, it is not practical to incorporate living endothelial cells in clinical diagnostic devices given problems associated with culture stability, robustness, standardization, storage, and shipping.

Figure 69A:
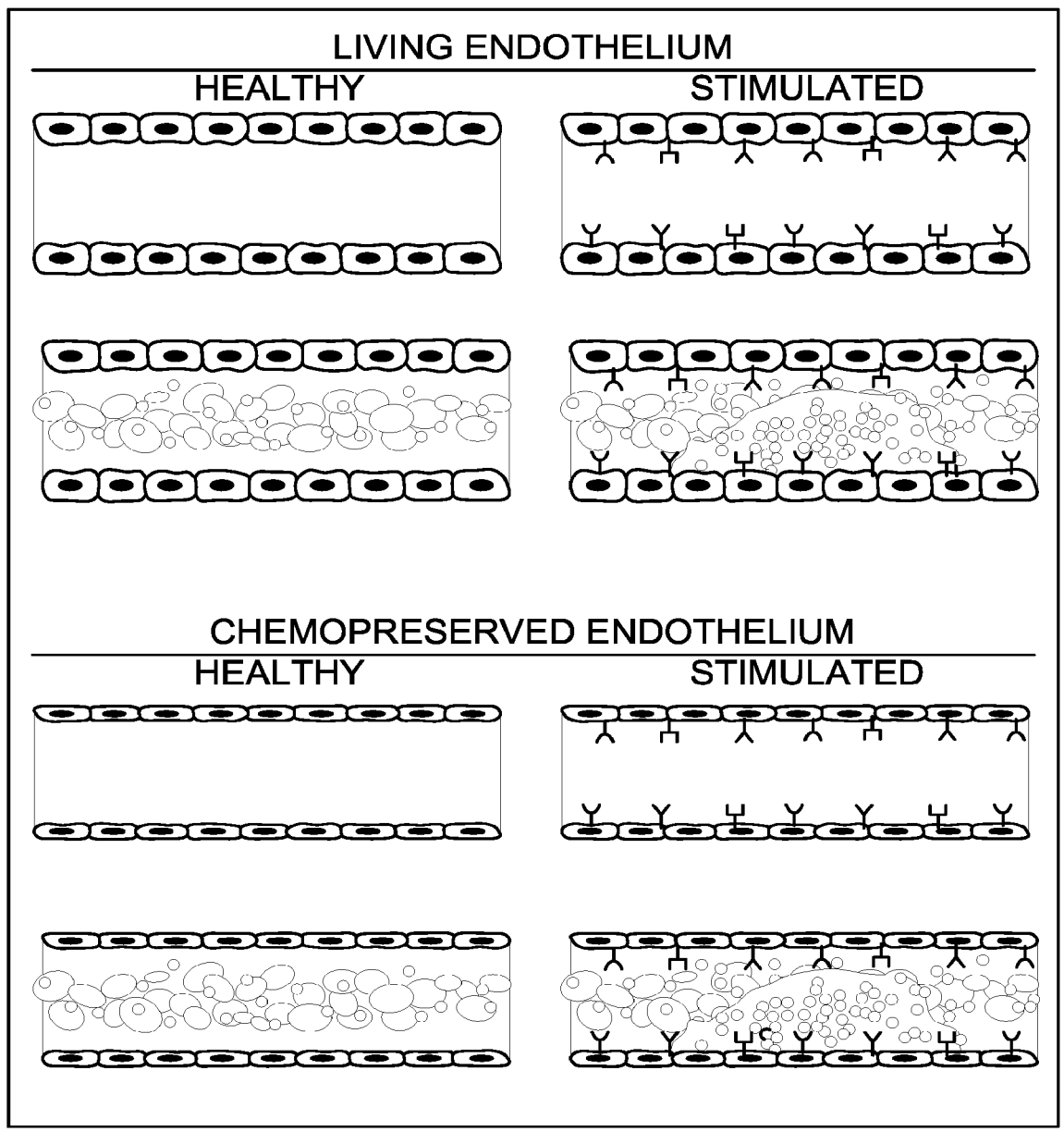
FIGS. 69A-69E depict whole blood platelet analysis on chemically preserved endothelium in a microchannel according to one embodiment described herein.
Figure 69B:
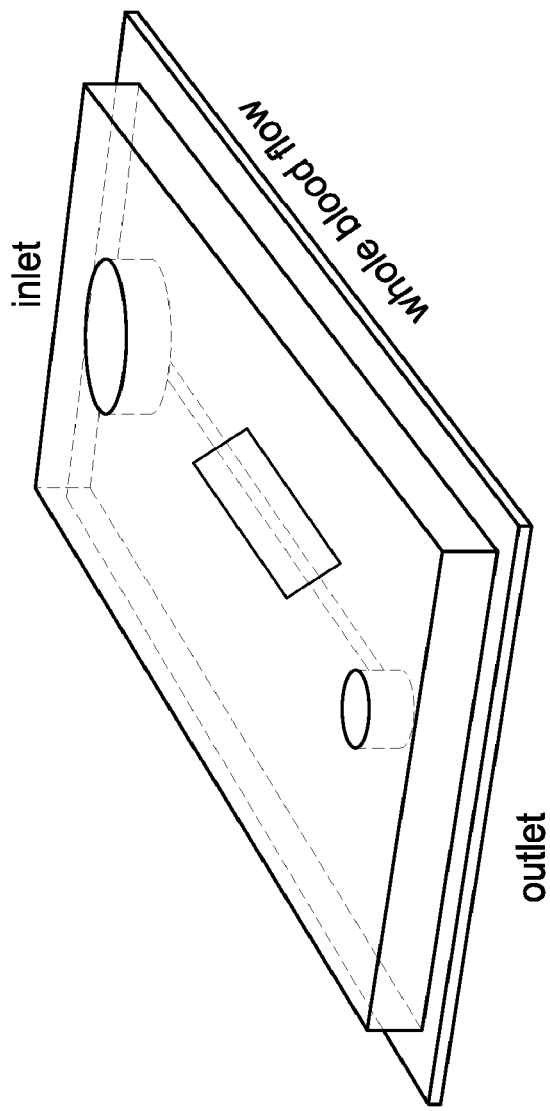
Figure 69C:
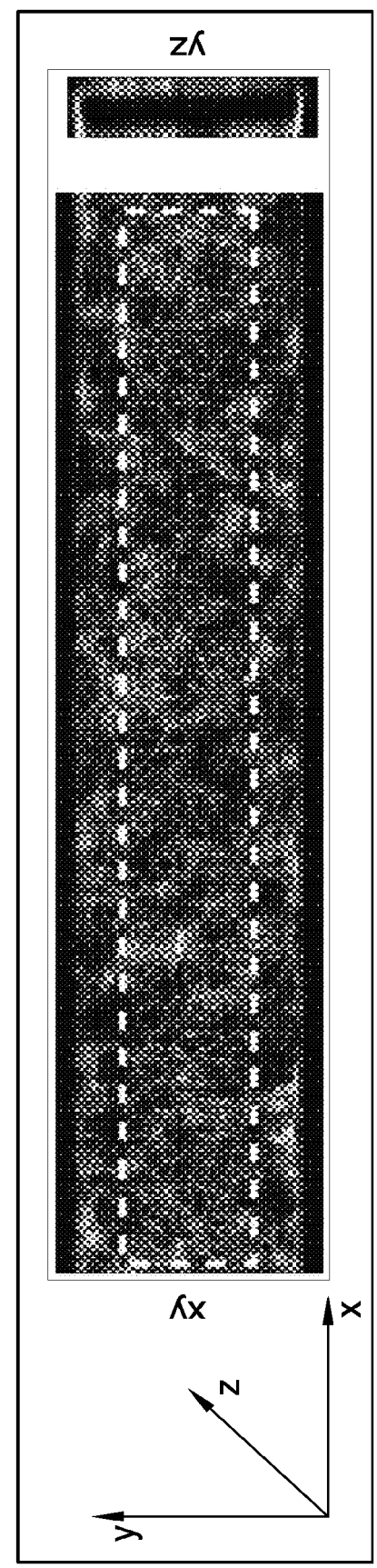
Figure 75:
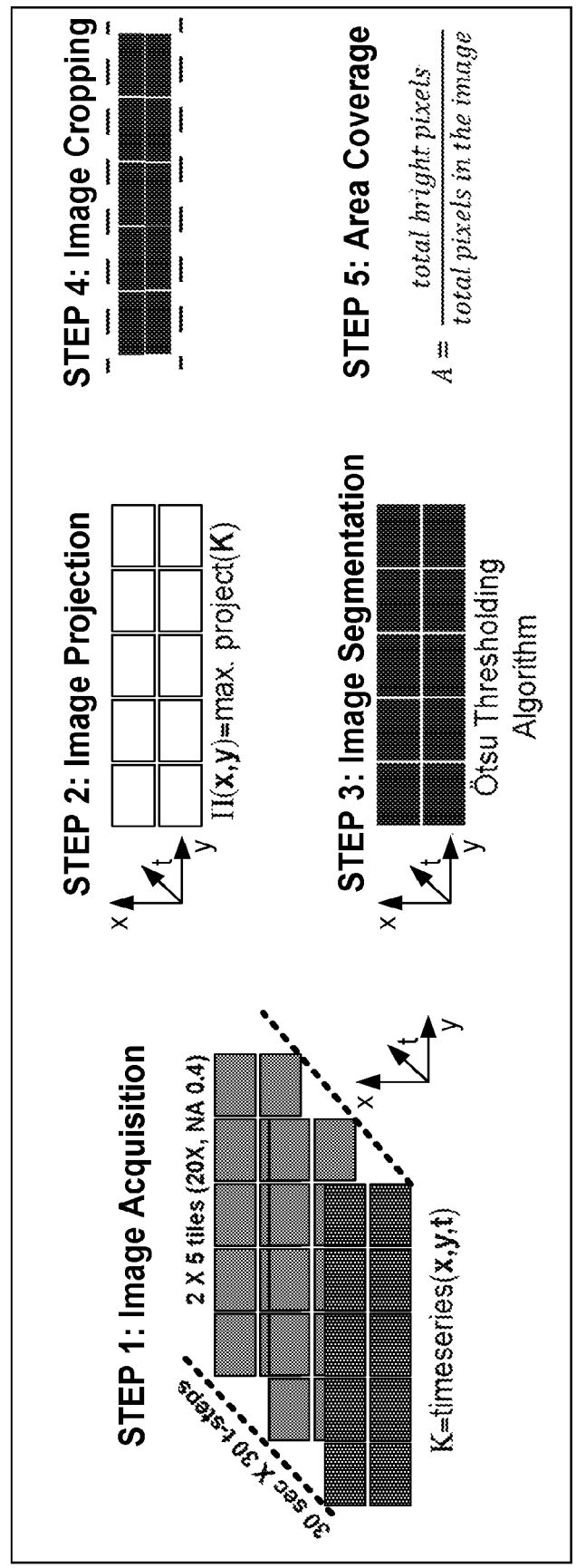
FIG. 75 shows an exemplary image acquisition and analysis protocol for platelet coverage. Platelets were visualized using time-lapse fluorescence imaging (LD Plan Neofluar 20×, NA 0.4; Zeiss Axio Observer; Hamamatsu ORCA C11440 CMOS digital camera) using an exposure time of 200 ms. Images were tiled to create a composite panoramic view (18,600 pixels long and 2,050 pixels wide; 1 pixel=0.325 μm). In step 1, a timeseries (K) of a 10-frame panorama (6 mm long×0.665 mm wide region of the microchannel), at a lapse of every 30 seconds was recorded. Images were archived as OME-TIFF format files, and image analysis was performed using Zeiss Zen 2012 imaging software and MATLAB 2014 routines. The resulting image stack was maximum intensity projected along time (step 2), thresholded, segmented (step 3) and cropped to the central 200 μm of the channel width (step 4) for analysis. Finally, platelet coverage was computed from the binary image as the ratio of bright pixels (intensity value=1) to the total number of pixels in the image (step 5).

To this end, the inventors recapitulated platelet-endothelial crosstalk by culturing human umbilical vein endothelial cells (HUVECs) on all four walls of a type I collagen coated rectangular channel (400×100 µm), which led to formation of a rectangular tube lined by a continuous, confluent endothelial monolayer (FIGS. 69A-69B), as described in Example 5. The monolayers were either left untreated or were treated for 18 hours with varying doses of the pro-inflammatory cytokine tumor necrosis factor-alpha (TNF-α). After the endothelial monolayer was formed and inflammatory treatment was complete, these endothelium-lined devices were chemically preserved, for example, by fixing them with 4% formaldehyde diluted in phosphate buffered saline (PBS) for 15 minutes, at room temperature (FIGS. 69A-69B). After fixation, the devices were rinsed three times with PBS and then they were stored at 4° C. for 24-36 hours before use. Citrated human whole blood with fluorescently tagged platelets was perfused through these fixed endothelium-lined microchannels at a shear rate of 750 sec$^{-1}$, using less than 500 µl of blood per assay (FIG. 69C). After 2 minutes, the blood was supplemented with calcium (CaCl$_2$) and magnesium (MgCl$_2$) to initiate physiological blood clotting, which was analyzed for 2.5-12.5 min. Platelet accumulation was measured as the percentage area occupied by the platelets in the central 200 µm of the channel width (FIG. 75).

Figure 69D:
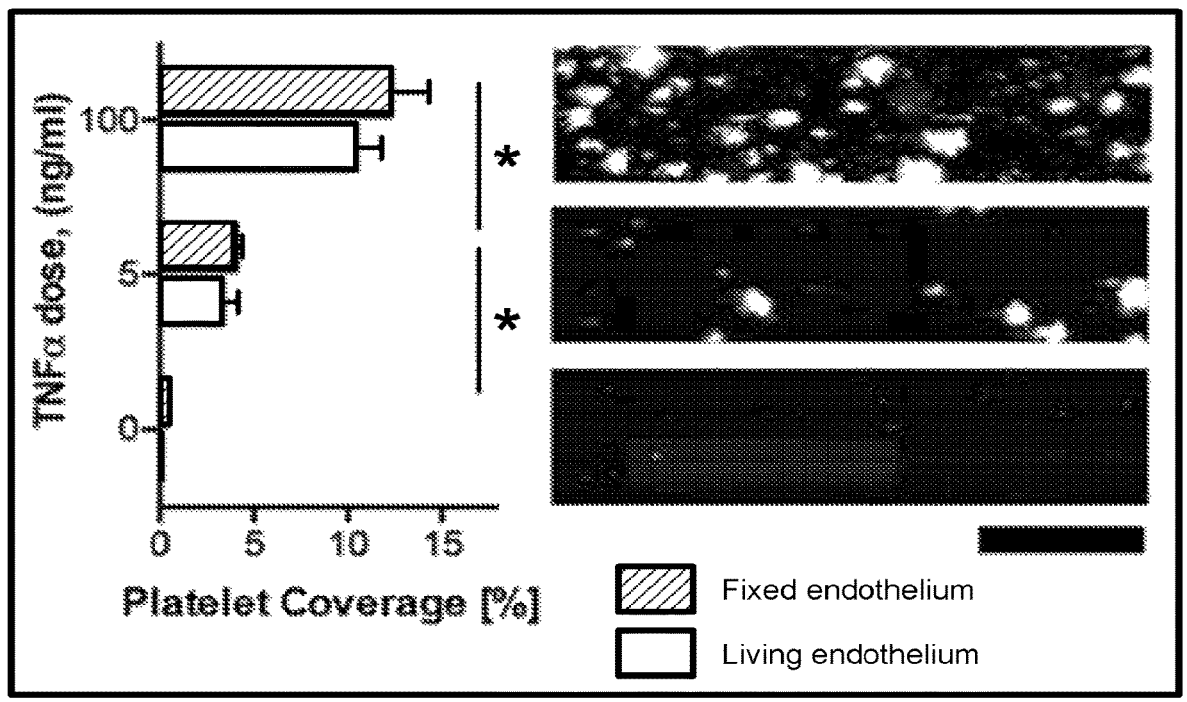
Figure 69E:
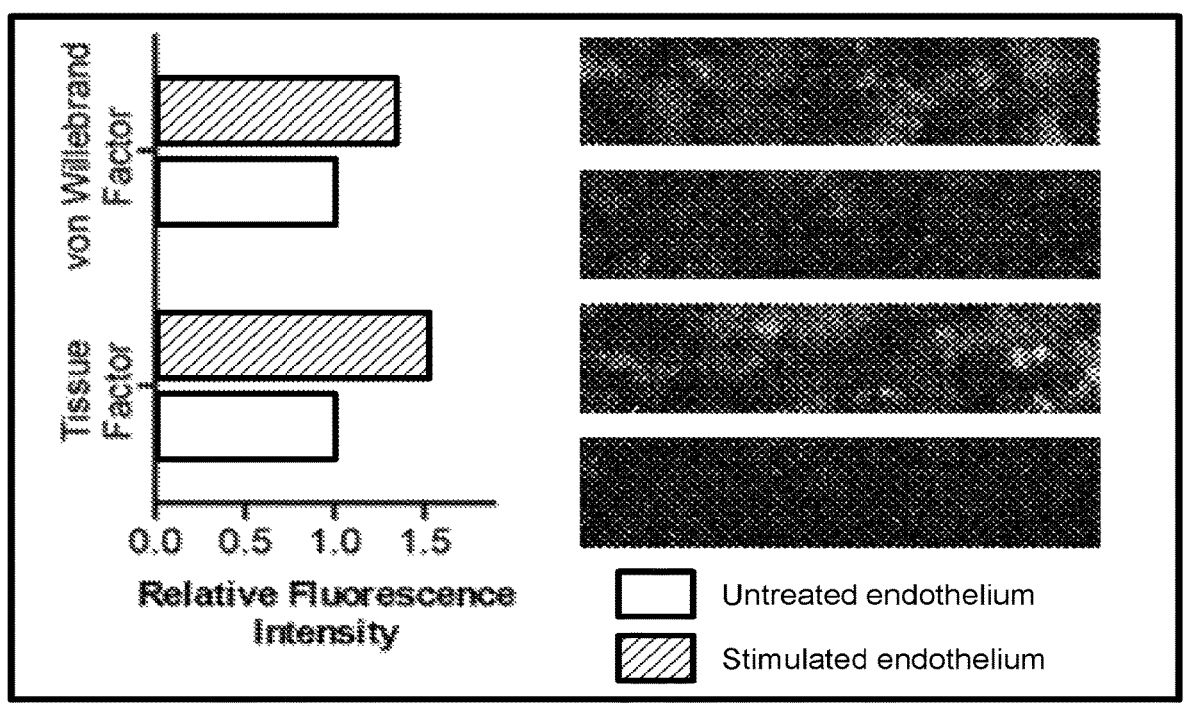

Adding increasing doses of one or more inflammatory cytokine, e.g., TNF-α, to the endothelium prior to fixation resulted in a dose-dependent increase in surface coverage of platelet-rich thrombi (FIG. 69D). The morphology of these thrombi was distinctly different from the platelet aggregates that formed on collagen-coated device, which mimicked platelet aggregation and adhesion that occurs on the surface of the living endothelium during inflammation as in vivo. In contrast, there was virtually no induction of platelet-rich thrombi formation on fixed quiescent endothelium (FIG. 69D). In addition, no significant difference in platelet accumulation was observed between a living and chemopreserved endothelium, at all the tested doses of TNF-α, thus showing that the synthesized cellular surface retains key pro-thrombotic characteristics after fixation (FIG. 69D, n=4). It was also shown that the platelet-rich thrombi that formed on the chemopreserved endothelial surface were morphologically larger than the aggregates that formed on a collagen surface, but similar to a living endothelium (FIG. 76). Moreover, thrombi on this bioactive surface were rich in fibrin, which also showed that their formation was dependent on an active coagulation cascade (FIG. 76). This activity was further substantiated when it was found that the endothelium treated with a low dose (5 ng/ml) TNF-α expressed higher levels of prothrombotic tissue factor (TF) and von Willebrand Factor (vWF) than untreated, after fixation (FIG. 69E).

Figure 70A:
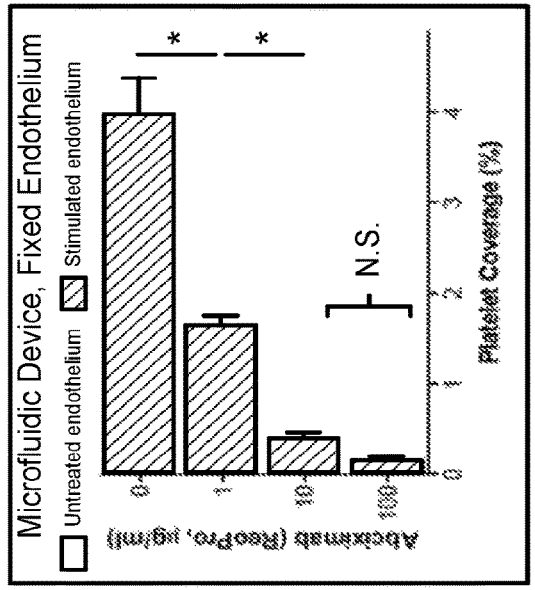
FIGS. 70A-70F are bar graphs depicting analysis of the chemopreserved endothelium covered microchip to monitor antiplatelet therapy.
Figure 70B:
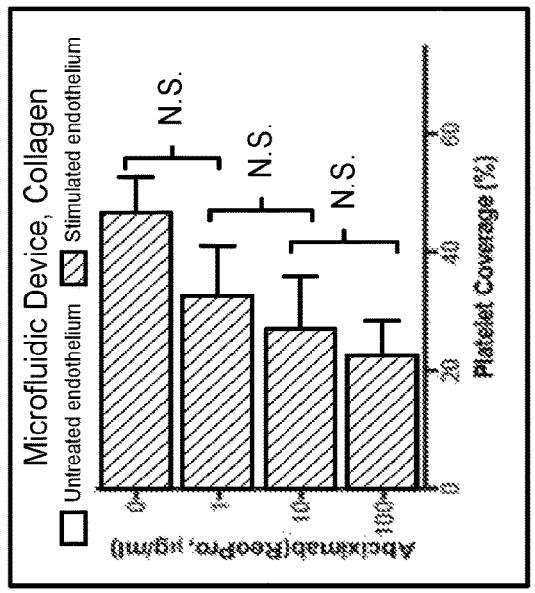
Figure 70C:
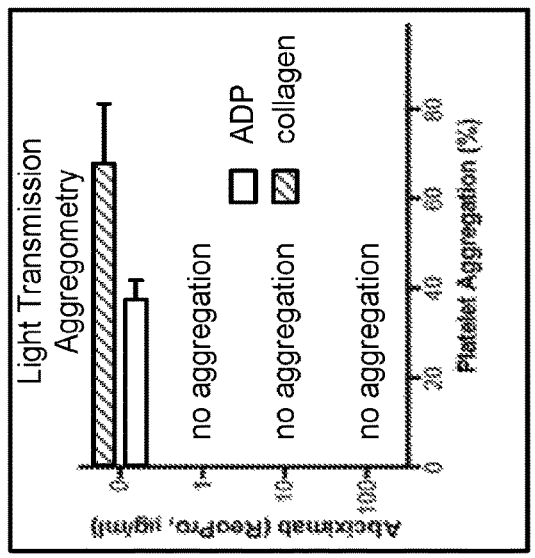

This data led to the investigation of whether an assay, containing a fixed bioactive endothelial substrate, can be used to detect anti-platelet drug dose effects, and to compare to a similar sized collagen-coated microchannel using the standard LTA (light transmission aggregometry). Thus, a concentration of 5 ng/ml of TNF-α was selected for causing endothelial activation, which is in the pathophysiologically relevant range. First, when an antiplatelet GP IIb/IIIa antagonist drug, abciximab (ReoPro), was added in the range 0-100 µg/ml (clinical range ~1-10 µg/ml) to whole blood and platelet adhesion was measured, a significant dose-dependent platelet inhibition was found between untreated and 1 µg/ml drug and between 1 µg/ml and 10 µg/ml drug (n=3, FIG. 70A). The difference between 10 µg/ml and 100 µg/ml was insignificant, because at these high doses, platelet inhibition was maximized. Surprisingly, the dose-dependent effect of abciximab on surface coverage in a collagen-coated flow chamber had poor sensitivity whereas abciximab-treated platelets demonstrated no platelet aggregability by LTA in response to either ADP (adenosine diphosphate) or collagen agonists (FIGS. 70B-70C). This validated that the platelet aggregation measurement on the chemopreserved endothelium provided a dynamic response across a range of abciximab concentrations indicating that a chemopreserved endothelium can be used to monitor anti-platelet regimens in patients. This also showed that the surface conserved platelet interactions via the GPIIb/IIIa pathway, involved in many thrombotic and vascular processes.

Whole blood of patients who underwent angiography at a cardiac catheterization lab in the clinic are regular users of antiplatelet drugs, e.g., aspirin alone or both aspirin and clopidogrel (Table 1).

TABLE 1

Clinical characteristics of subjects tested for platelet aggregation

| Subject | Aspirin | Clopidogrel |
|---------|---------|-------------|
| 7   | + | 0 |
| 8   | + | 0 |
| 9   | + | + |
| 16  | + | 0 |
| 18  | + | + |
| 22  | + | 0 |
| 59  | + | + |
| 61  | + | 0 |
| 63  | + | + |
| 65  | + | + |
| 84  | 0 | 0 |
| 85  | + | 0 |
| 106 | + | 0 |
| 109 | + | 0 |
| 113 | 0 | 0 |
| 117 | + | 0 |

Figure 70D:
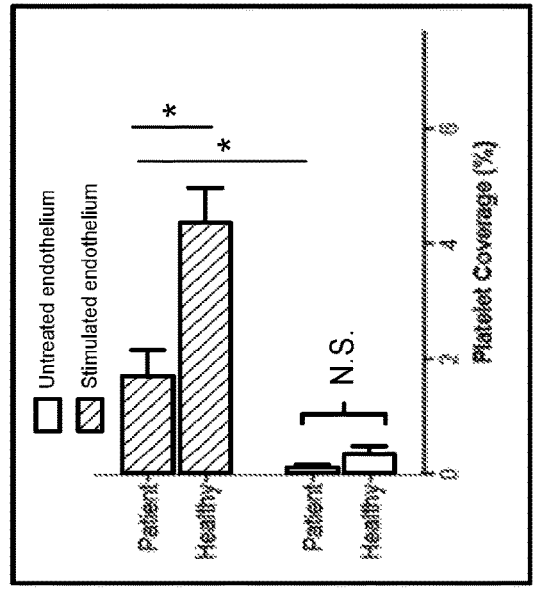
Figure 70E:
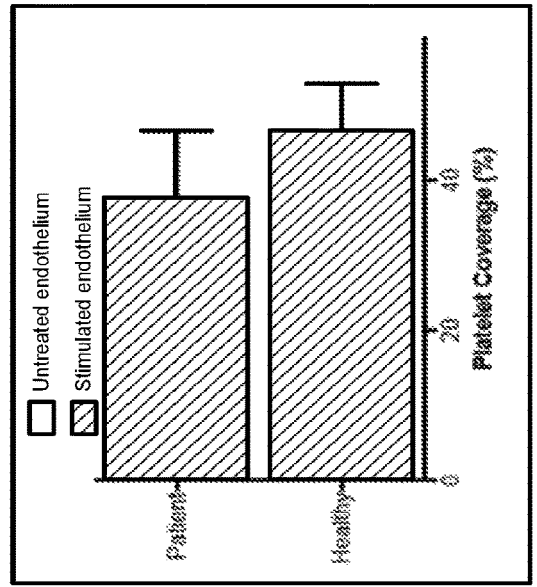
Figure 70F:
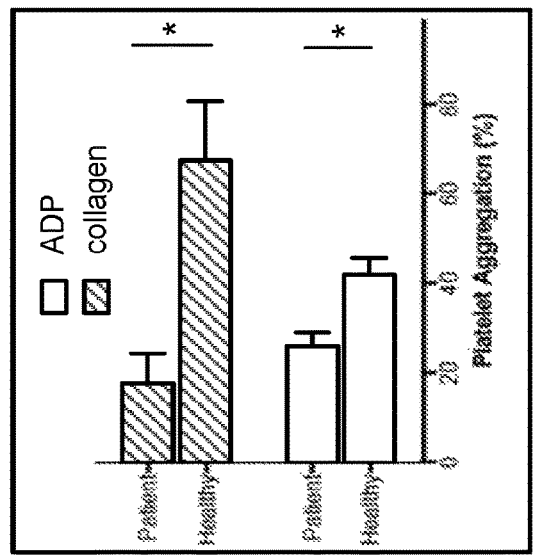

Thus, it was next sought to perfuse whold blood of these patients and to determine if the assays with a chemopreserved endothelium can be used to determine effects of antiplatelet drugs. In a subject population that was tested (n=11), it was found that compared to healthy donors, patients showed a significant reduction in platelet aggregation in the device described herein, consistent also with LTA (FIGS. 70D-70F). Also, both healthy controls and patients showed complete platelet inhibition over an untreated endothelium but when the endothelium was stimulated, both groups showed some signs of platelet rich thrombus formation, showing that subjects may have a higher tendency to thrombosis when vascular inflammation is present (FIG. 70D). These data also indicate that patients on antiplatelet agents who show platelet adhesion similar to healthy donors can be advised for monitoring as they may be at risk for a thrombotic event. These results could not be reproduced with the same sensitivity on a collagen, unendothelized coated flow chamber (FIG. 70E), demonstrating that the assay described herein is more reliable for assessing platelet reactivity in a clinical setting.

In vitro humanized disease models of thrombosis offer opportunities to significantly improve diagnostics and predict patient outcome, where blood-endothelial interactions are involved. In one aspect, described herein is a microfluidic device that contains a layer of chemically preserved endothelial cells that are either quiescent or pre-stimulated with TNF-α prior to fixation. The chemically preserved endothelium retains its respective passive or pro-thrombotic properties as if it were alive (FIGS. 69A-69E). It is demonstrated herein that these devices can be used to evaluate platelet aggregation and inhibition with drugs. This technology can enhance platelet function analysis at bench or bedside.

L. Exemplary Materials And Methods

Microfluidic Device Design and Fabrication.

Microfluidic device consisted of a microchannel, 400 µm wide, 100 µm high and 2 cm long. It was designed using AutoCAD™ software, master templates fabricated on Si (100) wafers (University Wafer Corp.) in combination with soft lithography using polydimethysiloxane (PDMS). Duffy et al. "Rapid prototyping of microfluidic systems in poly (dimethylsiloxane). *Anal. Chem.* 70, 4974-4984 (1998). Sylgard184™ PDMS prepolymer (Dow Corning) was cast on the silanized master that had the positive relief of the channel features formed by SU8 2075 photoresist (Micro-Chem Corp). The PDMS was then cured at 60° C. in a convection oven for 120 minutes, peeled off the master, and bonded to a PDMS coated glass slide after treating both with oxygen plasma for 20 seconds.

Microfluidic Device Pre-Treatment and Coating.

The microfluidic devices were pre-treated and coated with collagen before cell seeding. Devices were exposed to oxygen plasma for 30 seconds, at a power of 50 Watts, using a PE100™ plasma sterilizer (Plasma Etch, Inc. NV, USA) and then treated with 1% (3-aminopropyl)-trimethoxysilane (Sigma) in phosphate-buffered saline, PBS, for 10 minutes. After rinsing with 70% ethanol and 100% ethanol, the devices were baked at 80° C. for 2 hours. A solution of 100 µg/ml type I collagen from rat tail (Corning) in PBS was then introduced in the channels. The devices were left overnight at 37° C. and 5% $CO_2$, after which they were rinsed with Endothelial Growth Medium-2, EGM-2 (Lonza).

Cell Culture and Chemical Preservation.

Human umbilical vein endothelial cells, HUVEC, (mixed donor, Lonza) were kept in culture with EGM-2 and were trypsinized when confluent. After centrifugation at 250 g, HUVEC were suspended at a 12.5 million cells/ml in EGM-2. The suspension was introduced into the pre-treated and coated microchannels, after which the devices were incubated upside down for 20 minutes. A fresh HUVEC suspension was then introduced in the channels, after which the devices were covered with EGM-2 and left at 37° C., 5% $CO_2$ for 8 hours to promote cell attachment and spreading on all surfaces of the channel. After incubation, the channels were rinsed with EGM-2, sometimes containing a freshly prepared solution of tumor necrosis factor-alpha TNF-α (recombinant from *E. coli*, Sigma). After incubating for 18 to 20 hours at 37° C., 5% $CO_2$, a 4% formaldehyde solution (Sigma) was flushed through the channels and the devices were incubated for 15 minutes at room temperature. Finally, the devices were rinsed twice with EGM-2 and then placed at 4° C. The devices were used within 24-36 hours after placing them at 4° C.

Fluorescent Labeling of Platelets.

Platelets labeled with human CD41-PE antibody (10 µl/ml, Invitrogen) were directly added to the blood and incubated at room temperature for 10 min. The citrated blood was recalcified 2 minutes after blood perfusion by adding 100 µl/ml of a solution containing 100 mM calcium chloride and 75 mM magnesium chloride to the blood.

Light Transmission Aggregometry (LTA).

Blood from healthy donors was treated ex vivo with abciximab or used untreated. These samples as well as clinical blood samples from subjects were centrifuged at 290 g for 10 min (no brake applied) to collect platelet rich plasma (PRP). To obtain a reference solution for each sample, PRP was centrifuged at high speed to pellet platelets (1,000 g, 10 min) and collect platelet poor plasma (PPP). $CaCl_2$ was added to each sample at a final concentration of 1 mM to recalcify plasma before each run. Cifuni et al. "CalDAG-GEFI and protein kinase C represent alternative pathways leading to activation of integrin alphaIIbeta3 in platelets." *Blood* 112, 1696-1703 (2008). LTA has then been performed at 37° C. under magnetic stirring using a Chrono-Log Corporation instrument. Both platelet agonists, ADP (adenosine diphosphate) and collagen, were purchased from Chrono-Log Corporation and used as suggested by the manufacturer, in the concentrations of 10 µM and 2 µg/ml, respectively.

Blood Perfusion.

500 µl of whole blood was pipetted into a fluid reservoir fitted to one end of the microchannel on one side of the microfluidic device. A piece of medical grade tubing (30.5 mm long, 1.58 mm inner diameter; Tygon S-50-HL, Saint Gobain Plastics) was fitted to the outlet port of the device via a barbed luer lock connector (Harvard Apparatus). The other end of the tube was connected to a 3 ml syringe (Becton Dickinson) through which blood was withdrawn from the device by pulling (30 µl/min) using a syringe pump (PHD Ultra CP, Harvard Apparatus), thereby driving blood flow through the microchannels (FIG. 69A). Recalcification of blood was performed after 2 min of operation to permit calcium- and magnesium-dependent platelet-derived thrombus formation.

VIII. FIRST SET OF ALTERNATIVE EMBODIMENTS

A. Embodiments A1-A9

Embodiment A1

A microchannel comprising one or more surfaces, the microchannel having living endothelial cells on all of the microchannel surfaces.

Embodiment A2

The microchannel of embodiment A1, wherein the living endothelial cells are human umbilical vein endothelial cells.

Embodiment A3

The microchannel of embodiment A1, wherein the surfaces are coated with at least one attachment molecule that supports adhesion of the living endothelial cells.

Embodiment A4

The microchannel of embodiment A1, wherein the microchannel includes a top surface, a bottom surface, a first side surface, and a second side surface.

Embodiment A5

The microchannel of embodiment A4, wherein the bottom surface includes a membrane.

Embodiment A6

The microchannel of embodiment A1, wherein the microchannel is in fluid communication with an input port and an output port.

Embodiment A7

The microchannel of embodiment A1, wherein the microchannel has a width in the range of about 50 microns to about 1,000 microns.

Embodiment A8

The microchannel of embodiment A1, wherein the microchannel has a height in the range of about 50 microns to about 200 microns.

Embodiment A9

The microchannel of embodiment A1, wherein the microchannel includes a tube lined with a continuous, confluent layer of endothelial cells.

B. Embodiments B1-B5

Embodiment B1

A device comprising: a body having a microchannel therein, the microchannel including one or more surfaces, the microchannel including living endothelial cells on all of the microchannel surfaces.

Embodiment B2

The device of embodiment B1, wherein the microchannel includes a top surface, a bottom surface, a first side surface, and a second side surface.

Embodiment B3

The device of embodiment B2, wherein the bottom surface includes a membrane.

Embodiment B4

The device of embodiment B3, wherein the membrane is at least partially porous.

Embodiment B5

The device of embodiment B1, further comprising an input port and an output port, the ports being in fluidic communication with the microchannel.

C. Embodiments C1-C3

Embodiment C1

A system comprising: a) a microchannel having one or more surfaces; b) living endothelial cells on all of the surfaces; and (c) fluid moving through the microchannel.

Embodiment C2

The system of embodiment C1, wherein the fluid includes whole blood that contacts the endothelial cells without clotting.

Embodiment C3

The system of embodiment C1, wherein the fluid includes platelets, the platelets being in contact with the endothelial cells without clotting.

D. Embodiments D1-D8

Embodiment D1

A method comprising:
1) providing
   a) a microchannel with one or more surfaces, and
   b) living endothelial cells on all of the surfaces; and
2) introducing fluid into the microchannel.

Embodiment D2

The method of embodiment D1, wherein the living endothelial cells are human umbilical vein endothelial cells.

Embodiment D3

The method of embodiment D1, wherein the fluid is selected from a group consisting of a blood sample, a serum sample, a plasma sample, a lipid solution, a nutrient medium, or a combination of two or more thereof.

Embodiment D4

The method of embodiment D1, wherein the fluid includes whole blood that contacts the endothelial cells without clotting.

Embodiment D5

The method of embodiment D1, wherein the fluid includes platelets, the platelets contacting the endothelial cells without clotting.

Embodiment D6

The method of embodiment D1, further comprising, prior to step 2), exposing the living endothelial cells to a pro-inflammatory cytokine.

Embodiment D7

The method of embodiment D6, wherein the fluid includes whole blood that contacts the endothelial cells under conditions such that a platelet-rich thrombus forms.

Embodiment D8

The method of embodiment D6, wherein the fluid includes platelets, the platelets clotting upon contacting the endothelial cells.

E. Embodiments E1-E8

Embodiment E1

A method comprising:
1) providing
a) a microchannel having one or more surfaces, and
b) fixed endothelial cells on all of the surfaces; and
2) introducing fluid into the microchannel.

Embodiment E2

The method of embodiment E1, wherein the fixed endothelial cells are human umbilical vein endothelial cells.

Embodiment E3

The method of embodiment E1, wherein the fluid is selected from a group consisting of a blood sample, a serum sample, a plasma sample, a lipid solution, a nutrient medium, and a combination of two or more thereof.

Embodiment E4

The method of embodiment E1, wherein the fluid includes whole blood that contacts the endothelial cells without clotting.

Embodiment E5

The method of embodiment E1, wherein the fluid includes platelets, the platelets contacting the endothelial cells without clotting.

Embodiment E6

The method of embodiment E1, wherein the endothelial cells are physically fixed by at least one of drying and dehydration.

Embodiment E7

The method of embodiment E1, wherein the endothelial cells are fixed by at least one of exposing to air, washing with alcohol, acetone, or a solvent that removes at least one of water and lipids.

Embodiment E8

The method of embodiment E1, wherein the endothelial cells are fixed with a chemical fixative.

IX. SECOND SET OF ALTERNATIVE EMBODIMENTS

A. Embodiments A1-A10

Embodiment A1

A method of testing a drug, the method comprising:
a. providing a fluid sample of a subject, the fluid sample including platelets;
b. adding a drug to a portion of the fluid sample to create a test sample;
c. flowing the test sample through a microchannel of a microfluidic device, the microchannel including one or more surfaces having an endothelial cell monolayer thereon, the endothelial cells being in a stimulated state;
d. detecting interaction between platelets in the test sample and the endothelial cells;
e. comparing the level of interaction of step d) with that of a control; and
f. determining whether the drug interfered with a platelet function.

Embodiment A2

The method of embodiment A1, wherein the control includes the fluid sample of the subject without the drug.

Embodiment A3

The method of embodiment A1, wherein the endothelial cells are stimulated with a cytokine.

Embodiment A4

The method of embodiment A3, wherein the cytokine is TNF-α.

Embodiment A5

The method of embodiment A1, wherein the drug is an antiplatelet GP IIb/IIIa antagonist.

Embodiment A6

The method of embodiment A1, wherein the drug is an antibody.

Embodiment A7

The method of embodiment A1, wherein the drug is abciximab.

Embodiment A8

The method of embodiment A1, wherein the microchannel has a top surface, a bottom surface, a first side surface, and a second side surface.

Embodiment A9

The method of embodiment A8, wherein the microchannel includes living endothelial cells on all of the microchannel surfaces.

Embodiment A10

The method of embodiment A8, wherein the microchannel includes fixed endothelial cells on all of the microchannel surfaces.

X. THIRD SET OF ALTERNATIVE EMBODIMENTS

A. Embodiments A1-A14

Embodiment A1

A method of determining if a subject is at risk, or has a disease or disorder, induced by platelet dysfunction, the method comprising:
a. flowing a fluid sample of the subject including platelets over a surface having an endothelial cell monolayer thereon;
b. detecting interaction between platelets in the fluid sample and the endothelial cells;
c. comparing the level of interaction of step b) with that of a control; and
d. identifying the subject to be at risk, or have the disease or disorder, induced by platelet dysfunction when the platelet interaction is higher than the control.

Embodiment A2

The method of embodiment A1, wherein the subject is at increased risk for thrombosis.

Embodiment A3

The method of embodiment A2, further comprising selecting an appropriate therapy and administering the therapy to the subject.

Embodiment A4

The method of embodiment A3, wherein the therapy is anti-platelet therapy.

Embodiment A5

The method of embodiment A3, wherein the therapy is anti-inflammation therapy.

Embodiment A6

The method of embodiment A1, wherein the disease or disorder induced by platelet dysfunction is an inflammatory vascular disease.

Embodiment A7

The method of embodiment A1, wherein the disease or disorder induced by platelet dysfunction is a cardiovascular disorder.

Embodiment A8

The method of embodiment A1, wherein the surface having an endothelial cell monolayer is the surface of a microchannel of a microfluidic device, the device including a body having a microchannel therein.

Embodiment A9

The method of embodiment A8, wherein the microchannel includes a top surface, a bottom surface, a first side surface, and a second side surface.

Embodiment A10

The method of embodiment A9, wherein the microchannel includes living endothelial cells on all of the microchannel surfaces.

Embodiment A11

The method of embodiment A9, wherein the microchannel includes fixed endothelial cells on all of the microchannel surfaces.

Embodiment A12

The method of embodiment A9, wherein the bottom surface includes a membrane.

Embodiment A13

The method of embodiment A12, wherein the membrane is at least partially porous.

Embodiment A14

The method of embodiment A8, wherein the device further includes an input port and an output port, the ports being in fluidic communication with the microchannel.

B. Embodiments B1-B11

Embodiment B1

A method of determining if a subject is at risk or has a disease or disorder induced by platelet dysfunction, the method comprising:
 a. flowing a fluid sample of the subject having platelets through a microchannel of a microfluidic device, the microchannel having one or more surfaces with an endothelial cell monolayer thereon;
 b. detecting interaction between platelets in the fluid sample and the endothelial cells;
 c. comparing the level of interaction of step b) with that of a control; and
 d. identifying the subject to be at risk or have the disease or disorder induced by platelet dysfunction when the platelet interaction is higher than the control.

Embodiment B2

The method of embodiment B1, wherein the subject is at increased risk for thrombosis.

Embodiment B3

The method of embodiment B2, further comprising selecting an appropriate therapy and administering the therapy to the subject.

Embodiment B4

The method of embodiment B3, wherein the therapy is anti-platelet therapy.

Embodiment B5

The method of embodiment B3, wherein the therapy is anti-inflammation therapy.

Embodiment B6

The method of embodiment B1, wherein the disease or disorder induced by platelet dysfunction is an inflammatory vascular disease.

Embodiment B7

The method of embodiment B1, wherein the disease or disorder induced by platelet dysfunction is cardiovascular disorder.

Embodiment B8

The method of embodiment B1, wherein the microchannel includes a top surface, a bottom surface, a first side surface, and a second side surface.

Embodiment B9

The method of embodiment B8, wherein the microchannel includes living endothelial cells on all of the microchannel surfaces.

Embodiment B10

The method of embodiment B8, wherein the microchannel includes fixed endothelial cells on all of the microchannel surfaces.

Embodiment B11

The method of embodiment B8, wherein the bottom surface includes a membrane.

C. Embodiments C1-C4

Embodiment C1

A method of determining if a subject on an antiplatelet agent is at risk for a thrombotic event, the method comprising:
 a. flowing a fluid sample of the subject having platelets through a microchannel of a microfluidic device, the microchannel having one or more surfaces with an endothelial cell monolayer thereon, the endothelial cells being in a stimulated state;
 b. detecting interaction between platelets in the fluid sample and the endothelial cells;
 c. comparing the level of interaction of step b) with that of a healthy control; and
 d. identifying the subject to be at risk of a thrombotic event when the platelet interaction is higher than the healthy control.

Embodiment C2

The method of embodiment C1, wherein the platelet interaction includes platelet adhesion.

Embodiment C3

The method of embodiment C1, wherein the antiplatelet agent is aspirin.

Embodiment C4

The method of embodiment C1, wherein the antiplatelet agent is Clopidogrel.

XI. FOURTH SET OF ALTERNATIVE EMBODIMENTS

A. Embodiments A1-A40

Embodiment A1

A method of determining a platelet function, the method comprising:
 a. flowing a fluid sample over a surface having a fixed endothelial cell monolayer thereon; and
 b. in response to detecting interaction between platelets in the fluid sample and the fixed endothelial cell monolayer, determining a function of the platelets in the fluid sample.

Embodiment A2

The method of embodiment A1, wherein the fixed endothelial cell monolayer is derived from at least one of (i)

fixing an endothelial cell extract and (ii) endothelial cell-associated proteins that are adhered to the surface.

Embodiment A3

The method of embodiment A2, wherein the endothelial cell-associated proteins include at least one of a procoagulatory protein and an anti-coagulatory protein.

Embodiment A4

The method of embodiment A1, wherein the fluid sample is selected from a group consisting of a blood sample, a serum sample, a plasma sample, a lipid solution, a nutrient medium, and a combination of two or more thereof.

Embodiment A5

The method of embodiment A1, wherein the surface is a surface of a microchannel.

Embodiment A6

The method of embodiment A1, wherein the surface is a surface of a membrane.

Embodiment A7

The method of embodiment A6, wherein the membrane is configured to separate a first microchannel and a second microchannel in a microfluidic device.

Embodiment A8

The method of embodiment A7, wherein the microfluidic device is an organ-on-chip device.

Embodiment A9

The method of embodiment A7, wherein a first surface of the membrane facing the first microchannel includes the fixed endothelial cell monolayer thereon, and a second surface of the membrane facing the second microchannel includes tissue-specific cells adhered thereon.

Embodiment A10

The method of embodiment A1, wherein the fixed endothelial cell monolayer is derived from fixing an endothelial cell monolayer that has been grown on the surface for a period of time.

Embodiment A11

The method of embodiment A10, wherein the endothelial cell monolayer is physically fixed by at least one of drying and dehydration.

Embodiment A12

The method of embodiment A10, wherein the endothelial cell monolayer is physically fixed by at least one of exposing to air and washing with at least one of alcohol, acetone, and a solvent that removes at least one of water and lipids.

Embodiment A13

The method of embodiment A1, wherein the endothelial cell monolayer is fixed with a chemical fixative.

Embodiment A14

The method of embodiment A13, wherein the chemical fixative is selected from the group consisting of formaldehyde, paraformaldehyde, formalin, glutaraldehyde, mercuric chloride-based fixatives, precipitating fixatives, dimethyl suberimidate (DMS), Bouin's fixative, and a combination of two or more thereof, the mercuric chloride-based fixatives including Helly and Zenker's solution, the precipitating fixatives including at least one of ethanol, methanol, and acetone.

Embodiment A15

The method of embodiment A10, wherein the endothelial cell monolayer is fixed with a decellularization solvent that stabilizes surface membrane protein configuration and a cytoskeleton of a cell.

Embodiment A16

The method of embodiment A15, wherein the decellularization solvent includes an aqueous solution having at least one of a detergent and a high pH solution.

Embodiment A17

The method of embodiment A1, wherein endothelial cells of the fixed endothelial cell monolayer are derived from a subject.

Embodiment A18

The method of embodiment A1, wherein endothelial cells of the fixed endothelial cell monolayer are differentiated from subject-specific pluripotent stem cells.

Embodiment A19

The method of embodiment A1, wherein the fixed endothelial cell monolayer is derived from healthy cells.

Embodiment A20

The method of embodiment A1, wherein the fixed endothelial cell monolayer is derived from diseased cells.

Embodiment A21

The method of embodiment A20, wherein the diseased cells are generated by contacting healthy endothelial cells with an inflammation-inducing agent prior to the treatment with a fixative.

Embodiment A22

The method of embodiment A21, wherein the inflammation-inducing agent includes at least one of a physical stimulus, a chemical agent, a biological agent, a molecular agent, or a combination of two or more thereof.

Embodiment A23

The method of embodiment A20, wherein the diseased cells are derived from a subject diagnosed with a disease.

Embodiment A24

The method of embodiment A1, further comprising, when the fluid sample includes a blood sample, removing red blood cells from the blood sample prior to flowing the blood sample over the surface.

Embodiment A25

The method of embodiment A1, wherein the detecting includes measuring at least one of temporal and spatial interaction dynamics of the platelets in the fluid sample.

Embodiment A26

The method of embodiment A25, wherein the interaction dynamics of the platelets includes at least one of binding dynamics of the platelets to the fixed endothelial cell monolayer, binding dynamics of the platelets to each other, and a combination thereof.

Embodiment A27

The method of embodiment A1, wherein the platelets in the blood sample are label-free.

Embodiment A28

The method of embodiment A1, wherein the platelets in the blood sample are labeled with a detectable label.

Embodiment A29

The method of embodiment A28, wherein the detectable label is a fluorescent label.

Embodiment A30

The method of embodiment A1, wherein the detecting is performed by an imaging-based method.

Embodiment A31

The method of embodiment A30, wherein the imaging-based method includes time-lapse microscopy.

Embodiment A32

The method of embodiment A1, wherein the detecting is performed by at least one of a wide-field holography device, an impedance spectroscopy device, a flow sensor, a pressure sensor, and a combination of two or more thereof.

Embodiment A33

The method of embodiment A1, wherein the surface has been stored at room temperature for a period of time prior to the flowing of the fluid sample.

Embodiment A34

The method of embodiment A1, wherein the surface has been stored at a temperature of about 4° C. or lower for a period of time prior to the flowing of the fluid sample.

Embodiment A35

The method of embodiment A33, wherein the period of time is in the range of about 1 day to about 5 days.

Embodiment A36

The method of embodiment A1, wherein the fluid sample is flowed at a physiological shear rate or a pathological shear rate.

Embodiment A37

The method of embodiment A1, wherein the fluid sample is flowed at a shear rate of about 50 sec$^{-1}$ to about 10,000 sec$^{-1}$.

Embodiment A38

The method of embodiment A1, wherein the fixed endothelial cell monolayer and the fluid sample are derived from the same subject.

Embodiment A39

The method of embodiment A1, wherein the fixed endothelial cell monolayer and the fluid sample are derived from different sources.

Embodiment A40

The method of embodiment A1, wherein the fluid sample includes at least one of calcium ions and magnesium ions.

B. Embodiments B1-B2

Embodiment B1

A system for determining temporal dynamics of platelets in a fluid sample, the system comprising:
 a. a solid substrate having a surface with a fixed endothelial cell monolayer thereon;
 b. a detection module configured to receive the solid substrate and to detect spatial and temporal interaction of platelets in a fluid sample with the surface when the fluid sample is flowed over the surface along a flow axis; and
 c. a computer system for computing platelet dynamics, the computer system including one or more processors and a memory to store one or more programs, the one or more programs including instructions for:
  i. storing time-lapse data of detectable signals collected from the detection module, wherein the detectable signals represent the spatial and temporal interaction of the platelets with the surface,
  ii. generating a kymograph from at least a portion of the stored time-lapse data, wherein the time axis of the kymograph indicates at least a portion of the time-lapse duration, and the space axis of the kymograph indicates the detectable signals along the flow axis, iii. computing, based on the generated kymograph, a rate of fluctuation in coefficient of variation (CV) of the detectable signals to generate a temporal platelet dynamics index, and
iv. determining the presence of reactive platelets in the fluid sample when the temporal platelet dynamics index is higher than a temporal control value, or determining the absence of reactive platelets in the fluid sample when the temporal platelet dynamics index is no more than the temporal control value; and d. a display module for displaying a content based in part on the computed output from the computer system, wherein the content includes a signal indicative of at least one of the presence of reactive platelets and platelet aggregation in the fluid sample, or a signal indicative of at least one of the absence of reactive platelets and platelet aggregation in the fluid sample.

Embodiment B2

The system of embodiment B1, wherein the detectable signals are averaged across the width of the surface, transverse to the flow axis, prior to stacking to generate the kymograph.

C. Embodiments C1-C8

Embodiment C1

A system for determining spatial dynamics of platelets in a fluid sample, the system comprising:
a. a solid substrate having a surface with a fixed endothelial cell monolayer thereon;
b. a detection module configured to receive the solid substrate and to detect spatial and temporal interaction of platelets in a fluid sample with the surface when the fluid sample is flowed over the surface along a flow axis;
c. a computer system for computing platelet dynamics, the computer system including one or more processors and a memory to store one or more programs, the one or more programs comprising instructions for:
  i. storing time-lapse data of detectable signals collected from the detection module, wherein the time-lapse data represents the spatial and temporal interaction of the platelets with the surface,
  ii. generating, from at least a portion of the stored time-lapse data, a spatial map of temporal variances of the detectable signals, wherein each pixel of the spatial map corresponds to a time-averaged coefficient of variation (CV) of the detectable signals,
  iii. computing, based on the generated spatial map, an inter-quartile range (IQR) of the map to generate a spatial platelet dynamics index, and
  iv. determining the presence of platelet aggregation in the fluid sample when the spatial platelet dynamics index is higher than a spatial control value; or determining the absence of platelet aggregation in the fluid sample when the spatial platelet dynamics index is no more than the spatial control value; and
d. a display module for displaying a content based in part on the computed output from the computer system, wherein the content includes a signal indicative of at least one of the presence of reactive platelets and platelet aggregation in the fluid sample, or a signal indicative of at least one of the absence of reactive platelets and platelet aggregation in the fluid sample.

Embodiment C2

The system of embodiment C1, wherein the time-lapse data is presented in the form of images.

Embodiment C3

The system of embodiment C2, wherein the detection module includes an imaging-based device.

Embodiment C4

The system of embodiment C3, wherein the imaging-based device includes a microscope or a microscope blade.

Embodiment C5

The system of embodiment C1, wherein the display module is selected from a group consisting of a computer display, a screen, a monitor, a physical printout, and a storage device, the content being selected from a group consisting of an email, a text message, a website, and stored information on the storage device.

Embodiment C6

The system of embodiment C1, wherein the one or more programs include instructions for determining platelet reactivity based on a linear or non-linear function having the spatial and temporal dynamic parameters.

Embodiment C7

The system of embodiment C1, wherein the one or more programs further include instructions for computing area-averaged platelet adhesion over at least a portion of the surface.

Embodiment C8

The system of embodiment C1, wherein the fluid sample includes a blood sample.

D. Embodiments D1-D7

Embodiment D1

A method of determining if a subject is at risk or has a disease or disorder induced by platelet dysfunction, the method comprising:
a. flowing a fluid sample of the subject over a surface with a fixed endothelial cell monolayer thereon;
b. detecting interaction between platelets in the fluid sample and the surface; and
c. identifying the subject to be
at risk or have the disease or disorder induced by platelet dysfunction when the platelet interaction is higher than a control, or
less likely to have a disease or disorder induced by platelet dysfunction when the platelet interaction is no more than the control.

Embodiment D2

The method of embodiment D1, wherein the method is implemented in a computer system having one or more processors and a memory storing one or more programs for execution by the one or more processors, the one or more programs including instructions for:

i. generating a kymograph from at least a portion of time-lapse data of detectable signals representing spatial and temporal interaction of the platelets with the surface, wherein the time axis of the kymograph indicates at least a portion of the time-lapse duration, and the space axis of the kymograph indicates the detectable signals along a flow axis;

ii. computing, based on the generated kymograph, a rate of fluctuation in coefficient of variation (CV) of the detectable signals to generate a temporal platelet dynamics index; and iii. determining
the presence of reactive platelets in the fluid sample when the temporal platelet dynamics index is higher than a temporal control value, thereby identifying the subject to be at risk or have the disease or disorder induced by platelet dysfunction, or
the absence of reactive platelets in the fluid sample when the temporal platelet dynamics index is no more than the temporal control value, thereby identifying the subject to be less likely to have a disease or disorder induced by platelet dysfunction.

Embodiment D3

The method of embodiment D1, wherein the method is implemented in a computer system having one or more processors and a memory storing one or more programs for execution by the one or more processors, the one or more programs including instructions for:

i. generating, from at least a portion of time-lapse data of detectable signals representing spatial and temporal interaction of the platelets with the surface, a spatial map of temporal variances of the detectable signals, wherein each pixel of the spatial map corresponds to a time-averaged coefficient of variation (CV);

ii. computing, based on the generated spatial map, an inter-quartile range (IQR) of the map to generate a spatial platelet dynamics index; and iii. determining
the presence of platelet aggregation in the fluid sample when the spatial platelet dynamics index is higher than a spatial control value, thereby identifying the subject to be at risk or have the disease or disorder induced by platelet dysfunction, or
the absence of platelet aggregation in the fluid sample when the spatial platelet dynamics index is no more than the spatial control value, thereby identifying the subject to be less likely to have a disease or disorder induced by platelet dysfunction.

Embodiment D4

The method of embodiment D1, wherein the fixed endothelial cell monolayer is subject-specific.

Embodiment D5

The method of embodiment D1, wherein the disease or disorder induced by platelet dysfunction is selected from a group consisting of thrombosis, an inflammatory vascular disease, a cardiovascular disorder, vasculopathies, and a combination of two or more thereof, the inflammatory vascular disease including sepsis or rheumatoid arthritis, the cardiovascular disorder including acute coronary syndromes, stroke, or diabetes mellitus, the vasculopathies including malaria or disseminated intravascular coagulation.

Embodiment D6

The method of embodiment D1, wherein the fluid sample includes a blood sample.

Embodiment D7

The system of embodiment D1, wherein the fluid sample includes a blood sample.

E. Embodiments E1-E10

Embodiment E1

A composition comprising:
a. a solid substrate having a surface with a fixed endothelial cell monolayer thereon; and
b. a fluid sample having platelets in contact with the surface.

Embodiment E2

The composition of embodiment E1, wherein the fluid sample includes a blood sample.

Embodiment E3

The composition of embodiment E1, wherein the fixed endothelial cell monolayer is derived from fixing an endothelial cell monolayer that has been grown on the surface for a period of time.

Embodiment E4

The composition of embodiment E3, wherein the endothelial cell monolayer is derived from fixing at least one of endothelial cell extract or endothelial cell-associated proteins that are adhered to the surface.

Embodiment E5

The composition of embodiment E1, wherein the solid substrate is selected from a group consisting of a microscopic slide, a cell culture dish, a microfluidic device, a microwell, and any combinations thereof.

Embodiment E6

The composition of embodiment E1, wherein the surface is a surface of a microchannel.

Embodiment E7

The composition of embodiment E1, wherein the surface is a surface of a membrane.

Embodiment E8

The composition of embodiment E7, wherein the membrane is configured to separate a first microchannel and a second microchannel in a microfluidic device.

Embodiment E9

The composition of embodiment E8, wherein the microfluidic device is an organ-on-chip device.

Embodiment E10

The composition of embodiment E8, wherein a first surface of the membrane is facing the first microchannel has the fixed endothelial cell monolayer thereon, and a second surface of the membrane facing the second microchannel has tissue-specific cells adhered thereon.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A method for evaluating an agent in vitro, the method comprising:
    providing a solid substrate having a first microchannel with fixed endothelial cells in at least one region of the first microchannel;
    flowing a fluid having an agent through the first microchannel; and
    measuring at least one parameter relating to a thrombosis function in at least a portion of the at least one region to obtain data.

2. The method of claim 1, wherein the fluid is selected from a group consisting of a blood sample, a serum sample, a plasma sample, a lipid solution, a nutrient medium, and a combination of two or more thereof.

3. The method of claim 1, wherein the endothelial cells include a lumen within the first microchannel.

4. The method of claim 1, wherein the measuring includes imaging.

5. The method of claim 1, wherein the fluid further has at least one blood component.

6. The method of claim 5, wherein the blood component comes from a patient.

7. The method of claim 1, wherein having solid substrate includes a second microchannel having at least one type of parenchymal cells.

8. A method comprising:
    (a) providing a microchannel having a lumen of fixed endothelial cells; and
    (b) flowing fluid into the microchannel, the fluid having at least one blood component, said blood component selected from the group consisting of blood, serum, plasma and platelets.

9. The method of claim 8, wherein the fixed endothelial cells are human umbilical vein endothelial cells.

10. The method of claim 8, further comprising:
    (c) determining presence or absence of one or more of activated platelets and nonactivated platelets and evaluating clot formation of the at least one blood component in at least a portion of said lumen of fixed endothelial cells; and
    (d) carrying out one or more of
        diagnosing a disease or disorder based on the presence or absence of one or more of activated platelets and nonactivated platelets,
        selecting therapy based on the presence or absence of one or more of activated platelets and nonactivated platelets,
        monitoring treatment efficacy based on the presence or absence of one or more of activated platelets and nonactivated platelets,
        screening a drug based on the presence or absence of one or more of activated platelets and nonactivated platelets, and
        determining drug toxicology based on the presence or absence of one or more of activated platelets and nonactivated platelets.

11. The method of claim 10, wherein the evaluating thrombosis function includes imaging at least a portion of the lumen of fixed endothelial cells.

12. The method of claim 8, wherein the fluid further includes an agent.

13. The method of claim 12, wherein the agent includes at least one of a drug, an antibody, and a cytokine.

14. A method of testing a drug, the method comprising:
    (a) providing a fluid sample, the fluid sample including at least one blood component;
    (b) adding a drug to a portion of the fluid sample to create a test sample;
    (c) flowing the test sample through a microchannel of a microfluidic device, the microchannel including one or more surfaces with fixed endothelial cells thereon, the fixed endothelial cells forming a lumen;
    (d) evaluating at least one thrombosis function in at least a portion of the lumen of fixed endothelial cells;
    (e) determining the presence or absence of one or more of activated platelets and nonactivated platelets; and
    (f) determining efficacy or toxicology of the drug based on the presence or absence of one or more of activated platelets and nonactivated platelets.

15. The method of claim 14, further comprising:
    (g) comparing the level of interaction of step (d) with that of a control.

16. The method of claim 14, wherein the control includes the fluid sample without the drug.

17. The method of claim 14, wherein the microfluidic device further includes parenchymal cells.

18. The method of claim 6, further comprising analyzing the data to determine the presence or absence of one or more of activated platelets and nonactivated platelets.

19. The method of claim 18, further comprising administering a therapy to the patient based on the presence or absence of one or more of activated platelets and nonactivated platelets.

20. The method of claim 18, further comprising screening a drug based on the presence or absence of one or more of activated platelets and nonactivated platelets.

21. The method of claim 18, further comprising determining drug toxicology based on the presence or absence of one or more of activated platelets and nonactivated platelets.

* * * * *